United States Patent
Lee et al.

(10) Patent No.: US 9,761,808 B2
(45) Date of Patent: Sep. 12, 2017

(54) HETEROCYCLIC COMPOUND AND ORGANIC LIGHT-EMITTING DEVICE COMPRISING THE SAME

(71) Applicant: Samsung Display Co., Ltd., Yongin, Gyeonggi-Do (KR)

(72) Inventors: Sun-Young Lee, Yongin (KR); Yoon-Hyun Kwak, Yongin (KR); Bum-Woo Park, Yongin (KR); Jong-Won Choi, Yongin (KR); Wha-Il Choi, Yongin (KR); So-Yeon Kim, Yongin (KR); Ji-Youn Lee, Yongin (KR)

(73) Assignee: SAMSUNG DISPLAY CO., LTD. (KR)

( * ) Notice: Subject to any disclaimer, the term of this patent is extended or adjusted under 35 U.S.C. 154(b) by 238 days.

(21) Appl. No.: 14/217,832

(22) Filed: Mar. 18, 2014

(65) Prior Publication Data

US 2015/0053934 A1    Feb. 26, 2015

(30) Foreign Application Priority Data

Aug. 22, 2013    (KR) .................. 10-2013-0099884

(51) Int. Cl.
*H01L 51/00*    (2006.01)
*C07D 495/04*    (2006.01)
(Continued)

(52) U.S. Cl.
CPC ........ *H01L 51/0061* (2013.01); *C07D 209/86* (2013.01); *C07D 495/04* (2013.01);
(Continued)

(58) Field of Classification Search
None
See application file for complete search history.

(56) References Cited

U.S. PATENT DOCUMENTS 4,873,258 A    10/1989    Bair
4,999,369 A    3/1991    Bair
(Continued)

FOREIGN PATENT DOCUMENTS

JP    08-012600 A    1/1996
JP    11-003782 A    6/1999
(Continued)

OTHER PUBLICATIONS

Machine English translation of KR 10-2012-0081539. Dec. 13, 2015.*

(Continued)

*Primary Examiner* — J. L. Yang
(74) *Attorney, Agent, or Firm* — Innovation Counsel LLP

(57) ABSTRACT

A heterocyclic compound represented by Formula 1 and an organic light-emitting device including the same.

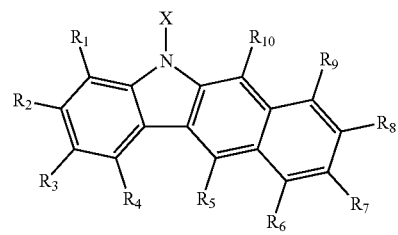

Formula 1

The heterocyclic compound represented by Formula 1 has excellent light emitting characteristics and high charge transporting capabilities.

17 Claims, 2 Drawing Sheets

(51) Int. Cl.
*C07D 209/86* (2006.01)
*C09K 11/06* (2006.01)
*H01L 51/50* (2006.01)

(52) U.S. Cl.
CPC .......... *C09K 11/06* (2013.01); *H01L 51/0072* (2013.01); *C09K 2211/1029* (2013.01); *C09K 2211/1059* (2013.01); *C09K 2211/1092* (2013.01); *H01L 51/0081* (2013.01); *H01L 51/0085* (2013.01); *H01L 51/5016* (2013.01); *H01L 51/5056* (2013.01); *H01L 51/5072* (2013.01)

(56) References Cited

U.S. PATENT DOCUMENTS

| | | | |
|---|---|---|---|
| 5,635,308 | A | 6/1997 | Inoue et al. |
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 2004/0247937 | A1* | 12/2004 | Chen ................ C09K 11/06 428/690 |
| 2006/0113905 | A1* | 6/2006 | Nakamura .......... H01L 27/3244 313/511 |
| 2006/0131562 | A1* | 6/2006 | Li ...................... H01L 51/002 257/40 |
| 2011/0210318 | A1 | 9/2011 | Bae et al. |
| 2012/0211733 | A1 | 8/2012 | Hwang et al. |

FOREIGN PATENT DOCUMENTS

| | | | | |
|---|---|---|---|---|
| KR | 10-0573137 | B1 | 10/2005 | |
| KR | 10-2010-0023783 | A | 3/2010 | |
| KR | 10-2012-0081539 | * | 7/2012 | ............. C09K 11/06 |
| KR | 10-2012-0112424 | A | 10/2012 | |
| KR | 10-2012-0122897 | * | 11/2012 | ........... C07D 209/82 |

OTHER PUBLICATIONS

Machine English Translation of Je et al. (KR 10-2012-0122897). Jun. 1, 2016.*
C. W. Tang, et al., "Organic Electroluminescent Diodes", Appl. Phys. Lett., vol. 51, No. 12, pp. 913-915, Sep. 21, 1987.
Chihaya Adachi, et al., "Confinement of Charge Carriers and Molecular Excitons within 5-nm-thick Emitter Layer in Organic Electroluminescent Devices with a Double Heterostructure", Appl. Phys. Lett., vol. 57, No. 6, pp. 531-533, Aug. 6, 1990.
Youichi Sakamoto, et al., "Synthesis, Characterization, and Electron-Transport Property of Perfluorinated Phenylene Dendrimers", J. Am. Chem. Soc., 122, pp. 1832-1833, Feb. 15, 2000.
Shigehiro Yamaguchi, et al., "Diphenylamino-Substituted 2,5-Diarylsiloles for Single-Layer Organic Electroluminescent Devices", Chem. Lett., 2001, pp. 98-99, Nov. 10, 2000.

* cited by examiner

HETEROCYCLIC COMPOUND AND ORGANIC LIGHT-EMITTING DEVICE COMPRISING THE SAME

RELATED APPLICATIONS

This application claims the benefit of Korean Patent Application No. 10-2013-0099884, filed on Aug. 22, 2013, in the Korean Intellectual Property Office, the disclosure of which is incorporated herein in its entirety by reference.

BACKGROUND

1. Field

The present application relates to a heterocyclic compound and an organic light-emitting device including the same,

2. Description of the Related Art

Organic light-emitting devices (OLEDs), which are self-emitting devices, have a wide viewing angle, excellent contrast, quick response, high brightness, and excellent driving voltage characteristics, and provide multicolored images.

A general organic light-emitting device has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films respectively formed of organic compounds.

An operating principle of an organic light-emitting device having the above-described structure is as follows.

When a voltage is applied between the anode and the cathode, holes injected from the anode move to the EML via the HTL, and electrons injected from the cathode move to the EML via the ETL. Carriers such as the holes and electrons recombine in the EML to generate excitons. When the excitons drop from an excited state to a ground state, light is emitted.

Luminous efficiency of an organic light-emitting device mainly depends upon a luminescent material. Although fluorescent materials or phosphorescent materials have been used as luminescent materials, luminous efficiency, driving voltage, and lifespan thereof are not satisfactory. Thus, there is still a need to develop a material that is more stable and has better performance than those fluorescent and phosphorescent materials.

SUMMARY

One or more embodiments include a heterocyclic compound and an organic light-emitting device including the same. The heterocyclic compound has excellent electrical characteristics, high charge transporting capabilities, excellent light-emission capabilities, high glass transition temperature, and high ability to prevent crystallization, and is used as electron transporting materials for all color-fluorescent and phosphorescent devices, such as red, green, blue, or white fluorescent and phosphorescent devices, or as green, blue, or white light-emitting materials, having higher luminous efficiency, longer lifespan, and more suitable color coordinates than conventional materials. The organic light-emitting device including the heterocyclic compound has high luminous efficiency, low driving voltage, high brightness, and long lifespan.

Additional aspects will be set forth in part in the description which follows and, in part, will be apparent from the description, or may be learned by practice of the presented embodiments.

According to one or more embodiments, a heterocyclic compound is represented by Formula 1 below:

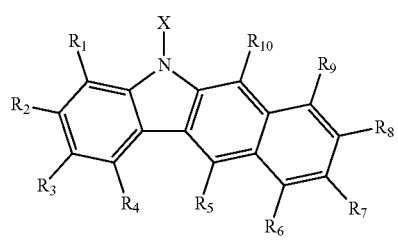

Formula 1

In Formula 1, $R_1$ to $R_{10}$ are each independently a hydrogen atom, a deuterium atom, a halogen atom, a cyano group, a substituted or unsubstituted $C_1$-$C_{60}$ alkyl group, a substituted or unsubstituted $C_1$-$C_{60}$ alkenyl group, a substituted or unsubstituted $C_1$-$C_{60}$ alkynyl group, a substituted or unsubstituted $C_6$-$C_{60}$ aryl group, a substituted or unsubstituted $C_1$-$C_{60}$ heteroaryl group, an amino group substituted with a $C_6$-$C_{60}$ aryl group, a $C_1$-$C_{60}$ alkyl group, a $C_1$-$C_{60}$ alkenyl group, or a $C_1$-$C_{60}$ alkynyl group, or a substituted or unsubstituted $C_6$-$C_{60}$ condensed polycyclic group, X is a substituted or unsubstituted $C_1$-$C_{50}$ alkyl group, a substituted or unsubstituted $C_6$-$C_{60}$ aryl group, a substituted or unsubstituted $C_1$-$C_{60}$ heteroaryl group, or a substituted or unsubstituted $C_6$-$C_{60}$ condensed polycyclic group, and $R_6$ and $R_7$ are fused to each other, thereby forming an aromatic ring, or $R_8$ and $R_9$ are fused to each other, thereby forming an aromatic ring.

According to one or more embodiments, an organic light-emitting device includes a first electrode; a second electrode; and an organic layer interposed between the first electrode and the second electrode, wherein the organic layer includes the heterocyclic compound.

According to one or more embodiments, a flat panel display apparatus includes the organic light-emitting device, wherein a first electrode of the organic light-emitting device is electrically connected to a source electrode or a drain electrode of a thin film transistor.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
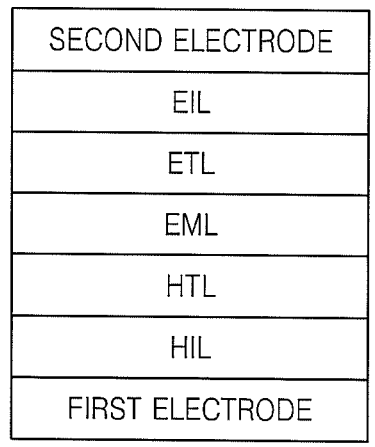
FIG. 1 is a schematic cross-sectional view of an organic light-emitting device according to an embodiment.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

A heterocyclic compound according to an embodiment is represented by Formula 1 below.

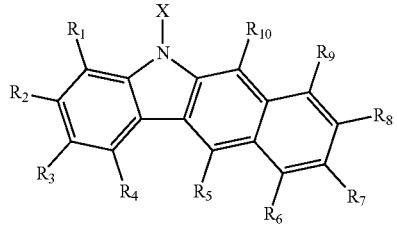

Formula 1

In Formula 1, $R_1$ to $R_{10}$ are each independently a hydrogen atom, a deuterium atom, a halogen atom, a cyano group, a substituted or unsubstituted $C_1$-$C_{60}$ alkyl group, a substituted or unsubstituted $C_1$-$C_{60}$ alkenyl group, a substituted or unsubstituted $C_1$-$C_{60}$ alkynyl group, a substituted or unsubstituted $C_6$-$C_{60}$ aryl group, a substituted or unsubstituted $C_1$-$C_{60}$ heteroaryl group, an amino group substituted with a $C_6$-$C_{60}$ aryl group, a $C_1$-$C_{60}$ alkyl group, a $C_1$-$C_{60}$ alkenyl group, or a $C_1$-$C_{60}$ alkynyl group, or a substituted or unsubstituted $C_6$-$C_{60}$ condensed polycyclic group, X is a substituted or unsubstituted $C_1$-$C_{50}$ alkyl group, a substituted or unsubstituted $C_6$-$C_{60}$ aryl group, a substituted or unsubstituted $C_1$-$C_{60}$ heteroaryl group, or a substituted or unsubstituted $C_6$-$C_{60}$ condensed polycyclic group, $R_6$ and $R_7$ are fused to each other, thereby forming an aromatic ring, or $R_8$ and $R_9$ are fused to each other, thereby forming an aromatic ring.

The heterocyclic compound according to an embodiment may be used as a light emitting material and/or a hole transporting material or a hole injecting material for an organic light-emitting device. In addition, the heterocyclic compound according to an embodiment is thermostable and has a large band gap between a highest occupied molecular orbit (HOMO) and a lowest occupied molecular orbit (LUMO), thereby easily controlling an energy level according to a substituent introduced thereinto. Due to these properties, the heterocyclic compound may be efficiently used as a phosphorescent host.

According to an embodiment, the heterocyclic compound of Formula 1 may also be represented by Formula 2 or Formula 3 below.

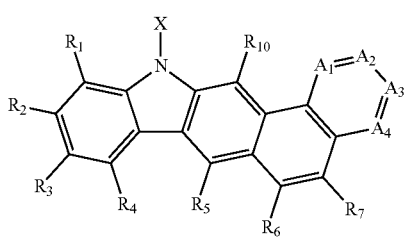

Formula 2

In Formula 2, $R_1$ to $R_7$, $R_{10}$, and X are as defined above, $A_1$ to $A_4$ are each independently $=CR_{21}—$ or $=NR_{22}—$, $R_{21}$ to $R_{22}$ are each independently: a non-bonding electron; a hydrogen atom; a deuterium atom; a halogen atom; a cyano group; a substituted or unsubstituted $C_1$-$C_{60}$ alkyl group; a substituted or unsubstituted $C_1$-$C_{60}$ alkenyl group; a substituted or unsubstituted $C_1$-$C_{60}$ alkynyl group; a substituted or unsubstituted $C_6$-$C_{60}$ aryl group; a substituted or unsubstituted $C_1$-$C_{60}$ heteroaryl group; an amino group substituted with a $C_6$-$C_{60}$ aryl group, a $C_1$-$C_{60}$ alkyl group, a $C_1$-$C_{60}$ alkenyl group, or a $C_1$-$C_{60}$ alkynyl group; or a substituted or unsubstituted $C_6$-$C_{60}$ condensed polycyclic group, $R_{21}$ and $R_{22}$ of $A_1$ to $A_4$ are same or different, and adjacent $R_{21}$ and $R_{22}$ may be selectively fused to each other, thereby forming a ring.

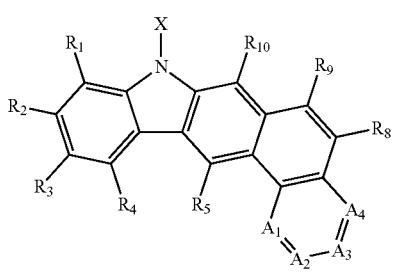

Formula 3

In Formula 3, $R_1$ to $R_5$, $R_5$ to $R_{10}$ and X are as defined above, $A_1$ to $A_4$ are each independently $=CR_{21}—$ or $=NR_{22}—$, $R_{21}$ to $R_{22}$ are each independently: a non-bonding electron; a hydrogen atom; a deuterium atom; a halogen atom; a cyano group; a substituted or unsubstituted $C_1$-$C_{60}$ alkyl group; a substituted or unsubstituted $C_1$-$C_{60}$ alkenyl group; a substituted or unsubstituted $C_1$-$C_{60}$ alkynyl group; a substituted or unsubstituted $C_6$-$C_{60}$ aryl group; a substituted or unsubstituted $C_1$-$C_{60}$ heteroaryl group; an amino group substituted with a $C_6$-$C_{60}$ aryl group, a $C_1$-$C_{60}$ alkyl group, a $C_1$-$C_{60}$ alkenyl group, or a $C_1$-$C_{60}$ alkynyl group; or a substituted or unsubstituted $C_6$-$C_{60}$ condensed polycyclic group, $R_{21}$ and $R_{22}$ of $A_1$ to $A_4$ are same or different, and adjacent $R_{21}$ and $R_{22}$ may be selectively fused to each other, thereby forming a ring.

Substituents of the heterocyclic compound of Formula 1 will be described in more detail.

According to an embodiment, $R_7$ and $R_8$ of Formula 1 may be each independently one of Formulae 2a to 2c below.

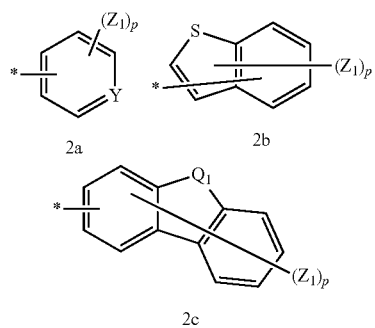

In Formulae 2a to 2c, $Q_1$ is a linking group represented by $—N(R_{31})—$, $—S—$, or $—O—$; Y is $—N=$ or $—CH=$; $Z_1$ and $R_{31}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, an amino group substituted with a $C_6$-$C_{20}$ aryl group or a $C_1$-$C_{20}$ heteroaryl group, a halogen group, a cyano group, a nitro group, a hydroxyl group, or a carboxyl group; p is an integer from 1 to 7; and * is a binding site.

According to another embodiment, X of Formula 1 may be one of Formulae 3a and 3b below.

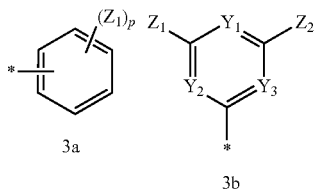

In Formulae 3a and 3b, $Y_1$ to $Y_3$ are each independently —N= or —CH=; $Z_1$ and $Z_2$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, an amino group substituted with a $C_6$-$C_{20}$ aryl group or a $C_1$-$C_{20}$ heteroaryl group, a halogen group, a cyano group, a nitro group, a hydroxyl group, or a carboxyl group; p is an integer from 1 to 5; and * is a binding site.

According to another embodiment, $R_1$ to $R_5$ and $R_{10}$ of Formula 1 may be each independently a hydrogen atom or a deuterium atom.

Hereinafter, substituents used herein will now be described in detail. In this regard, the numbers of carbon atoms in the substituents are presented only for illustrative purposes and do not limit the characteristics of the substituents. Substituents that are not defined herein are defined as well known in the art.

The unsubstituted $C_1$-$C_{60}$ alkyl group may be linear or branched. Examples of the alkyl group include, but are not limited to, methyl, ethyl, propyl, isobutyl, sec-butyl, pentyl, iso-amyl, hexyl, heptyl, octyl, nonanyl, and dodecyl. At least one hydrogen atom of the alkyl group may be substituted with a deuterium atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_4$-$C_{16}$ heteroaryl group.

The unsubstituted $C_2$-$C_{60}$ alkenyl group refers to a hydrocarbon group having at least one carbon-carbon double bond within or at a terminal of the alkyl group. Examples of the $C_2$-$C_{60}$ alkenyl group include ethenyl, propenyl, and butenyl. At least one hydrogen atom of the unsubstituted $C_2$-$C_{60}$ alkenyl group may be substituted with the same substituents as described above in connection with the alkyl group.

The unsubstituted $C_2$-$C_{60}$ alkynyl group refers to a hydrocarbon group having at least one carbon-carbon triple bond within or at a terminal of the alkyl group. Examples of the unsubstituted $C_2$-$C_{60}$ alkynyl group include acetylene, propylene, phenylacetylene, naphthylacetylene, isopropylacetylene, t-butylacetylene, and diphenylacetylene. At least one hydrogen atom of the unsubstituted $C_2$-$C_{60}$ alkynyl group may be substituted with the same substituents as described above in connection with the alkyl group.

The unsubstituted $C_3$-$C_{60}$ cycloalkyl group refers to a $C_3$-$C_{60}$ cyclic alkyl group. At least one hydrogen atom of the cycloalkyl group may be substituted with the same substituent group described above in connection with the $C_1$-$C_{60}$ alkyl group.

The unsubstituted $C_1$-$C_{60}$ alkoxy group refers to a group having a structure of —OA in which A is an unsubstituted $C_1$-$C_{60}$ alkyl group as described above. Examples of the $C_1$-$C_{60}$ alkoxy group include methoxy, ethoxy, propoxy, isopropyloxy, butoxy, and pentoxy. At least one hydrogen atom of the unsubstituted $C_1$-$C_{60}$ alkoxy group may be substituted with the same substituents as described above in connection with the alkyl group.

The unsubstituted $C_6$-$C_{60}$ aryl group refers to a carbocyclic aromatic system containing at least one ring. Two or more rings may be fused to each other or linked to each other via a single bond. The term 'aryl' refers to an aromatic system, such as phenyl, naphthyl, or anthracenyl. At least one hydrogen atom of the aryl group may be substituted with the same substituents described with reference to the $C_1$-$C_{60}$ alkyl group.

Examples of the substituted or unsubstituted $C_6$-$C_{60}$ aryl group include a phenyl group, a $C_1$-$C_{10}$ alkylphenyl group (for example, ethylphenyl group), a halophenyl group (for example, o-, m-, and p-fluorophenyl group, and dichlorophenyl group), a cyanophenyl group, a dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, an o-, m-, and p-toryl group, an o-, m-, and p-cumenyl group, a mesityl group, a phenoxyphenyl group, an (α,α-dimethylbenzene) phenyl group, an (N,N'-dimethyl)aminophenyl group, an (N,N'-diphenyl)aminophenyl group, a pentalenyl group, an indenyl group, a naphthyl group, a halonaphthyl group (for example, fluoronaphthyl group), a $C_1$-$C_{10}$ alkylnaphthyl group (for example, methylnaphthyl group), a $C_1$-$C_{10}$ alkoxynaphthyl group (for example, methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_1$-$C_{60}$ heteroaryl group includes one, two or three hetero atoms selected from the group consisting of N, O, P and S. Two or more rings may be fused to each other or linked to each other via a single bond. Examples of the unsubstituted $C_1$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. At least one hydrogen atom of the heteroaryl group may be substituted with the same substituents described with reference to the $C_1$-$C_{60}$ alkyl group.

The unsubstituted $C_6$-$C_{60}$ aryloxy group refers to a group represented by —$OA_1$, in which $A_1$ is a $C_6$-$C_{60}$ aryl group. Examples of the aryloxy group include a phenoxy group. At least one hydrogen atom of the aryloxy group may be substituted with the same substituents described with reference to the $C_1$-$C_{60}$ alkyl group.

The unsubstituted $C_6$-$C_{60}$ arylthio group refers to a group represented by —$SA_1$, in which $A_1$ is a $C_6$-$C_{60}$ aryl group. Examples of the arylthio group include a benzenethio group and a naphthylthio group. At least one hydrogen atom of the arylthio group may be substituted with the same substituents described with reference to the $C_1$-$C_{60}$ alkyl group.

The unsubstituted $C_6$-$C_{60}$ condensed polycyclic group is a substituent including at least two rings in which at least one aromatic ring and at least one non-aromatic ring are fused to each other or a substituent including an unsaturated ring without having a conjugation structure. The condensed polycyclic group is distinguished from the aryl group or heteroaryl group since the condensed polycyclic group does not have an orientation.

Examples of the heterocyclic compound of Formula 1 according to an embodiment may include the following formulae without being limited thereto.

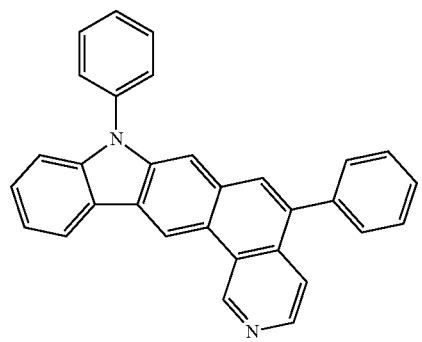

1

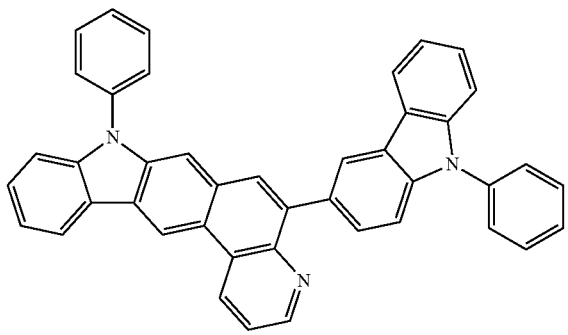

2

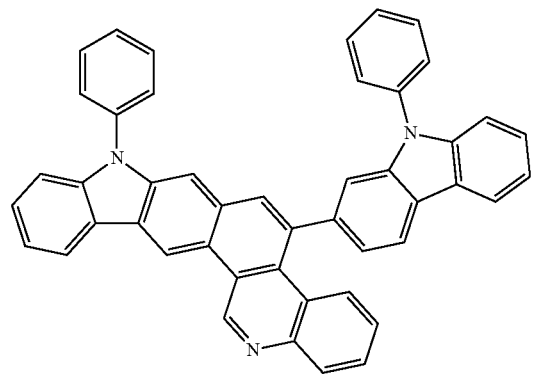

3

-continued

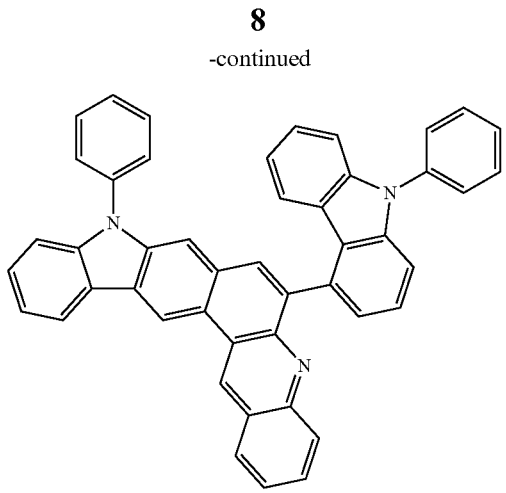

4

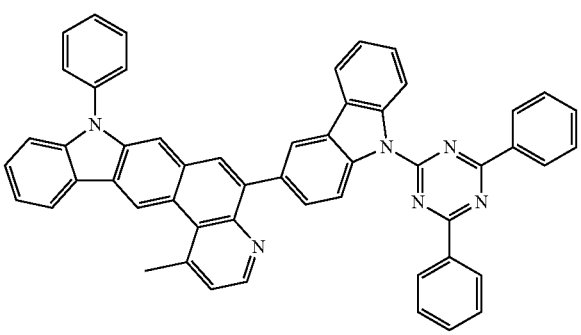

5

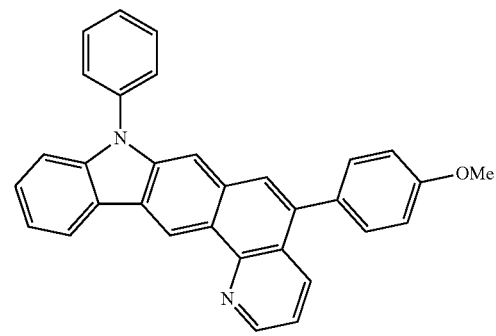

6

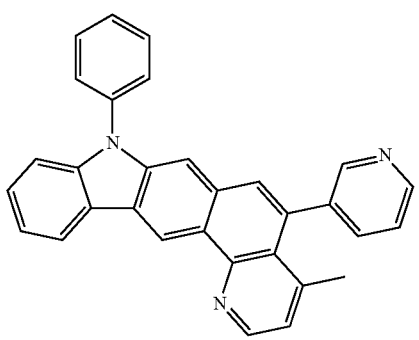

7

-continued
8
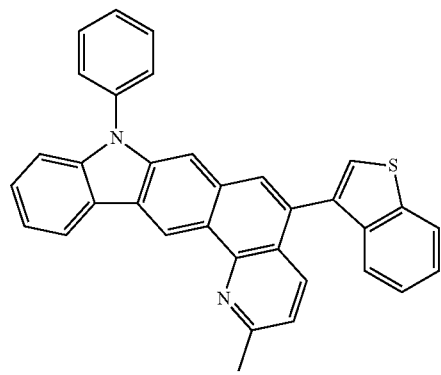
9
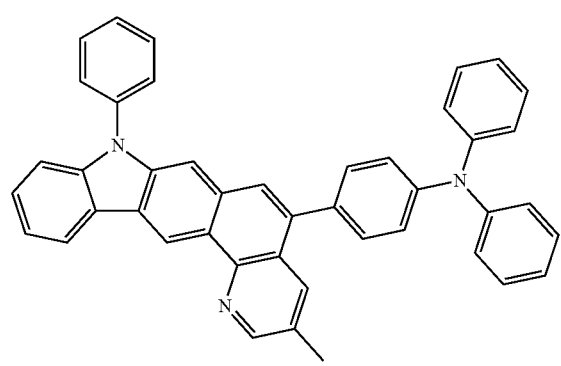
10
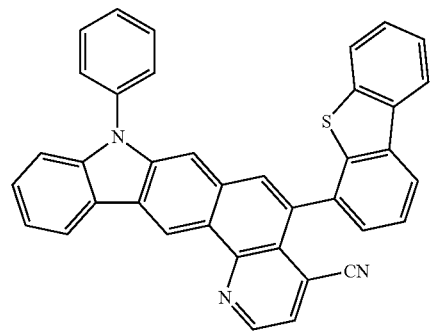
11
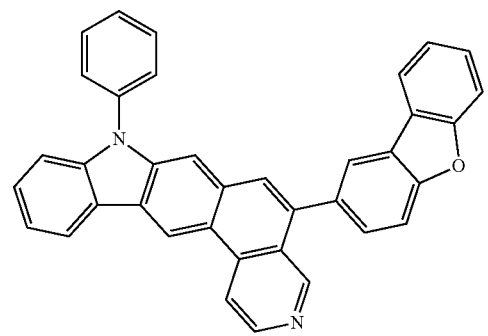
-continued
12
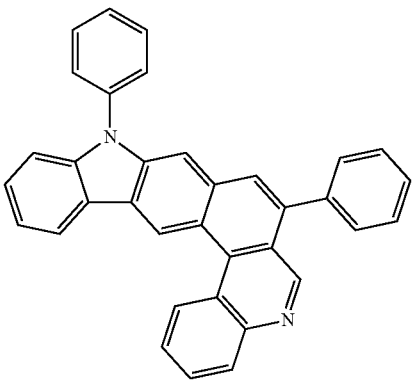
13
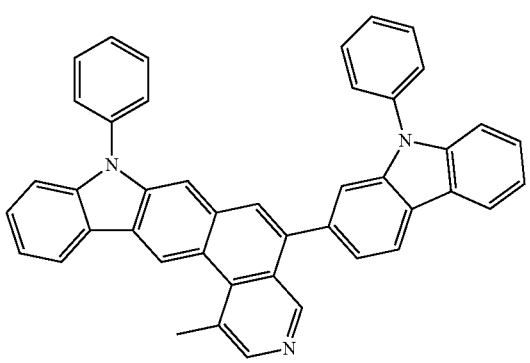
14
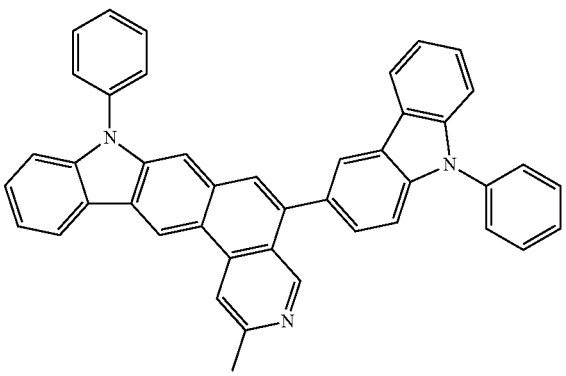
15
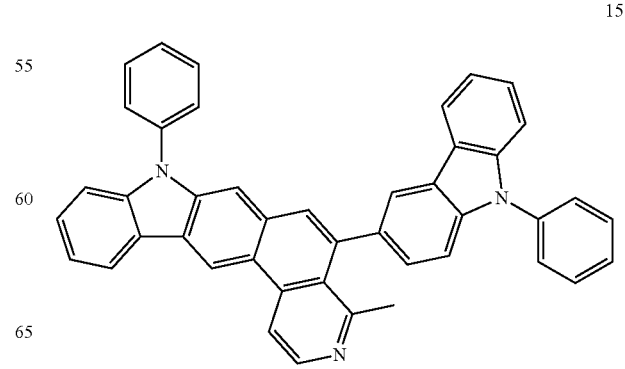

-continued
16
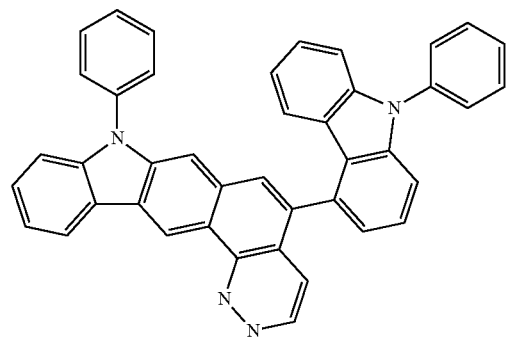
17
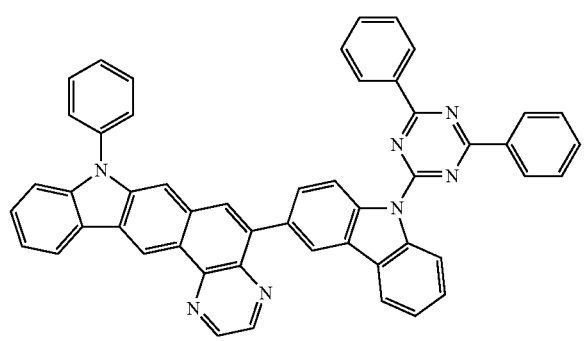
18
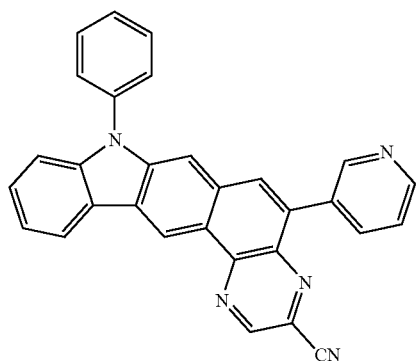
19
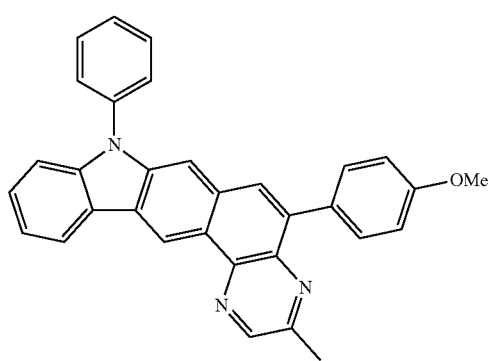
-continued
20
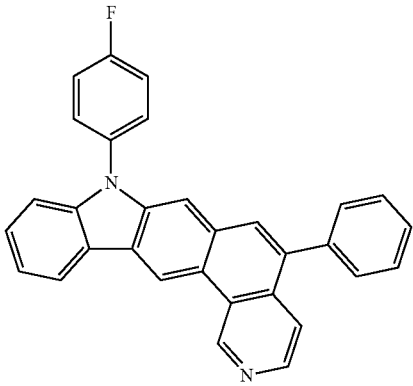
21
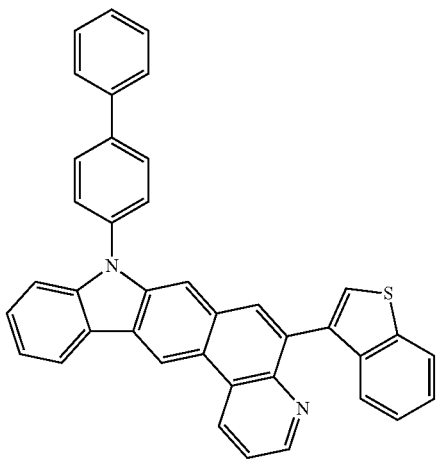
22
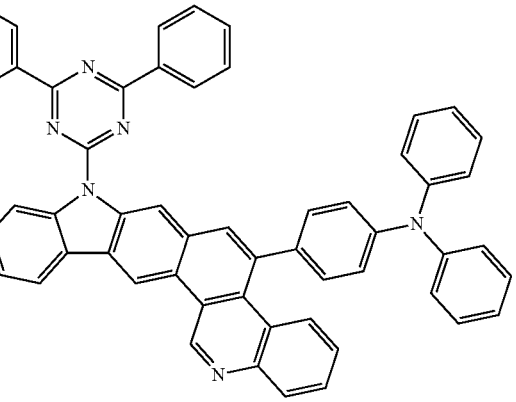

23
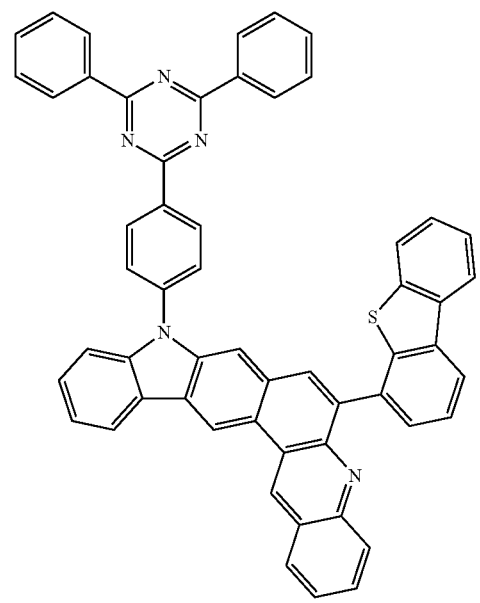
24
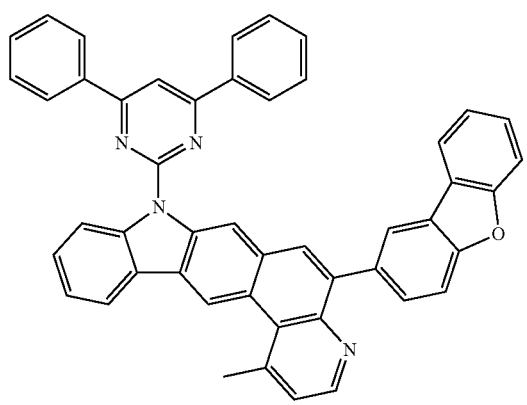
25
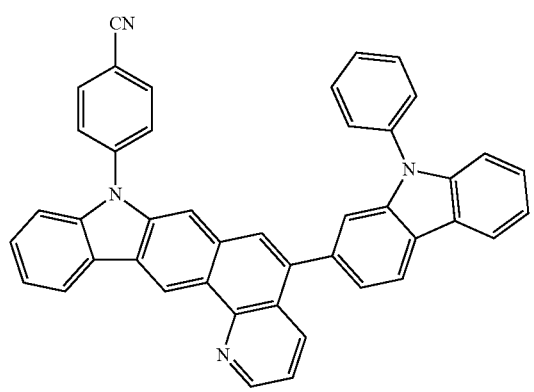
26
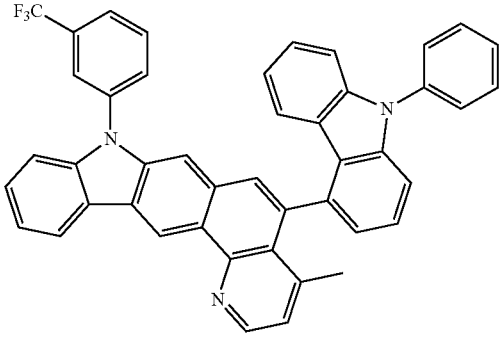
27
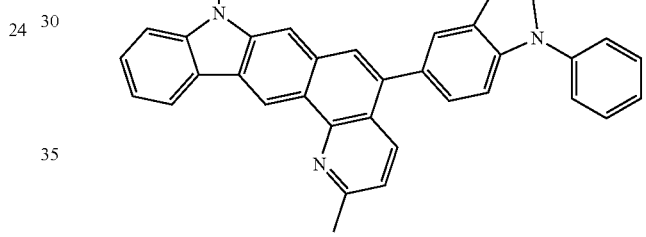
28
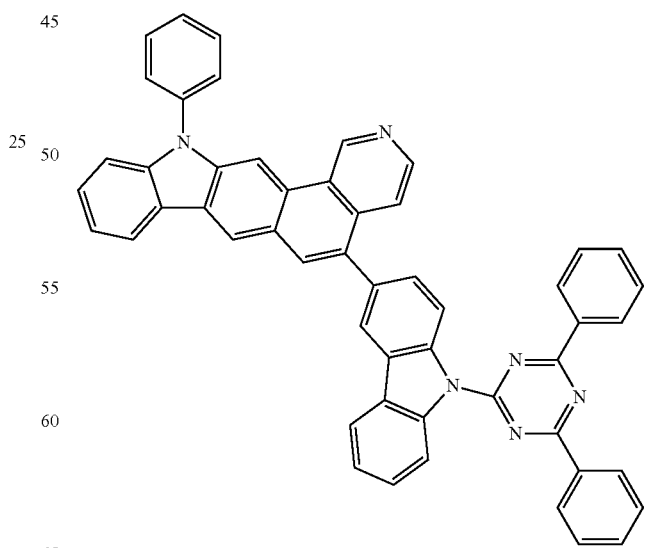

29
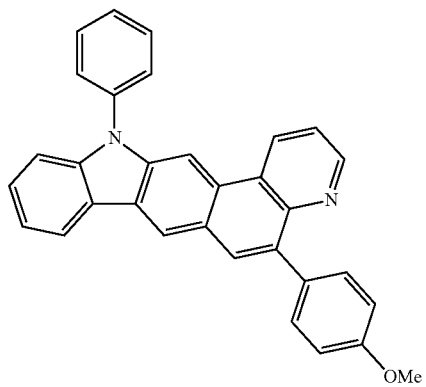
30
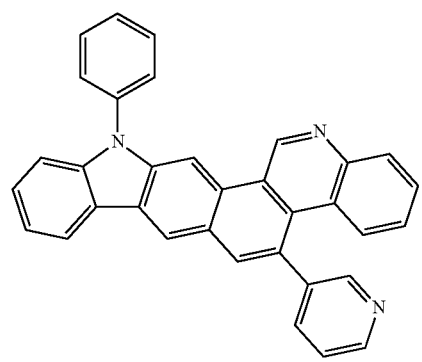
31
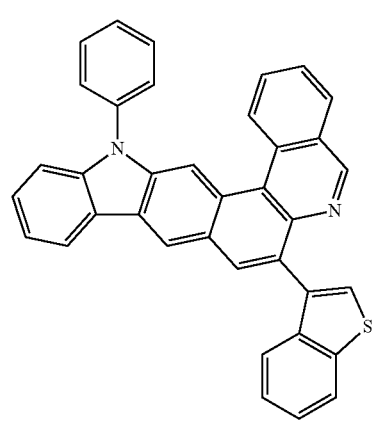
32
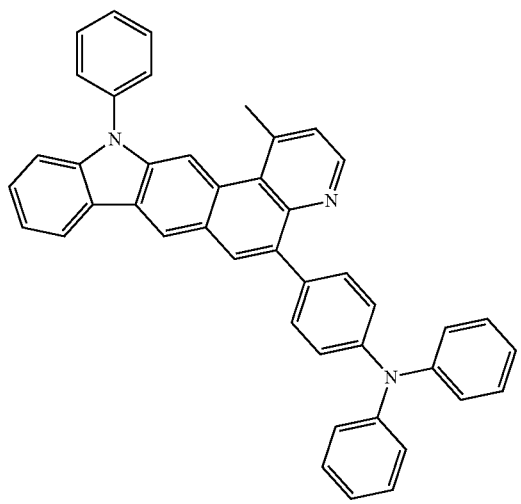
33
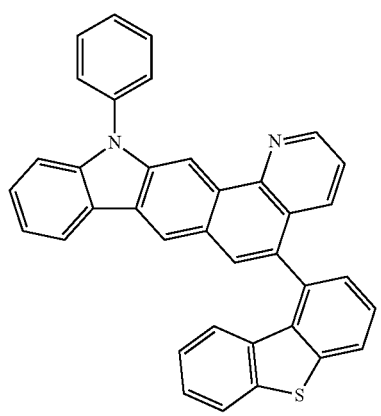
34
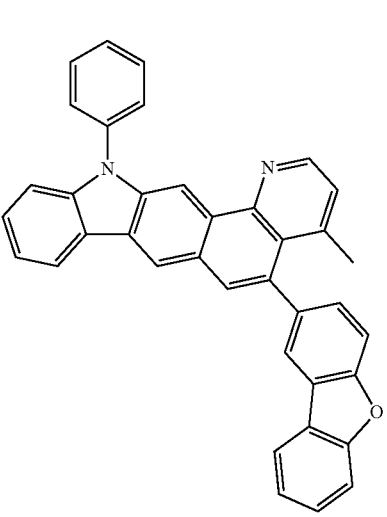

35
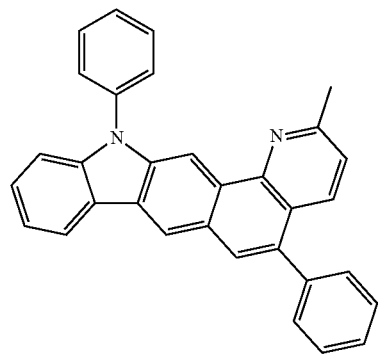
36
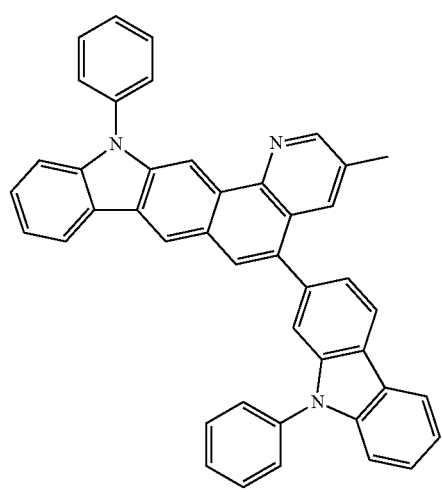
37
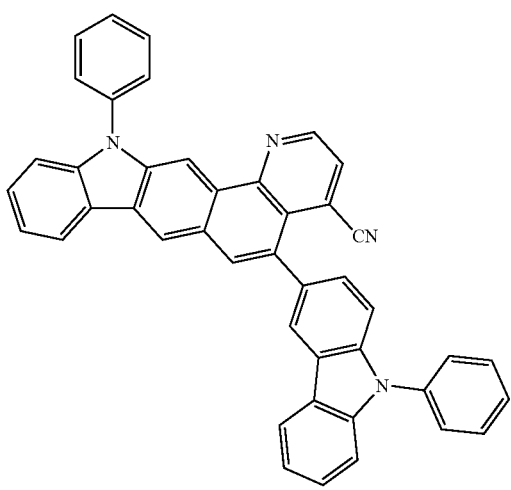
38
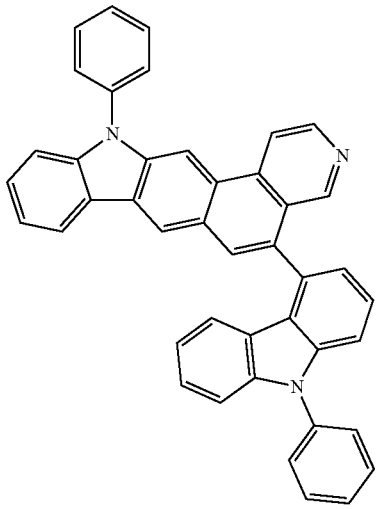
39
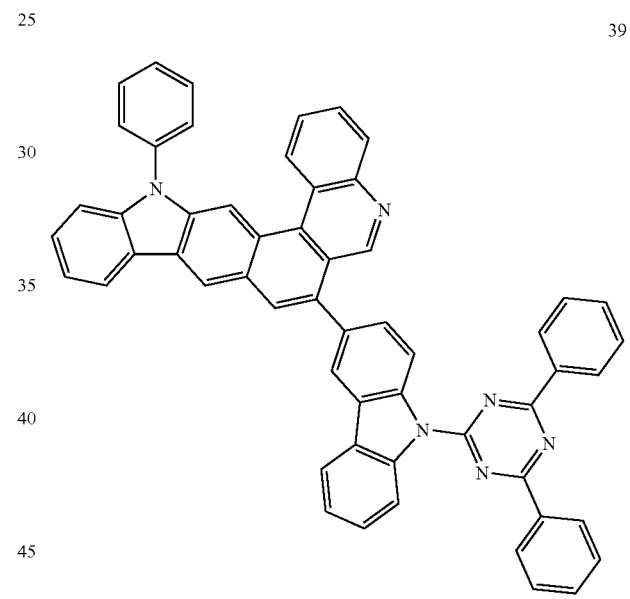
40
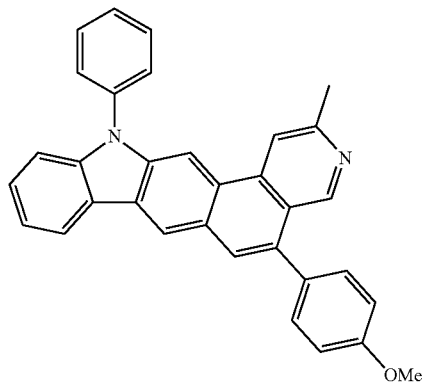

41
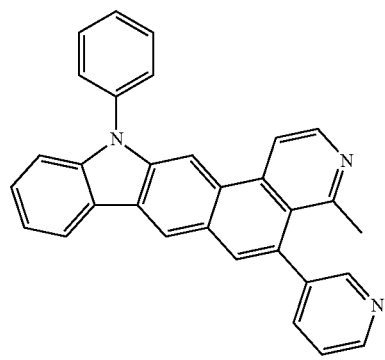
42
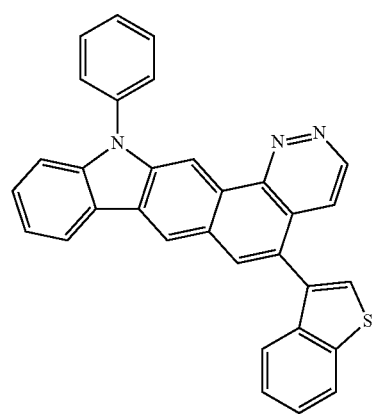
43
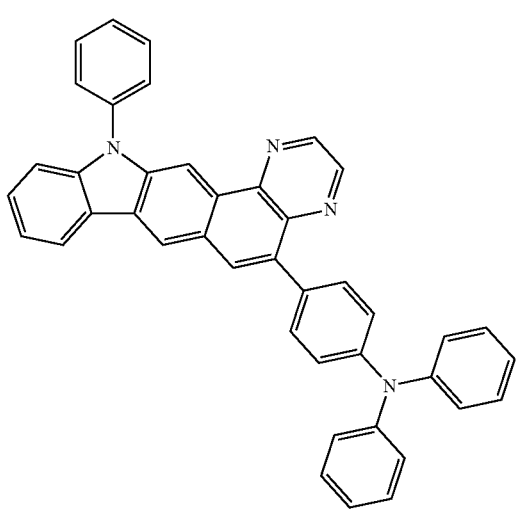
44
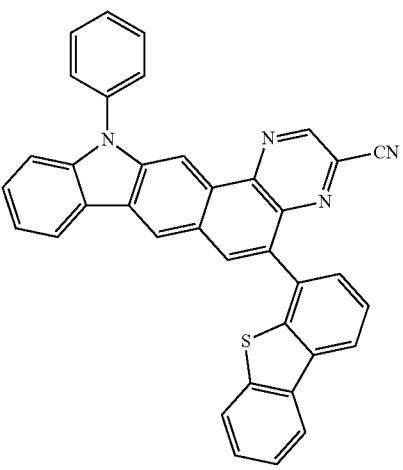
45
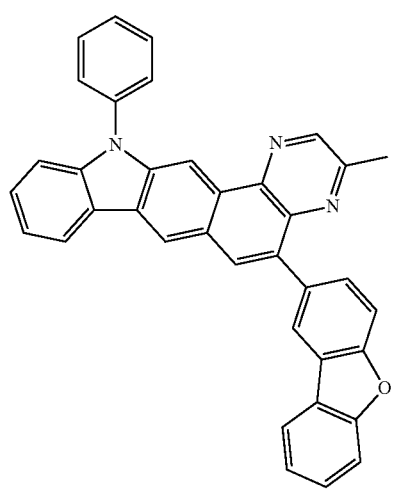
46
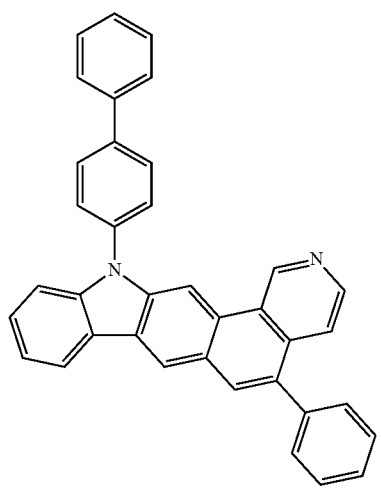

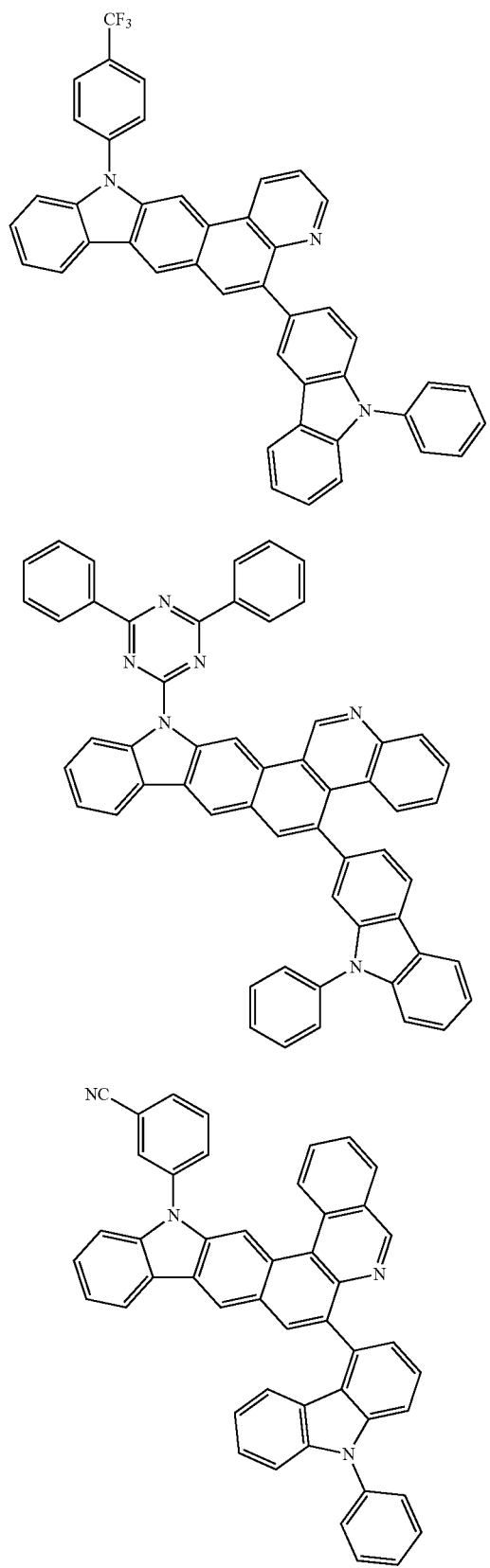
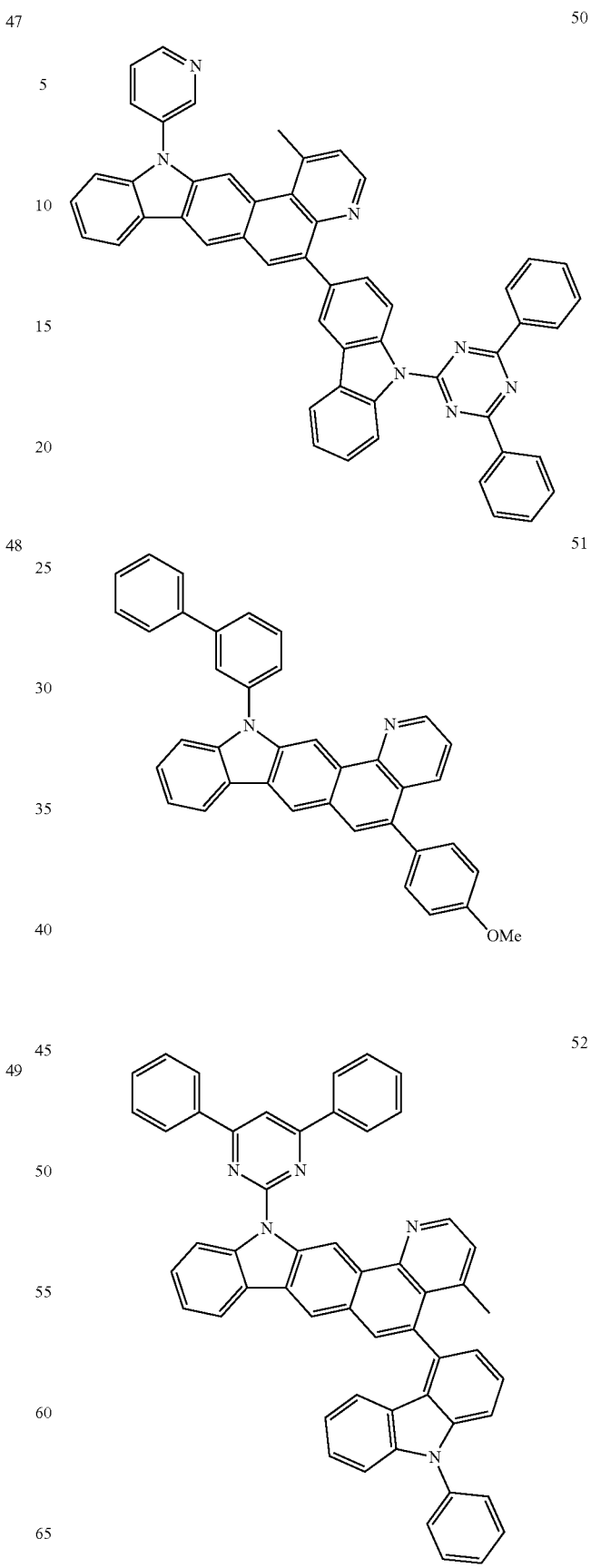

-continued

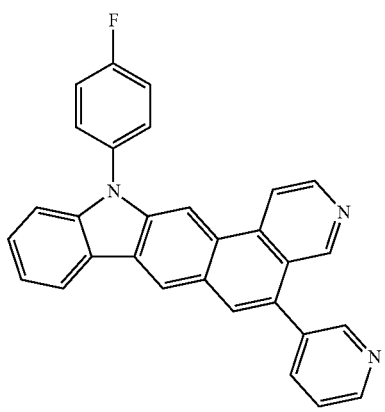

An organic light-emitting device according to another embodiment includes: a first electrode; a second electrode; and an organic layer interposed between the first electrode and the second electrode, wherein the organic layer includes a heterocyclic compound represented by Formula 1 described above.

The organic layer may include at least one layer selected from the group consisting of a hole injection layer (HIL), an HTL, a functional layer having both hole injecting and hole transporting capabilities (H-functional layer), a buffer layer, an electron blocking layer (EBL), an EML, a hole blocking layer (HBL), an ETL, an electron injection layer (EIL), and a functional layer having both electron injecting and electron transporting capabilities (E-functional layer).

More particularly, the organic layer may be an EML, such as, a green EML or a red EML, and the heterocyclic compound may be used as a phosphorescent host. Alternatively, the organic layer may be an ETL or an HTL, and the heterocyclic compound may be used as an electron transporting material or a hole transporting material.

According to an embodiment, the organic light-emitting device may include an EML, an HIL, an HTL, or an H-functional layer. The EML, the HIL, the HTL, or the H-functional layer may include the heterocyclic compound, and the EML may include an anthracene-based compound, an arylamine-based compound, or a styryl-based compound.

According to another embodiment, the organic light-emitting device may include an EML, an HIL, an HTL, or an H-functional layer, and the EML, the HIL, the HTL, or H-functional layer may include the heterocyclic compound. One of a red layer, a green layer, a blue layer, and a white layer of the EML may include a phosphorescent compound. The HIL, the HTL, or the H-functional layer may include a charge-generating material. Meanwhile, the charge-generating material may be a p-dopant. The p-dopant may be a quinone derivative, a metal oxide, or a cyano group-containing compound.

According to another embodiment, the organic layer may include an ETL that includes an electron transporting organic material and a metal complex. The metal complex may be a Li complex.

The term "organic layer" used herein refers to a single layer and/or a multiple layers interposed between the first and second electrodes of the organic light-emitting device.

The organic layer includes an EML that includes the heterocyclic compound. Alternatively, the organic layer may include at least one of the HIL, the HTL, and the H-functional layer, and at least one of the HIL, the HTL, and the H-functional layer may include the heterocyclic compound.

The heterocyclic compound contained in the EML may function as a fluorescent dopant or a phosphorescent host. For example, the heterocyclic compound may function as a blue fluorescent dopant emitting blue light. The heterocyclic compound contained in the EML may also function as a fluorescent or phosphorescent host emitting red, green, or blue light.

FIG. 1 is a schematic cross-sectional view of an organic light-emitting device according to an embodiment. Hereinafter, a structure of the organic light-emitting device according to an embodiment and a method of fabricating the organic light-emitting device will be described with reference to FIG. 1.

A substrate (not shown), which may be any substrate that is commonly used in organic light-emitting devices, may be a glass substrate or a transparent plastic substrate with excellent mechanical strength, thermal stability, transparency, surface smoothness, handling convenience, and waterproofness.

A first electrode may be formed on the substrate by depositing or sputtering a material that is used to form the first electrode. When the first electrode constitutes an anode, the material used to form the first electrode may be a high work function material so as to facilitate hole injection. The first electrode may be a reflective electrode or a transmissive electrode. Transparent and conductive materials such as indium tin oxide (ITO), indium zinc oxide (IZO), tin oxide ($SnO_2$), and zinc oxide (ZnO) may be used to form the first electrode. The first electrode may also be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layered or a multi-layered structure. For example, the first electrode may have a triple-layered structure of ITO/Ag/ITO, but is not limited thereto.

An organic layer is disposed on the first electrode.

The organic layer may include an HIL, an HTL, a buffer layer (not shown), an EML, an ETL, or an EIL.

The HIL may be formed on the first electrode by vacuum deposition, spin coating, casting, Langmuir-Blodgett (LB) deposition, or the like.

When the HIL is formed using vacuum deposition, the deposition conditions may vary according to a compound that is used to form the HIL, and the structure and thermal characteristics of the HIL to be formed. For example, the deposition conditions may include a deposition temperature of 100 to 500° C., a vacuum pressure of $10^{-8}$ to $10^{-3}$ torr, and a deposition rate of about 0.01 to about 100 Å/sec, but are not limited thereto.

When the HIL is formed by spin coating, coating conditions may vary according to a compound that is used to form the HIL, and the structure and thermal characteristics of the HIL to be formed. For example, the coating conditions may include a coating speed of about 2000 rpm to about 5000 rpm, and a temperature of heat treatment about 80° C. to about 200° C. Here, the heat treatment is performed to remove a solvent after coating. However, the coating conditions are not limited thereto.

The HIL may be formed of any known hole injecting material. Examples of the hole injecting material include, but are not limited to, N,N'-diphenyl-N,N'-bis-[4-(phenyl-m-tolyl-amino)-phenyl]-biphenyl-4,4'-diamine (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), and polyaniline)/poly(4-styrenesulfonate (PANI/PSS).

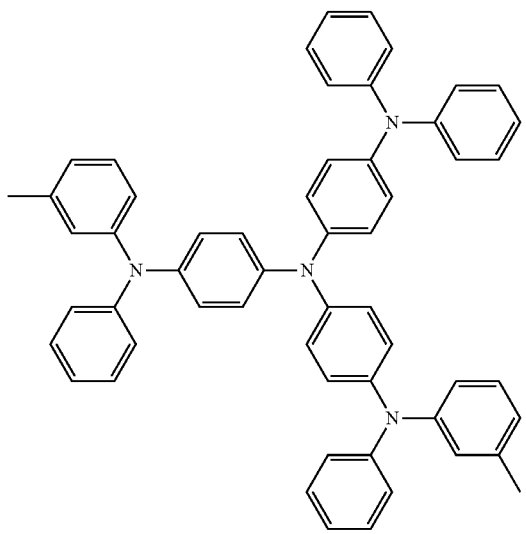

m-MTDATA

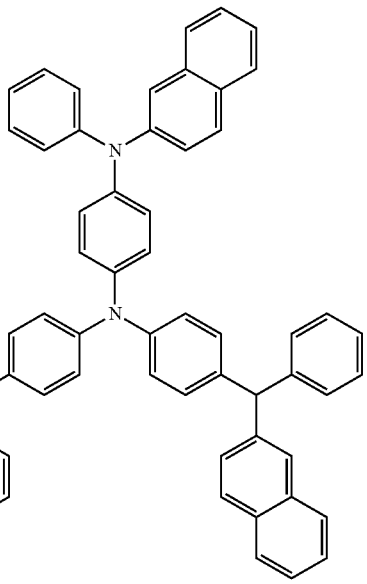

2-TNATA

The thickness of the HIL may be about 100 to about 10,000 Å, for example, about 100 to about 1,000 Å. When the thickness of the HIL is within the range described above, the HIL may have excellent hole injecting ability without a substantial increase in driving voltage.

Then, the HTL may be formed on the HIL by using vacuum deposition, spin coating, casting, LB deposition, or the like. When the HTL is formed by vacuum deposition or spin coating, the conditions for deposition and coating may be similar to those for the formation of the HIL, although the conditions for the deposition and coating may vary according to the material that is used to form the HTL.

The heterocyclic compound according to an embodiment or any known hole transporting material may be used to form the HTL. Examples of the known hole transporting material include a carbazole derivative such as N-phenylcarbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB), but are not limited thereto.

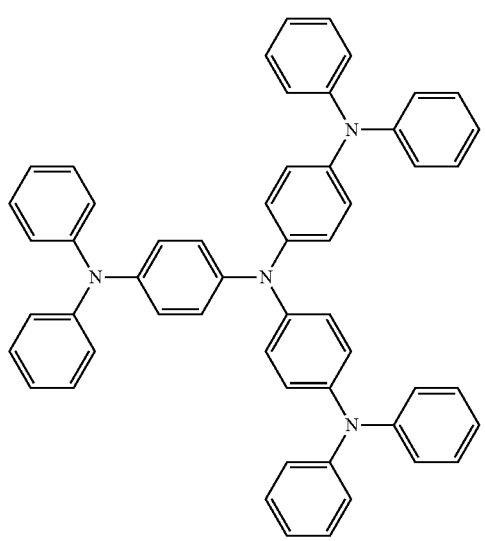

TDATA

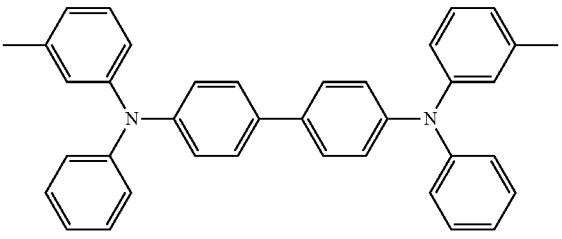

TPD

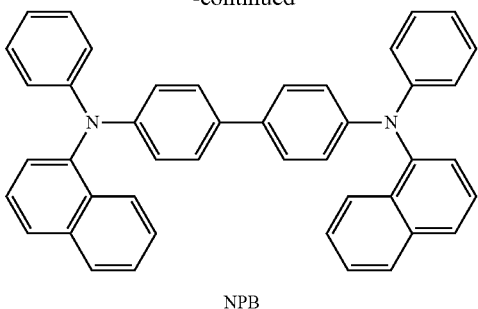

NPB

The thickness of the HTL may be about 50 to about 2,000 Å, for example, about 100 to about 1,500 Å. When the thickness of the HTL is within the range described above, the HTL may have excellent hole transporting ability without a substantial increase in driving voltage.

The H-functional layer may include at least one of the hole injecting materials and hole transporting materials as described above, and the thickness of the H-functional layer may be in the range of about 500 □ to about 10,000 □, for example, about 100 □ to about 1,000 □. When the thickness of the H-functional layer is within the range described above, the H-functional layer may have excellent hole injecting and transporting abilities without a substantial increase in driving voltage.

Meanwhile, at least one of the HIL, HTL, and the H-functional layer may include at least one of the compounds represented by Formulae 300 and 350 below.

Formula 300

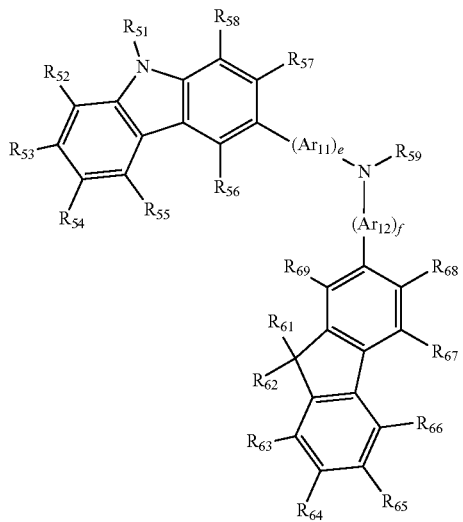

Formula 350

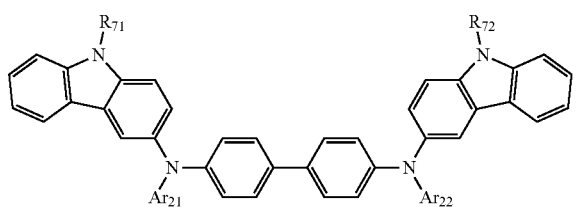

In Formulae 300 and 350, $Ar_{11}$, $Ar_{12}$, $Ar_{21}$, and $Ar_{22}$ are each independently a substituted or unsubstituted $C_5$-$C_{60}$ arylene group.

In Formula 300, e and f are each independently an integer from 0 to 5, for example, 0, 1, or 2. For example, e may be 1, and f may be 0, without being limited thereto.

In Formulae 300 and 350, $R_{51}$ to $R_{58}$, $R_{61}$ to $R_{69}$ and $R_{71}$ and $R_{72}$ may be each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$ and $R_{71}$ and $R_{72}$ may be each independently selected from the group consisting of: a hydrogen atom; a deuterium atom; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group (e.g., a methyl group, an ethyl group, a propyl group, a butyl group, a pentyl group, and a hexyl group); a $C_1$-$C_{10}$ alkoxy group (e.g., a methoxy group, an ethoxy group, a propoxy group, a butoxy group, and a pentoxy group); a $C_1$-$C_{10}$ alkyl group and a $C_1$-$C_{10}$ alkoxy group substituted with at least one selected from the group consisting of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group substituted with at least one selected from the group consisting of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group, without being limited thereto.

In Formula 300, $R_{59}$ may be selected from the group consisting of: a phenyl group; a naphthyl group; an anthryl group; a biphenyl group; a pyridyl group; and a phenyl group, a naphthyl group, an anthryl group, a biphenyl group, and a pyridyl group substituted with at least one of a deuterium atom, a halogen atom, a hydroxyl group, a cyano group, a nitro group, an amino group, an amidino group, hydrazine, hydrazone, a carboxyl group of a salt thereof, a sulfonic acid group or a salt thereof, a phosphoric acid or a salt thereof, a substituted or unsubstituted $C_1$-$C_{20}$ alkyl group, and a substituted or unsubstituted $C_1$-$C_{20}$ alkoxy group.

According to an embodiment, the compound of Formula 300 may be represented by Formula 300A below, but is not limited thereto.

Formula 300A
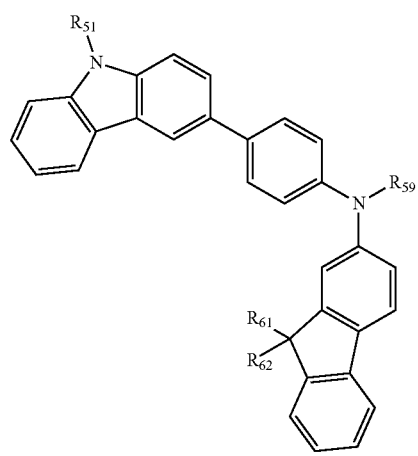
In Formula 300A, $R_{51}$, $R_{62}$, $R_{61}$, and $R_{59}$ are defined as described above.
For example, at least one of the HIL, the HTL, and the H-functional layer may include at least one of Compounds 301 to 320 below, but is not limited thereto:
301
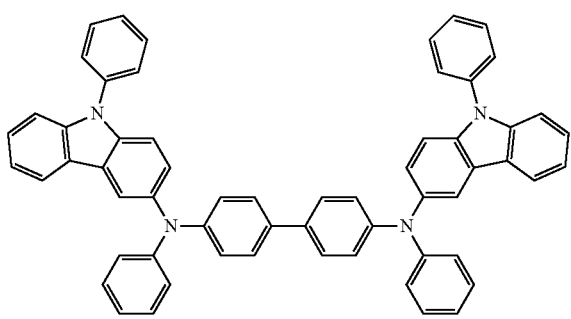
302
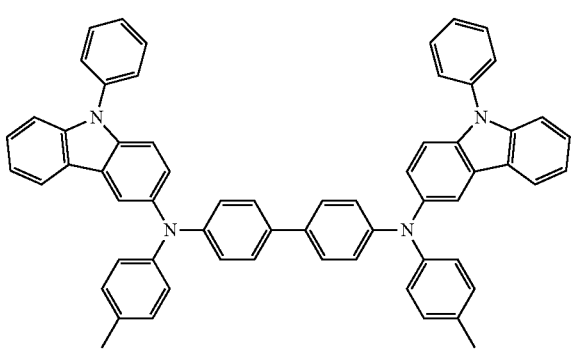
303
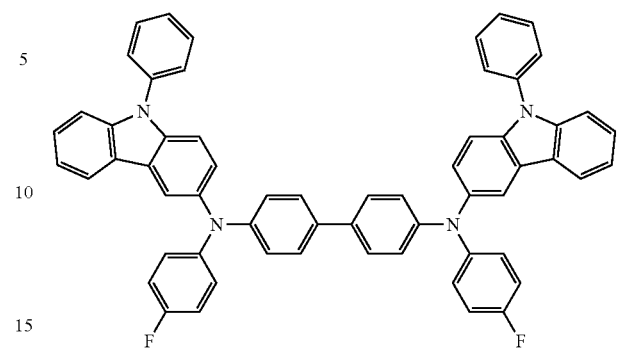
304
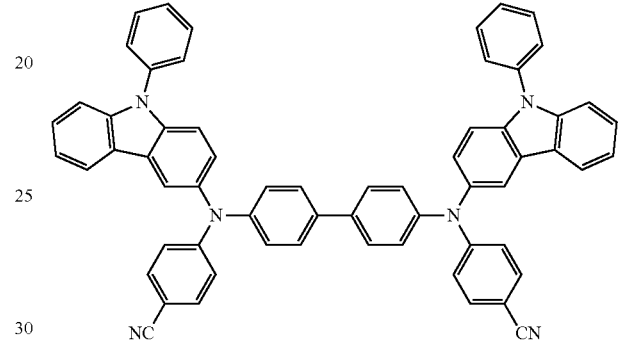
305
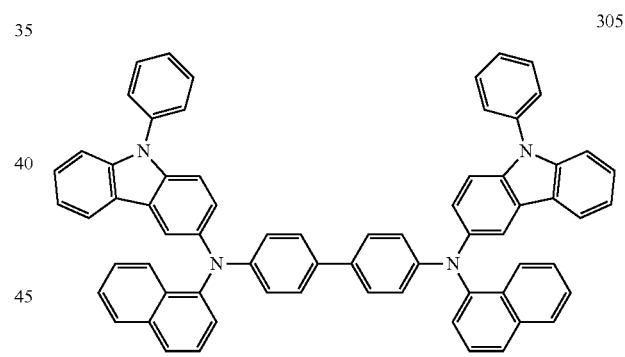
306
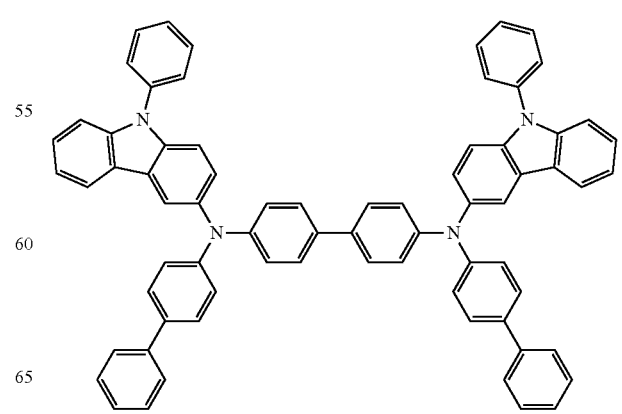

307
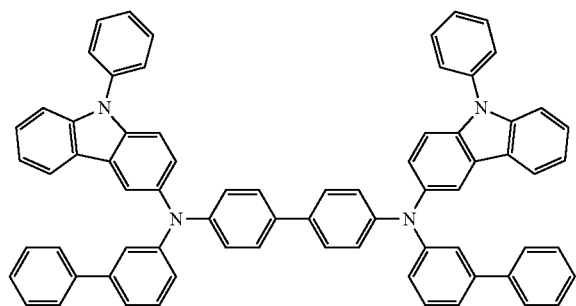
308
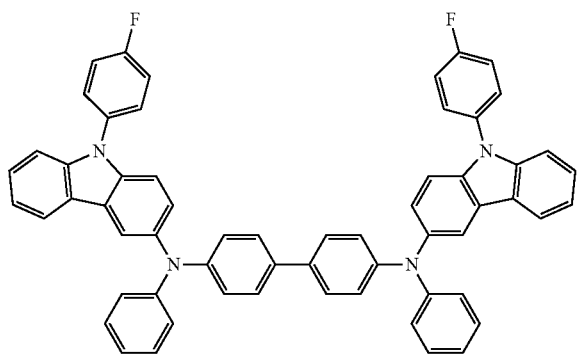
309
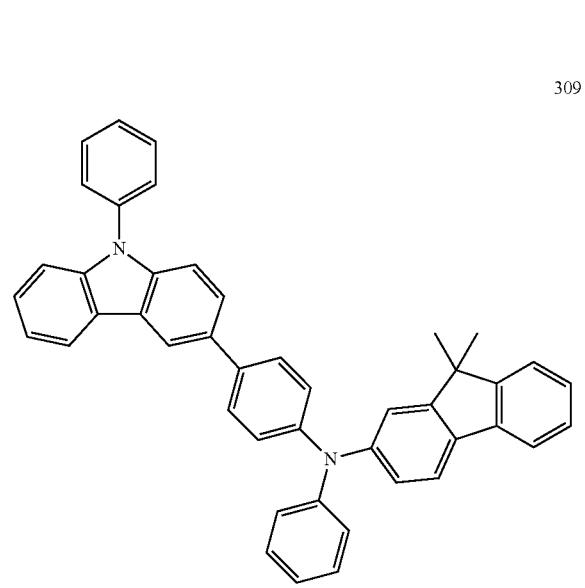
310
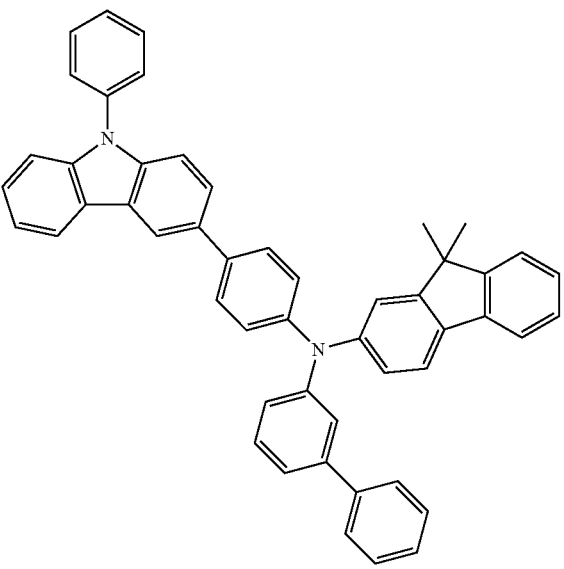
311
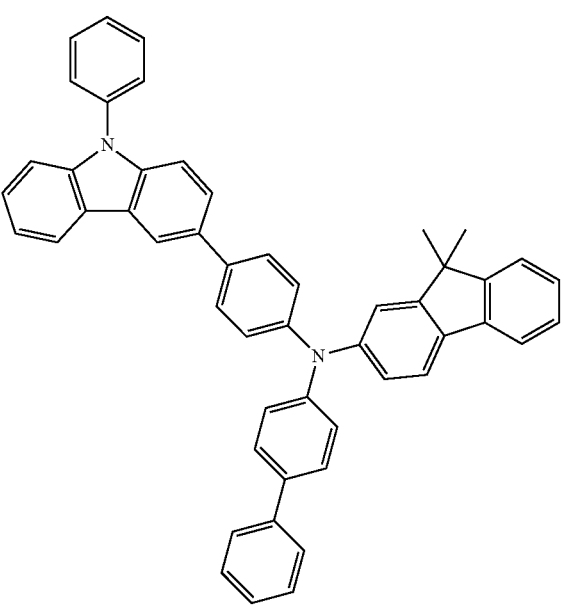

312
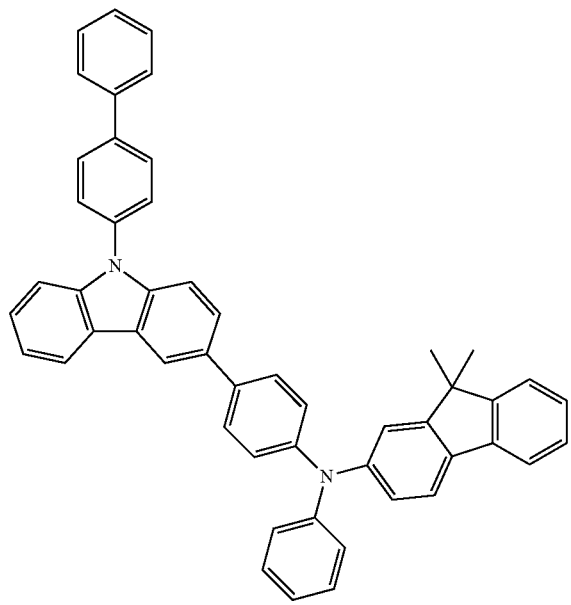
314
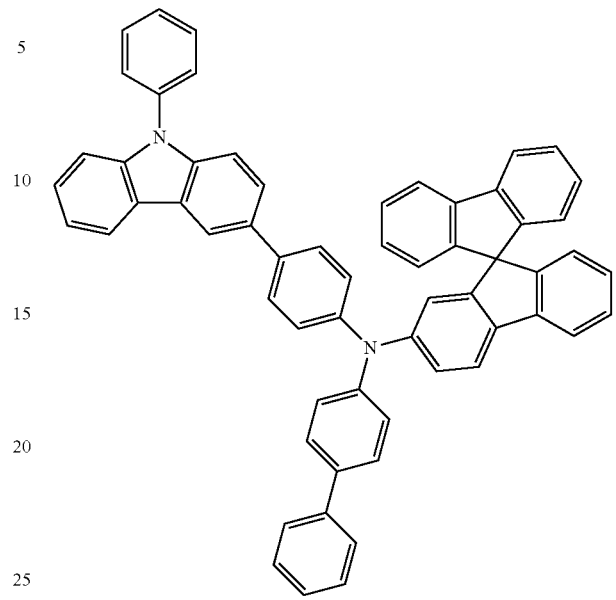
313
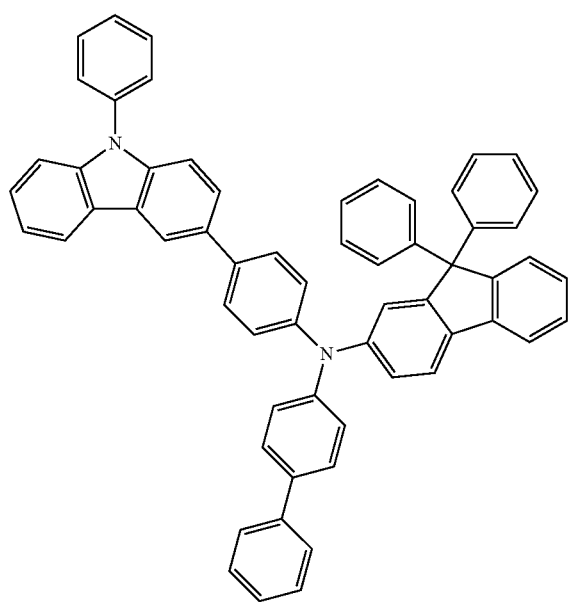
315
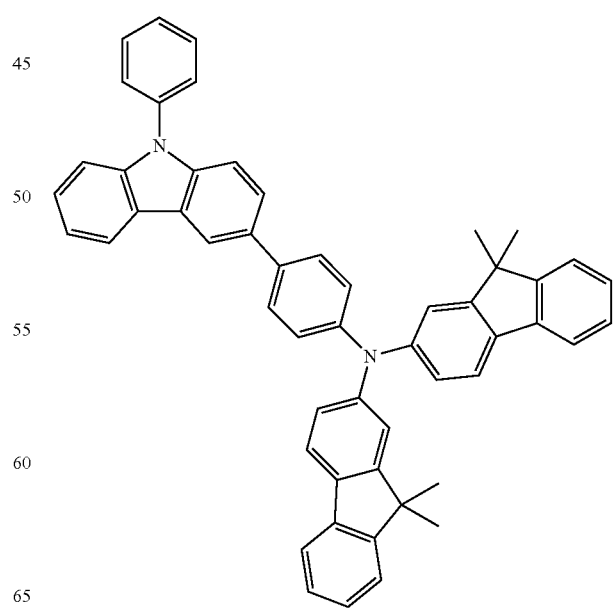

316

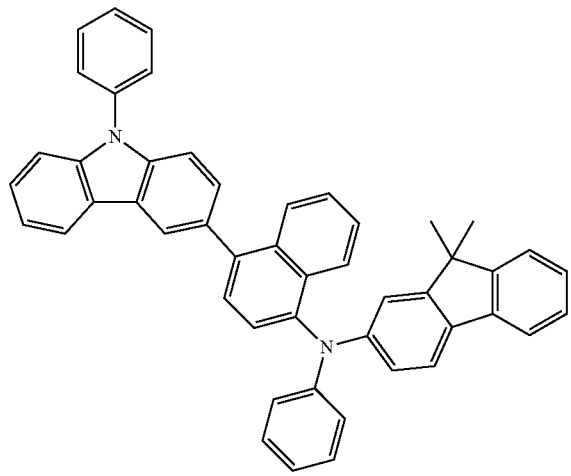

317

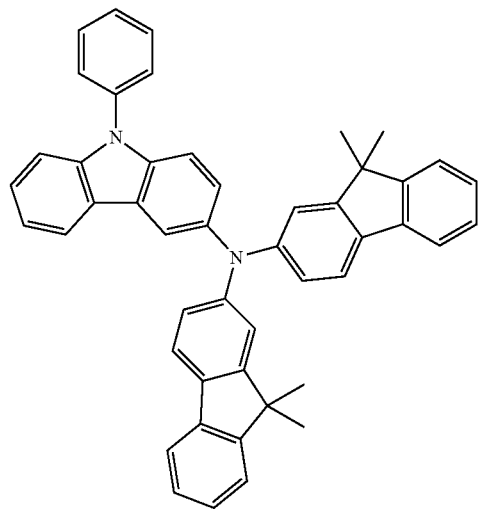

318

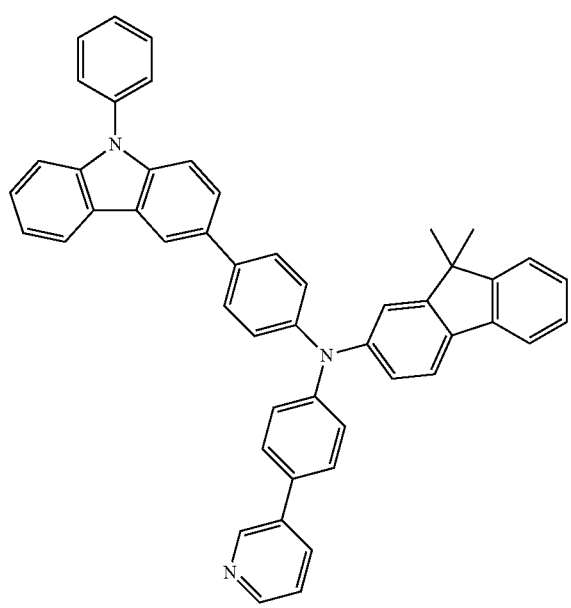

319

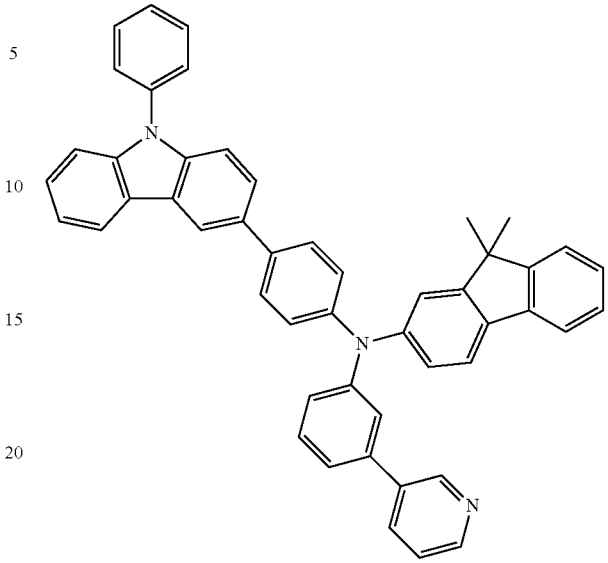

320

At least one of the HIL, the HTL, and the H-functional layer may further include a charge-generating material to improve conductivity of the layers in addition to known hole injecting materials, known hole transporting materials, and/or materials having both hole injecting and hole transporting capabilities.

The charge-generating material may be a p-dopant. The p-dopant may be a quinone derivative, a metal oxide, or a cyano group-containing compound, but is not limited thereto. Examples of the p-dopant include: a quinine derivative such as tetracyanoquinonedimethane (TCNQ) and 2,3,5,6-tetrafluoro-tetracyano-1,4-benzoquinonedimethane (F4-TCNQ); a metal oxide such as tungsten oxide and molybdenum oxide; and a cyano group-containing compound such as that set forth in Formula 200 below, but are not limited thereto.

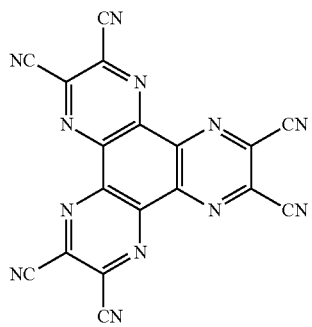

Formula 200

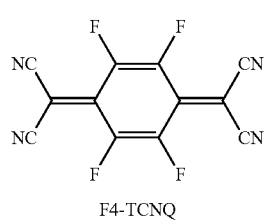

F4-TCNQ

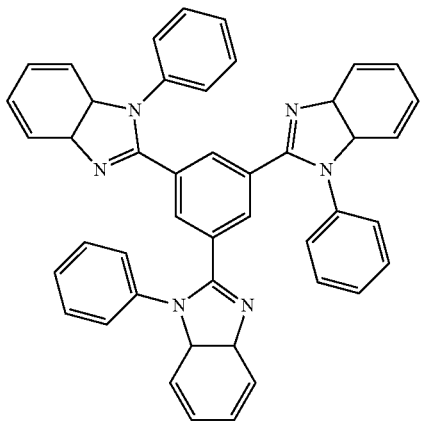

TPBI

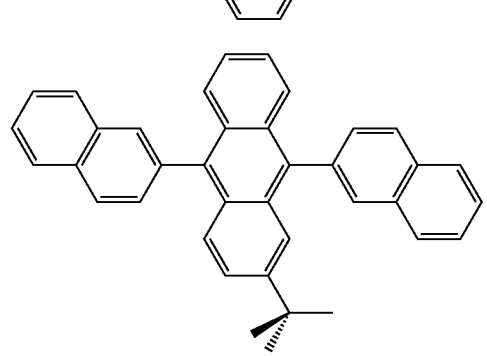

TBADN

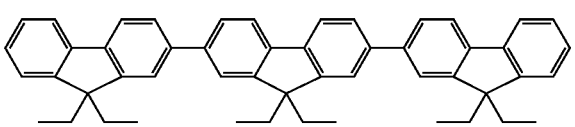

E3

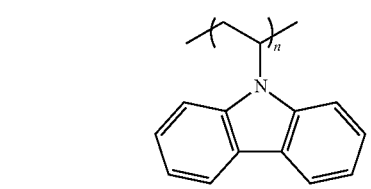

PVK

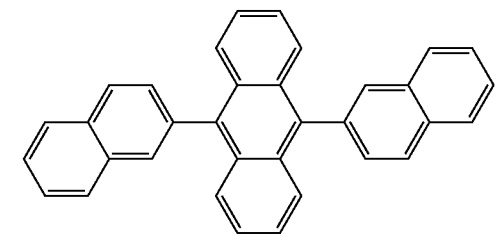

ADN

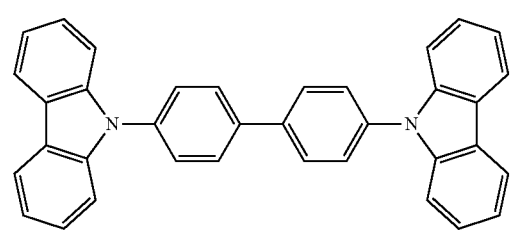

CBP

If the HIL, the HTL, or the H-functional layer further includes the charge-generating material, the charge-generating material may be homogeneously or non-homogeneously dispersed in the HIL, the HTL, or the H-functional layer, or a variety of modifications may be possible.

A buffer layer may be interposed between the EML and at least one of the HIL, the HTL, and the H-functional layer. The buffer layer may increase luminous efficiency by compensating an optical resonant distance according to a wavelength of light emitted from the EML. The buffer layer may include known hole injecting materials and known hole transporting materials. The buffer layer may also include a material that is the same as one of the materials contained in the HIL, the HTL, and the H-functional layer disposed under the buffer layer.

An EML may be formed on the HTL, the H-functional layer, or the buffer layer by vacuum deposition, spin coating, casting, LB deposition, or the like. When the EML is formed by using vacuum deposition or spin coating, the deposition and coating conditions may be similar to those used to form the HIL, although the deposition and coating conditions may vary according to a compound that is used to form the EML.

The EML may include the heterocyclic compound according to an embodiment.

The EML may further include a known host material in addition to the heterocyclic compound.

The host material may include Alq3, 4,4'-N,N'-dicarbazol-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, distyrylarylene (DSA), dmCBP (refer to the following formula), and Compounds 501 to 509 below, but is not limited thereto.

-continued
dmCBP
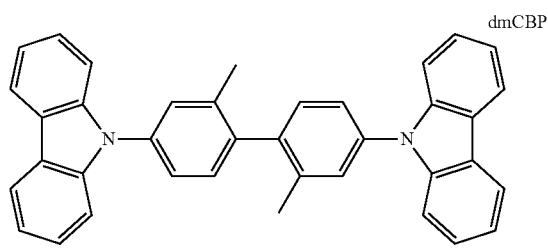
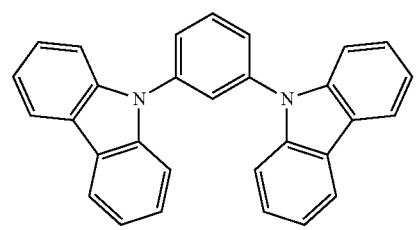
501
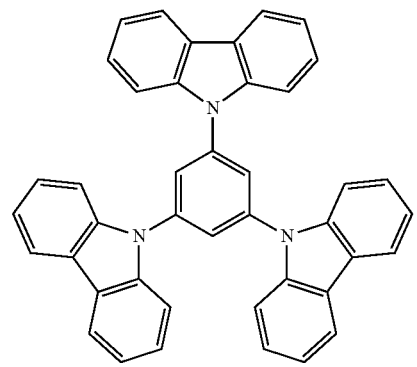
502
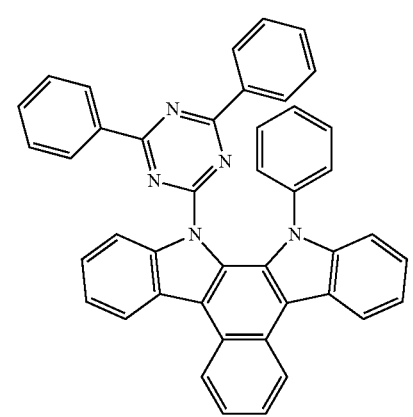
503
-continued
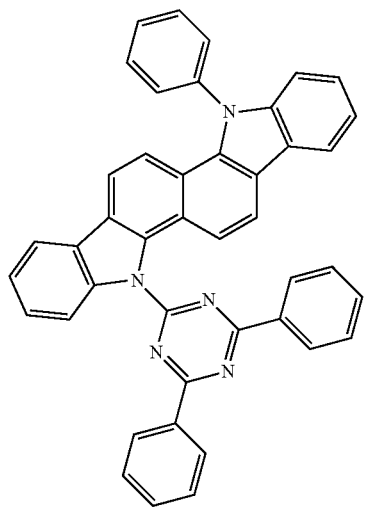
504
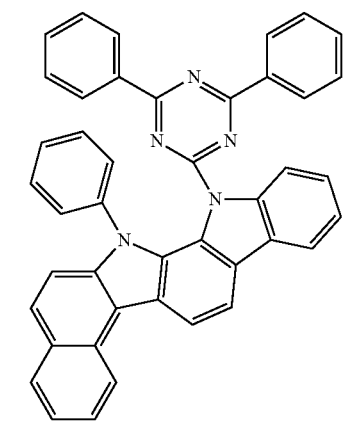
505
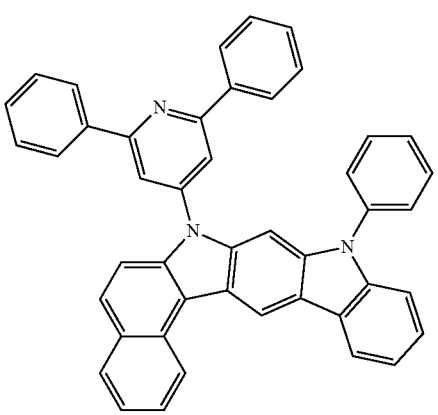
506

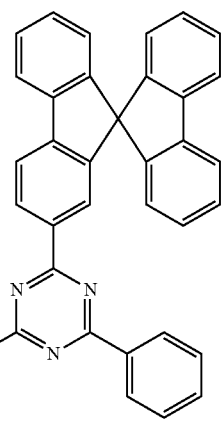

507

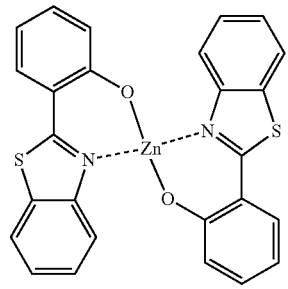

508

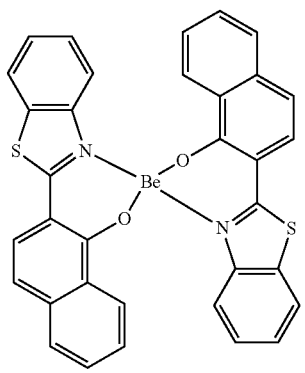

509

Alternatively, the host may be an anthracene-based compound represented by Formula 400 below.

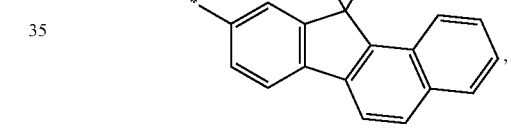

Formula 400

In Formula 400, $Ar_{111}$ and $Ar_{112}$ are each independently a substituted or unsubstituted $C_5$-$C_{60}$ arylene group; $Ar_{113}$ to $Ar_{116}$ are each independently a substituted or unsubstituted $C_1$-$C_{10}$ alkyl group or a substituted or unsubstituted $C_5$-$C_{60}$ aryl group; and g, h, i, and j are each independently an integer from 0 to 4.

For example, in Formula 400, $Ar_{111}$ and $Ar_{112}$ may be a phenylene group, a naphthylene group, a phenanthrenylene group, or a pyrenylene group; or a phenylene group, a naphthylene group, a phenathrenylene group, a fluorenyl group, or a pyrenylene group substituted with at least one selected from the group consisting of a phenyl group, a naphthyl group, and an anthryl group, but are not limited thereto.

In Formula 400, g, h, i, and j are each independently 0, 1, or 2.

In Formula 400, $Ar_{113}$ to $Ar_{116}$ may be each independently selected from the group consisting of: a $C_1$-$C_{10}$ alkyl group substituted with at least one selected from the group consisting of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group substituted with at least one selected from the group consisting of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

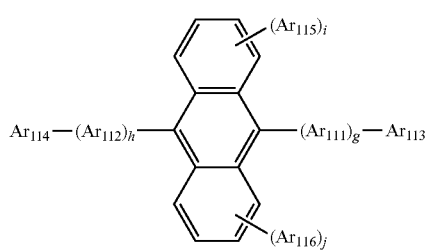

without being limited thereto.

For example, the anthracene-based compound represented by Formula 400 may be one or the following compounds, but is not limited thereto.

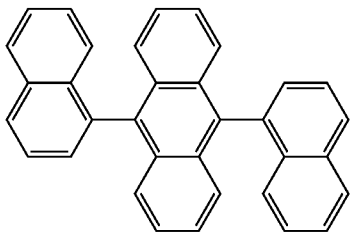

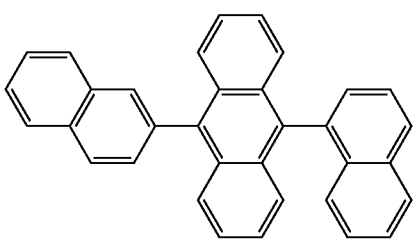

-continued
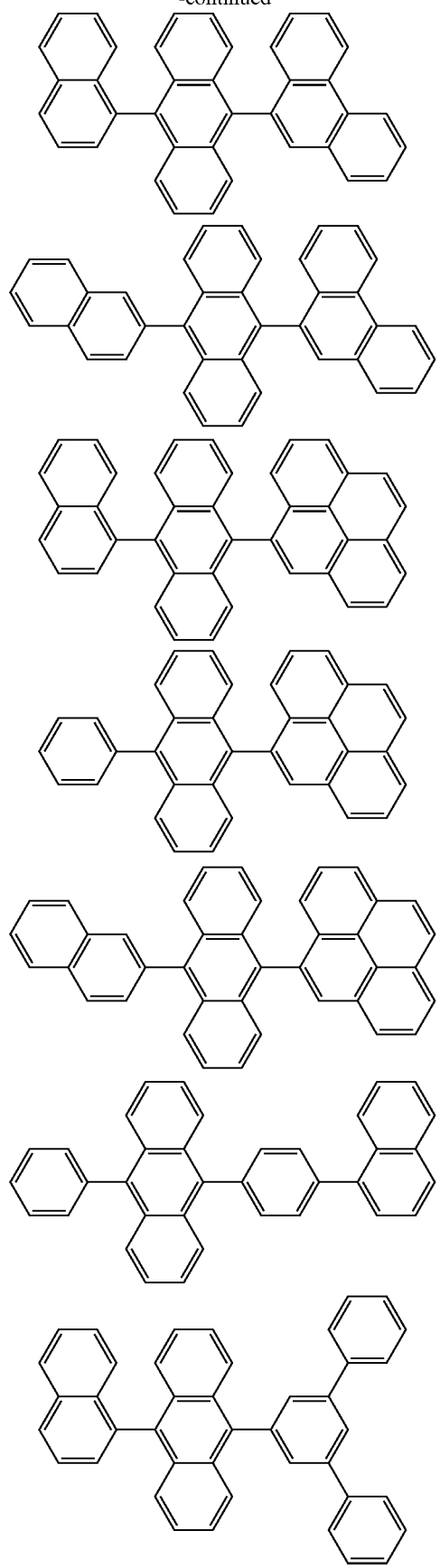
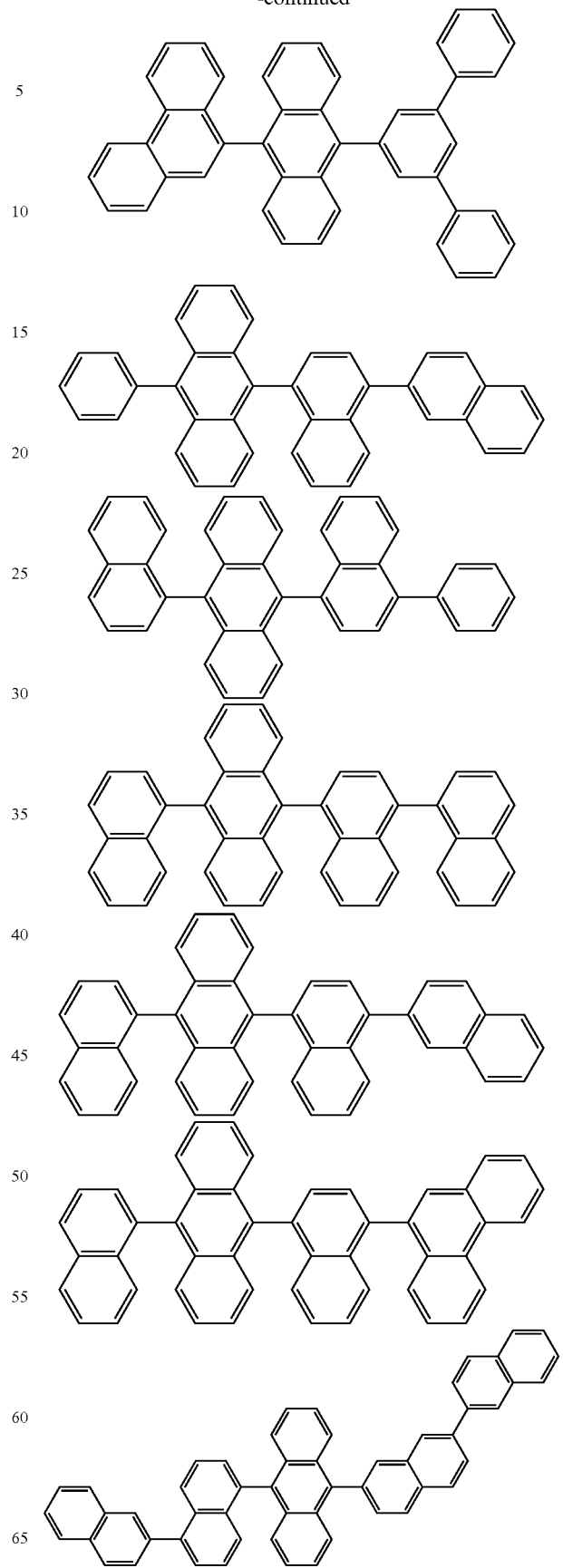

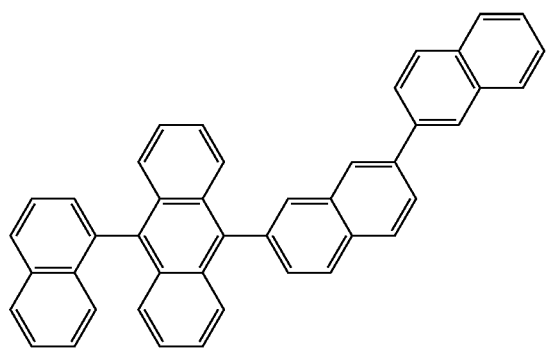
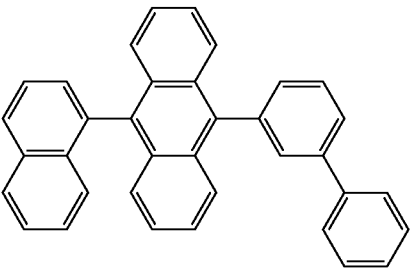
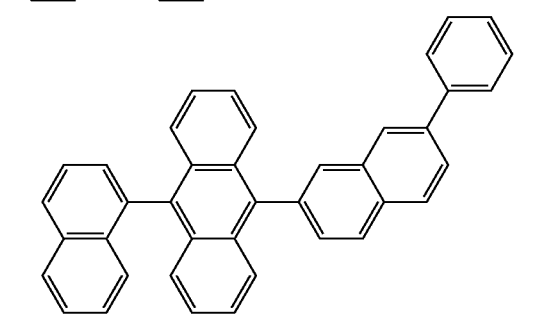
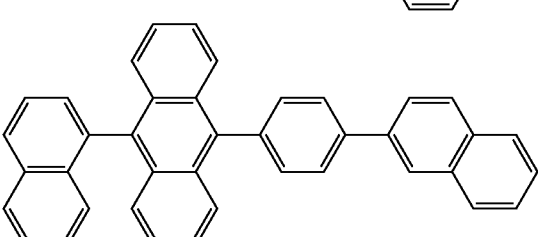
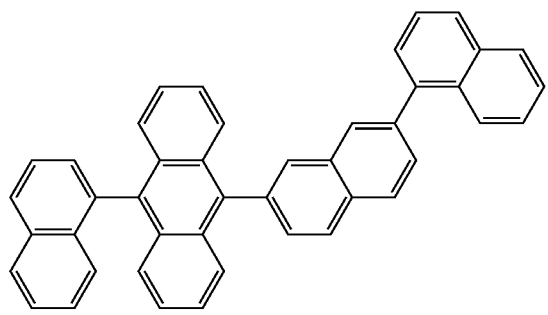
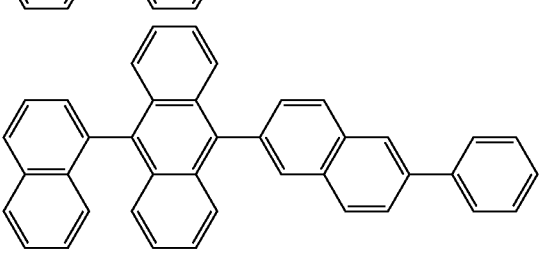
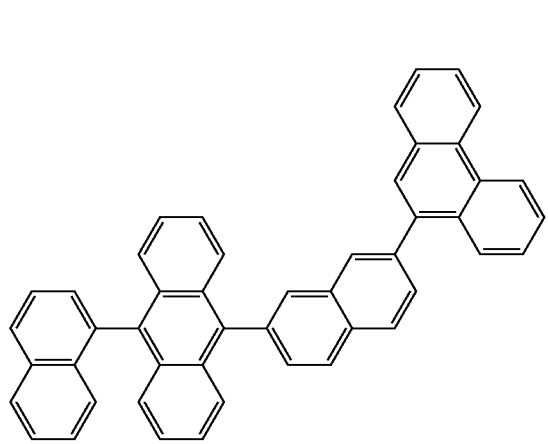
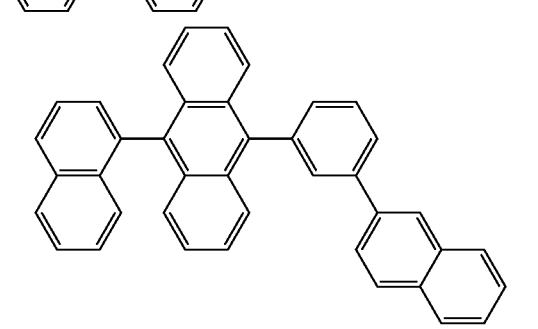
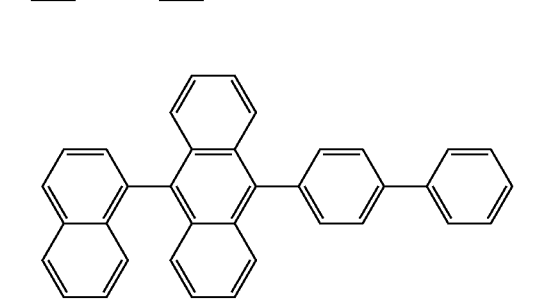
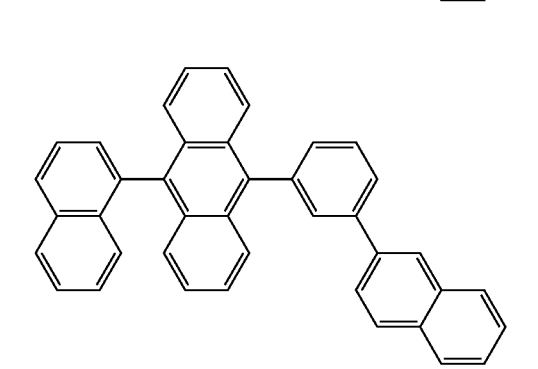
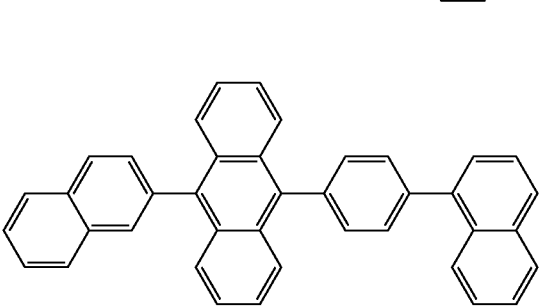

-continued
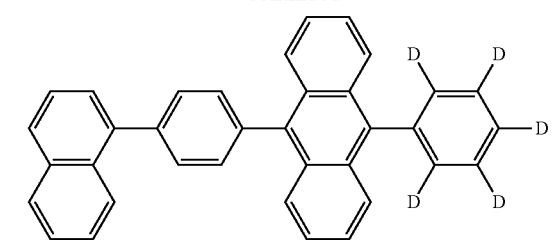
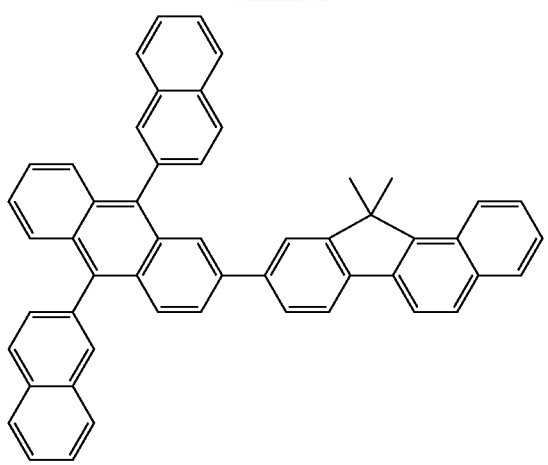
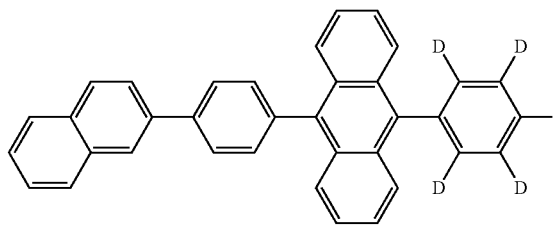
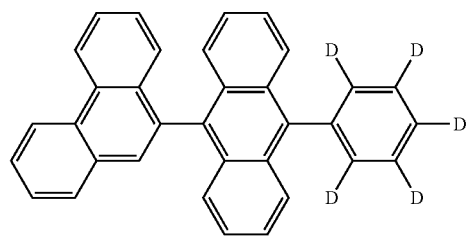
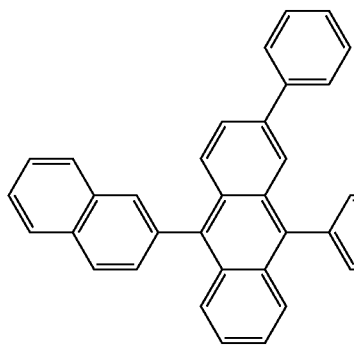
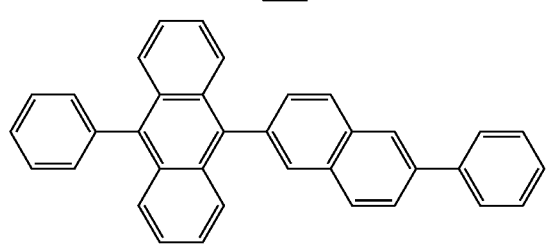
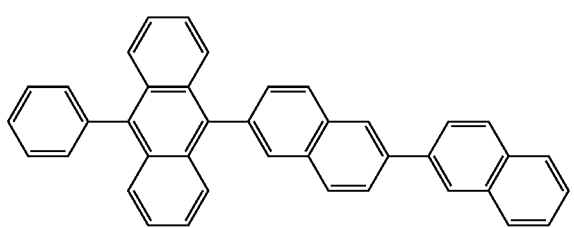
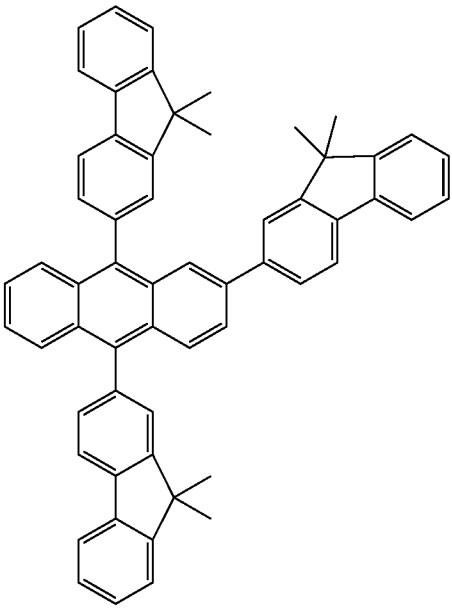

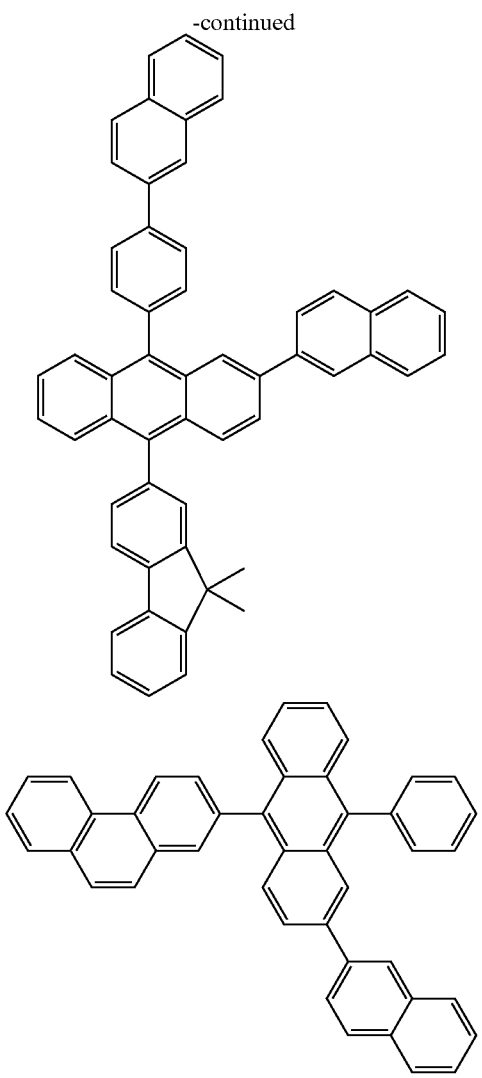

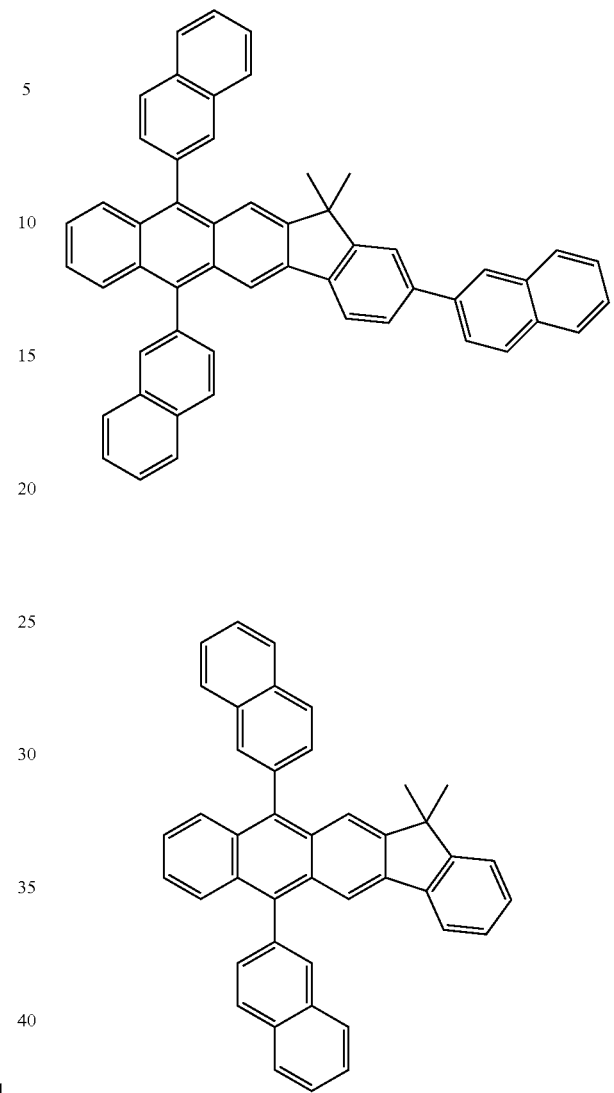

Alternatively, as the host, an anthracene-based compound represented by Formula 401 may be used.

Formula 401

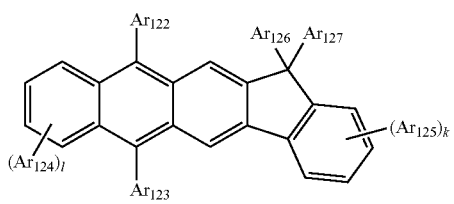

In Formula 401, $Ar_{122}$ to $Ar_{125}$ are defined as described above with reference to $Ar_{113}$ of Formula 400.

In Formula 401, $Ar_{126}$ and $Ar_{127}$ may be each independently a $C_1$-$C_{10}$ alkyl group, such as a methyl group, an ethyl group, or a propyl group.

In Formula 401, k and l may be each independently an integer from 0 to 4. For example, k and l may be 0, 1, or 2, respectively.

For example, the anthracene-based compound represented by Formula 401 may be one of the following compounds, but is not limited thereto.

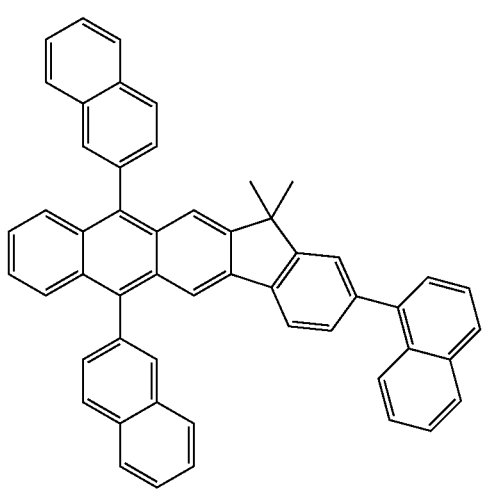

-continued

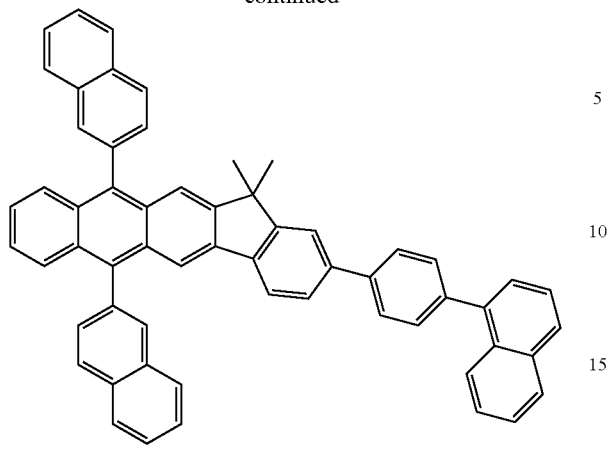

When the organic light-emitting device is a full-color organic light-emitting device, the EML may be patterned to a red EML, a green EML, and a blue EML. In this case, the heterocyclic compound according to an embodiment may be used as a phosphorescent host in a green EML or a red EML.

Meanwhile, at least one of the red, green, and blue EMLs may include the following dopant (ppy=phenylpyridine).

For example, as a blue dopant, the following compounds, in addition to the heterocyclic compound according to an embodiment, may be used without being limited thereto.

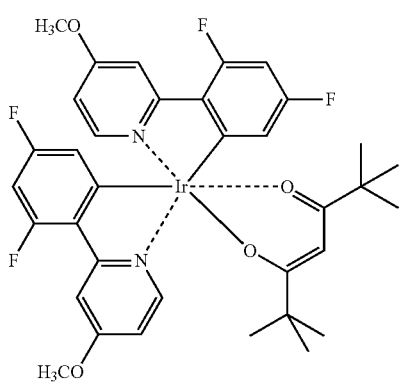

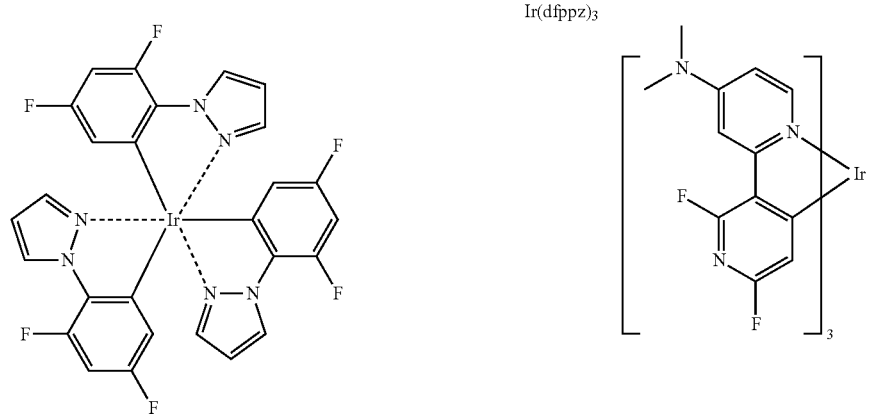

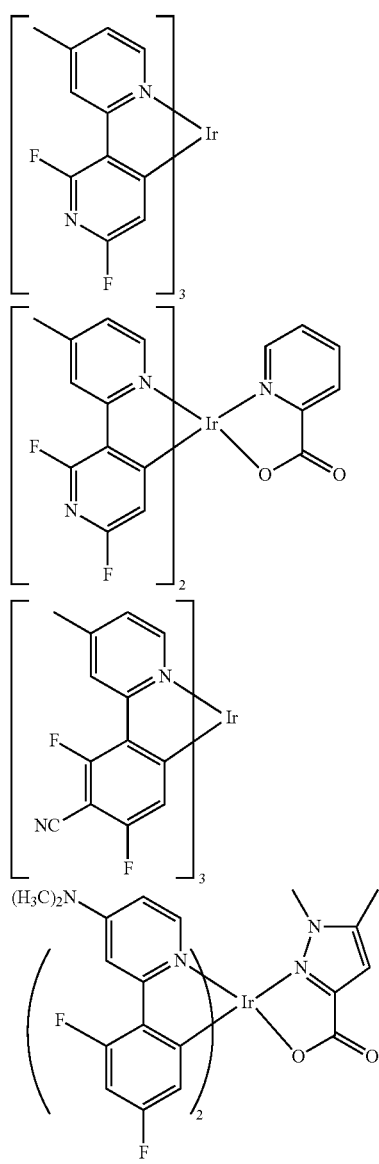
-continued
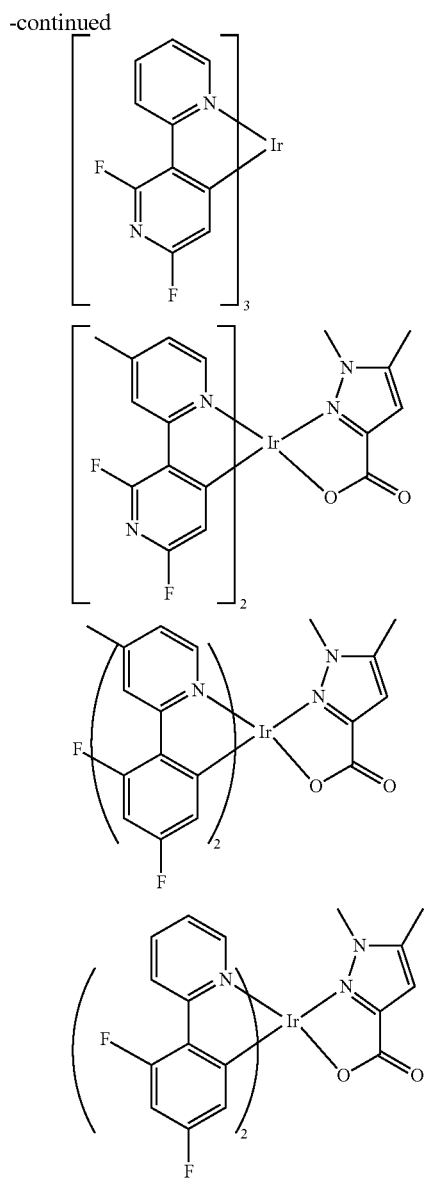
DPVBi
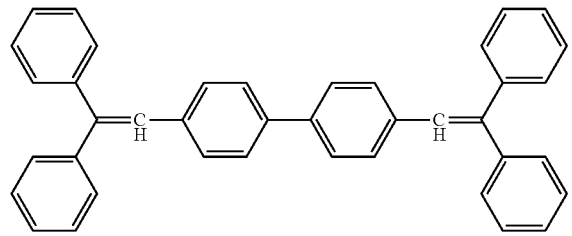
DPAVBi
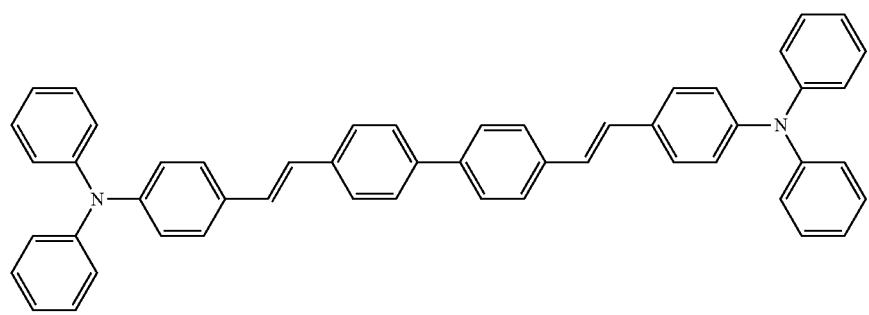

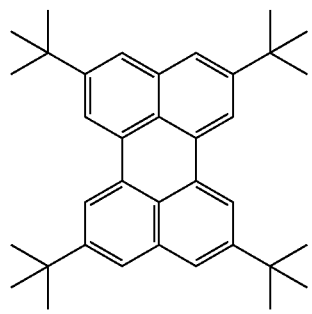
TBPe
For example, the following compounds may be used as a red dopant, without being limited thereto.
PtOEP
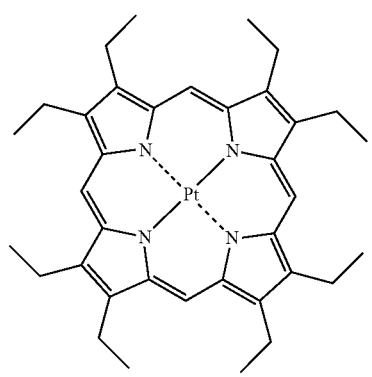
Ir(pq)$_2$(acac)
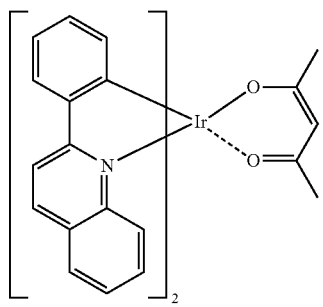
Ir(piq)$_3$
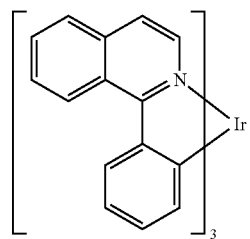
Ir(2-phq)$_3$
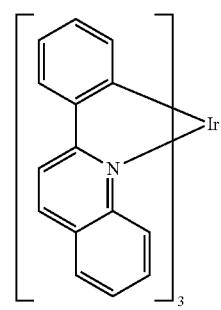
Btp$_2$Ir(acac)
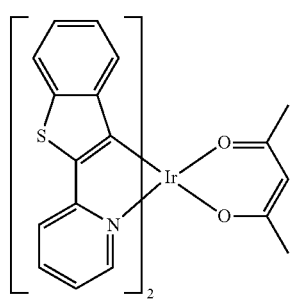
Ir(BT)$_2$(acac)
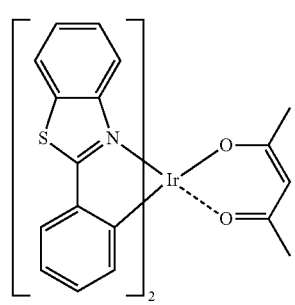
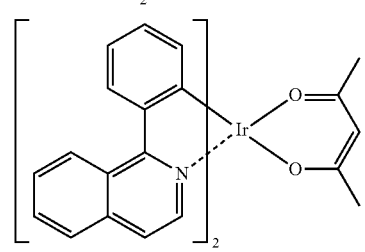

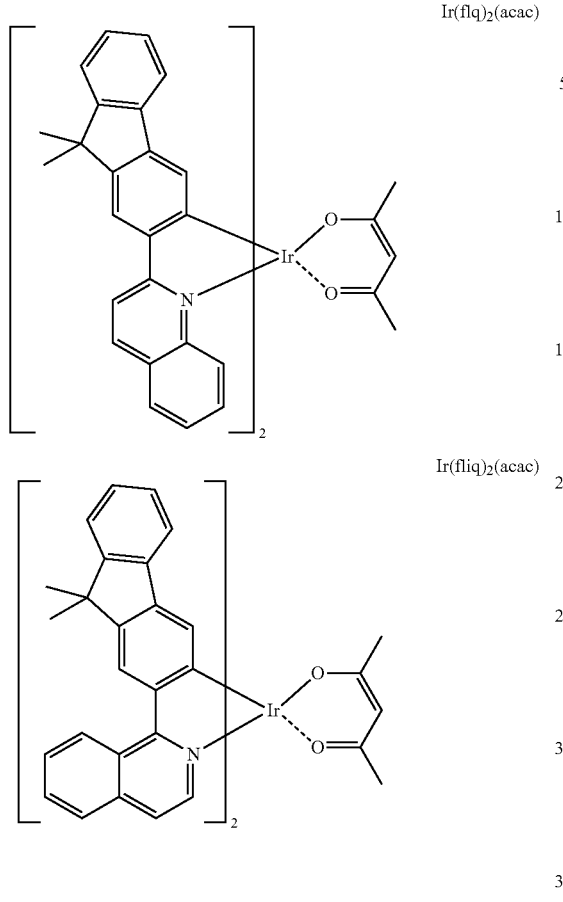
Ir(flq)₂(acac)
Ir(fliq)₂(acac)
DCM
DCJTB
For example, the following compounds may be used as a green dopant, without being limited thereto.
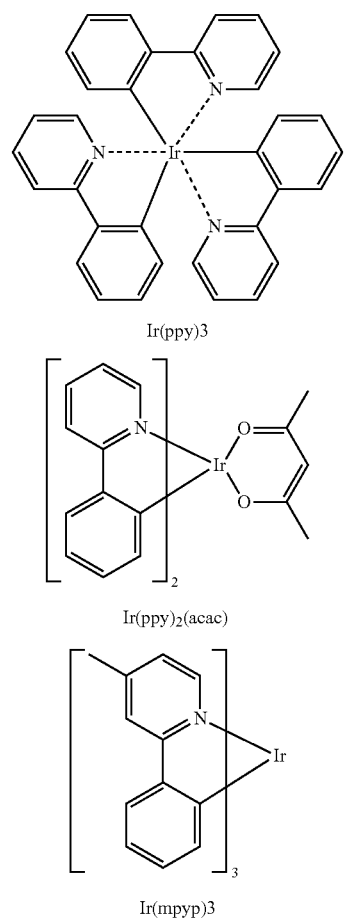
Ir(ppy)3
Ir(ppy)₂(acac)
Ir(mpyp)3
C545T
Meanwhile, the dopant contained in the EML may be a metal complex, as set forth in the following compounds D1-D50, without being limited thereto.
D1

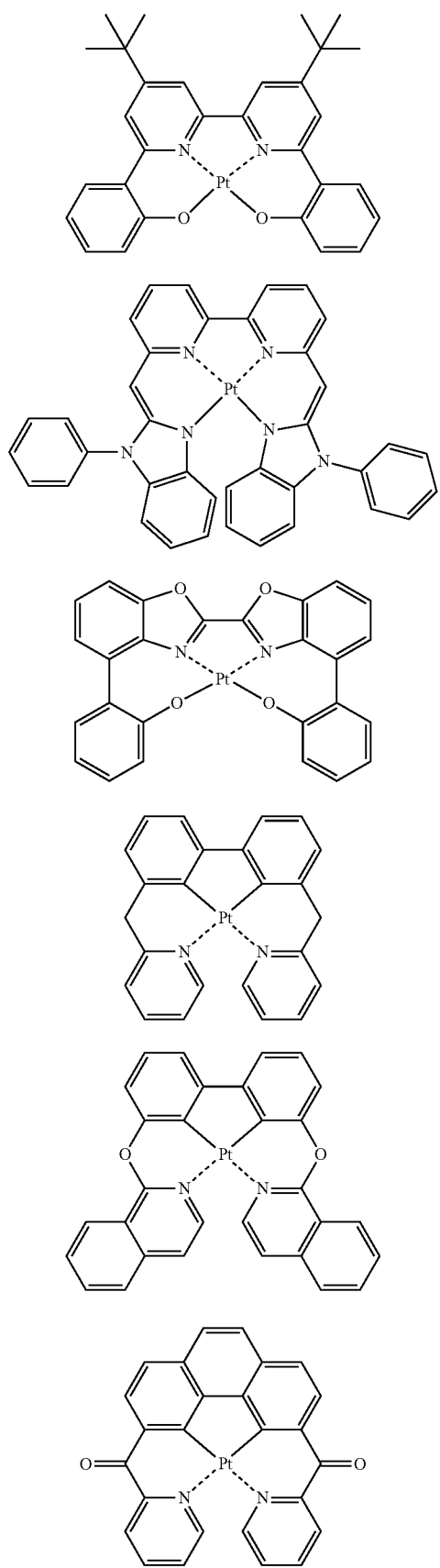
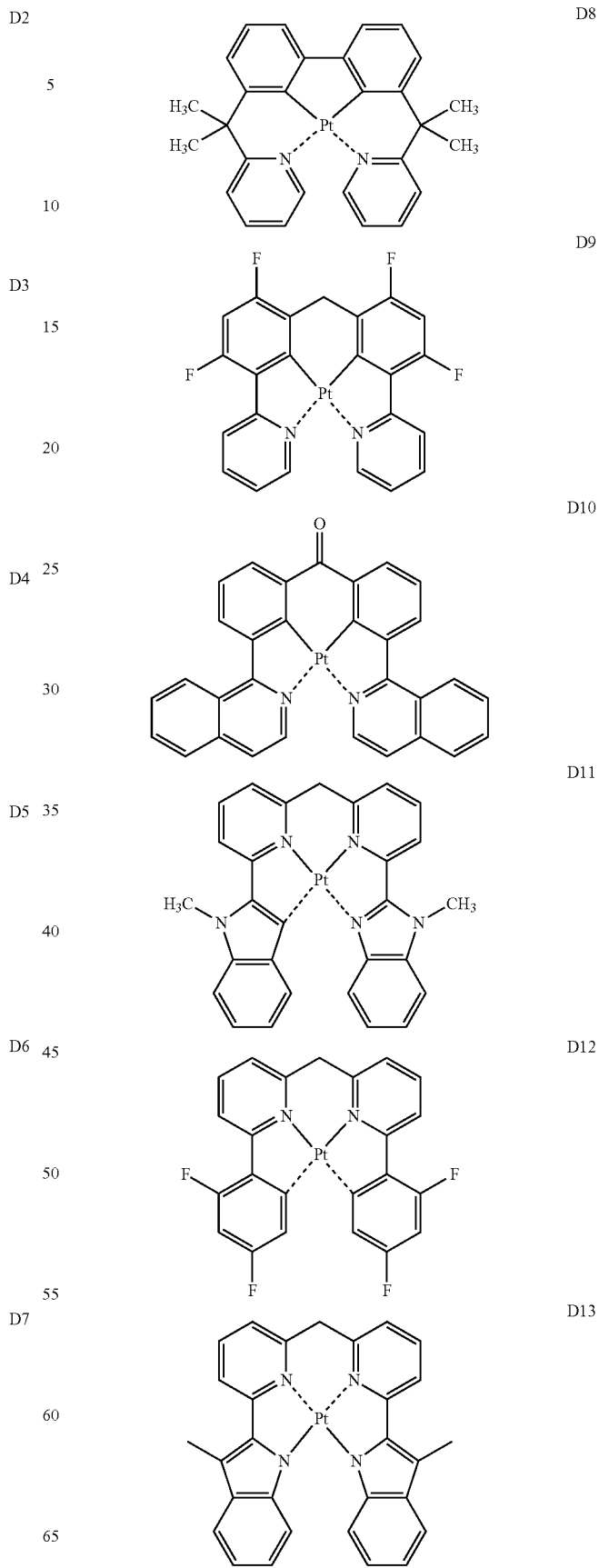

D14
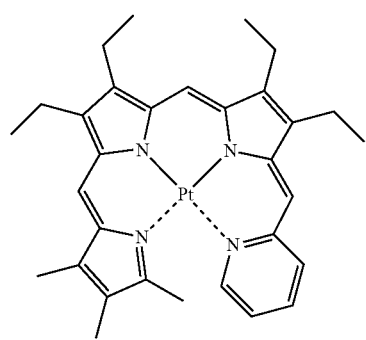
D15
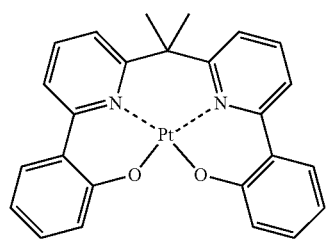
D16
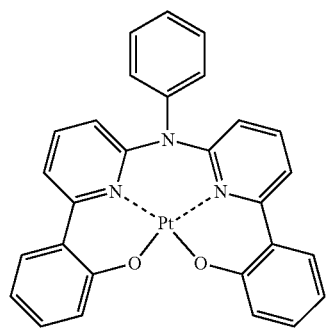
D17
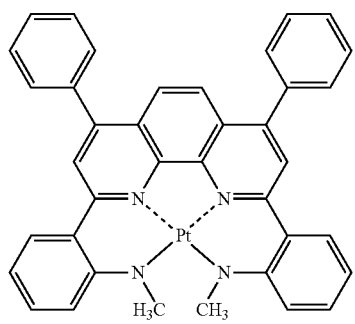
D18
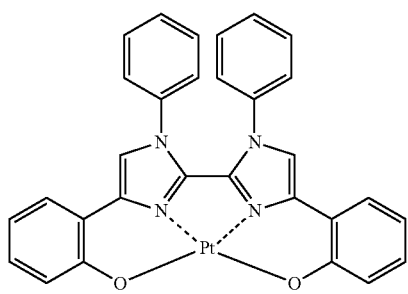
D19
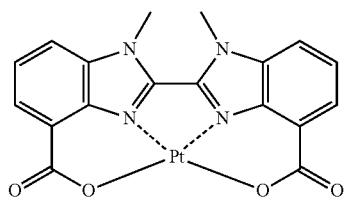
D20
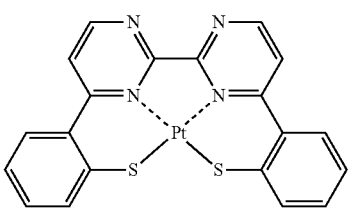
D21
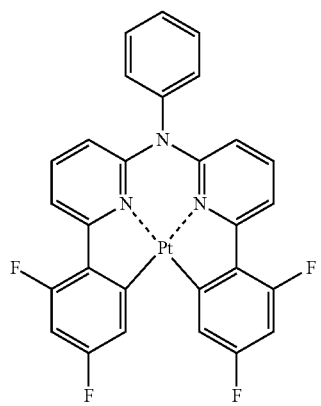
D22
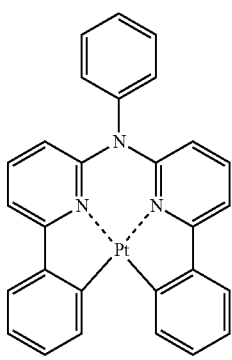
D23
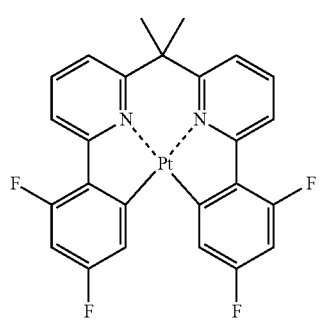

-continued
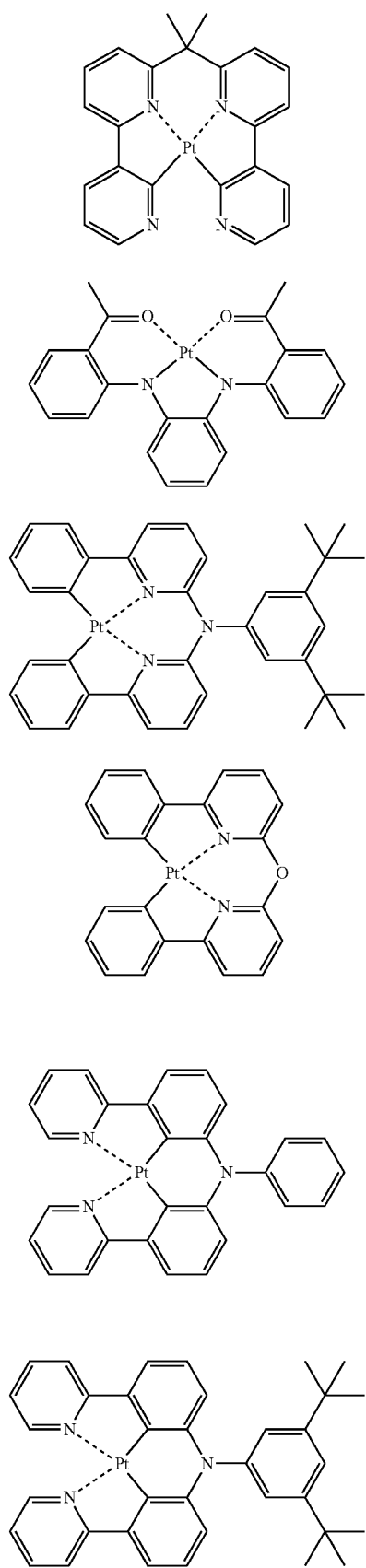
D24
D25
D26
D27
D28
D29
-continued
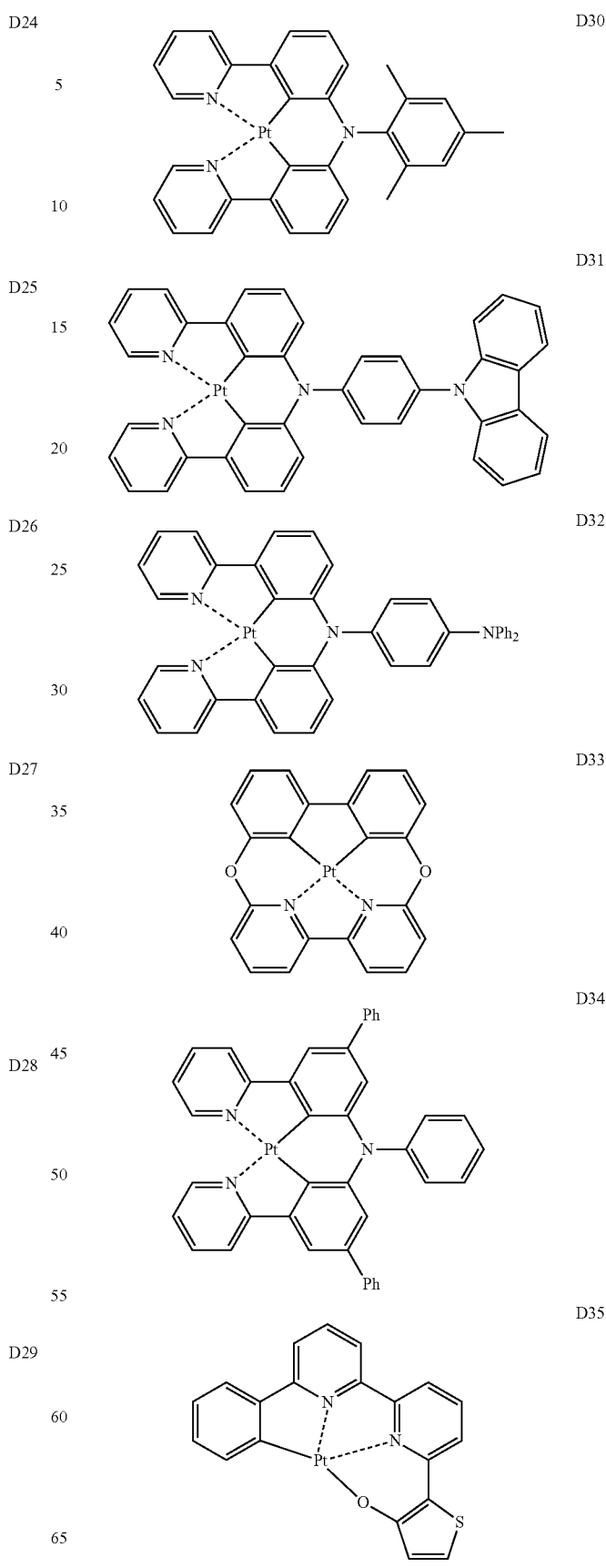
D30
D31
D32
D33
D34
D35

D36
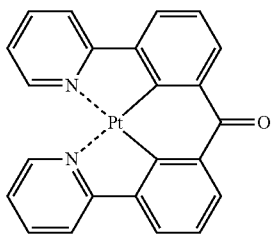
D37
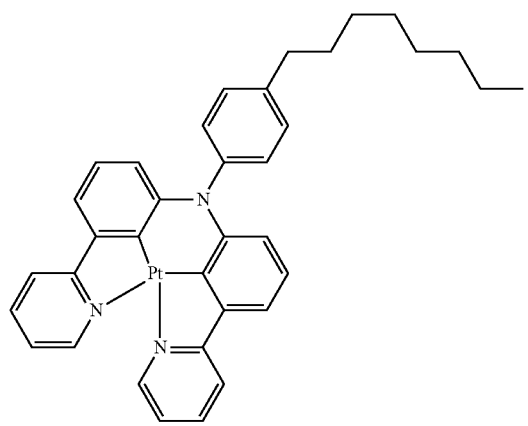
D38
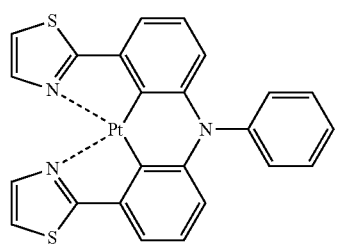
D39
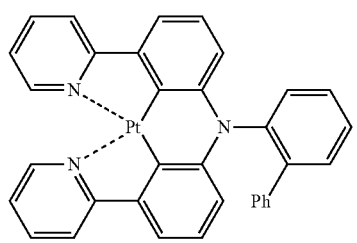
D40
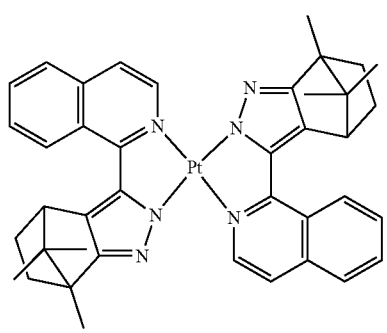
D41
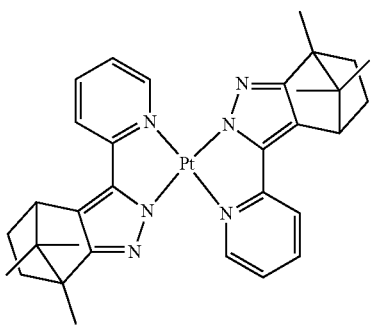
D42
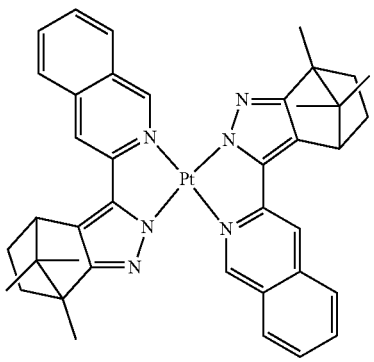
D43
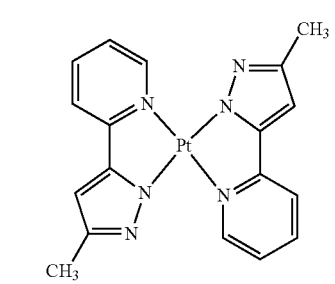
D44
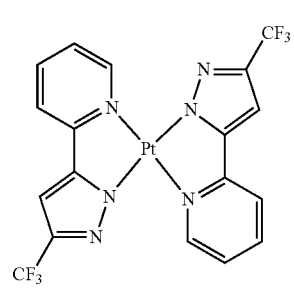
D45
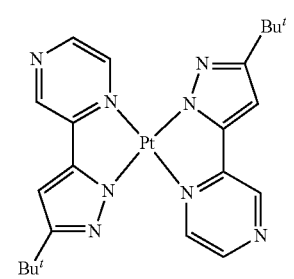

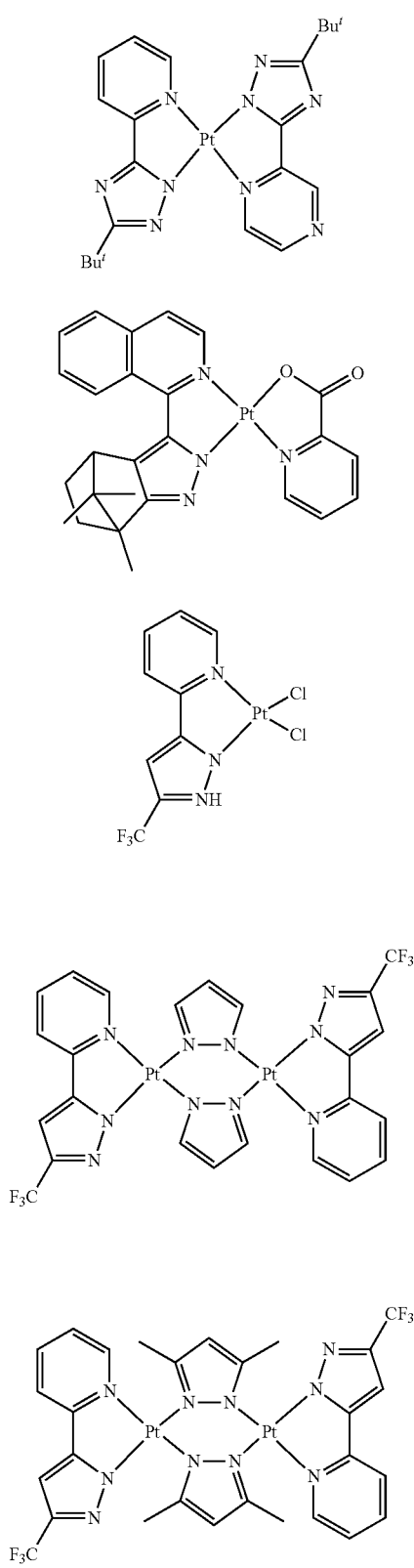
In addition, the dopant contained in the EML may be an Os-complex, as set forth in the following compounds, without being limited thereto.
When the EML includes a host and a dopant, the amount of the dopant may be in the range of about 0.01 to about 15 parts by weight based on 100 parts by weight of the host, but is not limited thereto.

The thickness of the EML may be about 100 to about 1,000 Å, and for example, about 200 to about 600 Å. When the thickness of the EML is within the range described above, the EML may have excellent light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for formation of the HIL, although the deposition and coating conditions may vary according to a compound that is used to form the ETL. An electron transporting material may be any material stably transporting electrons injected from the electron injecting electrode (cathode). The heterocyclic compound according to an embodiment or any known electron transporting material may be used. Examples of known electron transporting materials include quinoline derivatives, such as tris-(8-quinolinorate)aluminum (Alq3), TAZ, Balq, beryllium bis(benzoquinolin-10-olate) (Balq$_2$), ADN, Compound 201, Compound 202, and BCP without being limited thereto.

Compound 202

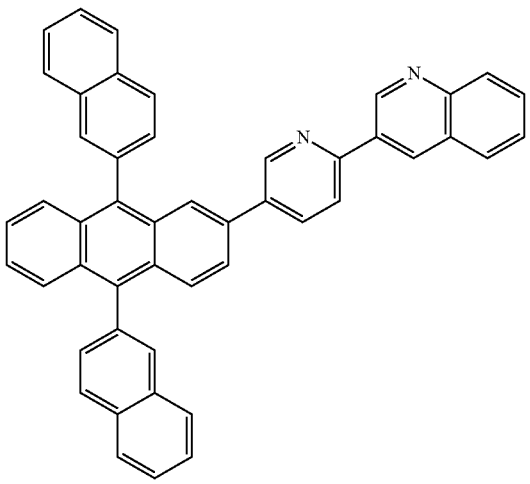

TAZ

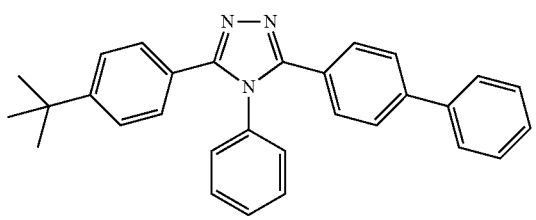

BCP

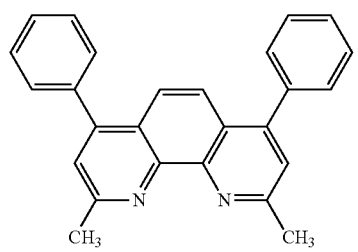

BAlq

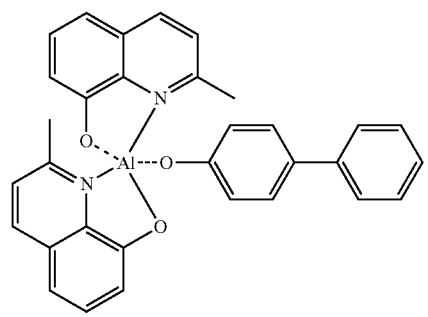

The thickness of the ETL may be about 100 to about 1,000 Å, and for example, about 150 to about 500 Å. When the thickness of the ETL is within the range described above, the ETL may have excellent electron transporting ability without a substantial increase in driving voltage.

Alternatively, the ETL may further include a metal-containing material in addition to known electron transporting organic compounds.

The metal-containing material may include a Li complex. Examples of the Li complex include lithium quinolate (LiQ) or Compound 203 below, but are not limited thereto.

Compound 201

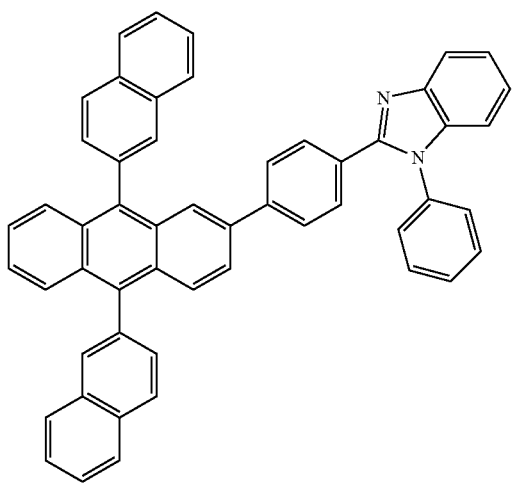

Compound 203

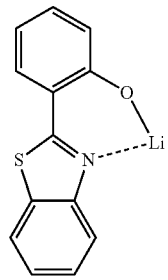

In addition, an EIL may be formed on the ETL using any material that allows electrons to be easily injected from the cathode.

Any known electron injecting materials such as LiF, NaCl, CsF, Li₂O, and BaO may be used to form the EIL. The conditions for deposition of the EIL are similar to those for formation of the HIL, although the deposition conditions may vary according to a material that is used to form the EIL.

The thickness of the EIL may be about 1 to about 100 Å, and for example, about 3 to about 90 Å. When the thickness of the EIL is within the range described above, the EIL may have excellent electron injecting ability without a substantial increase in driving voltage.

A second electrode is disposed on the organic layer. The second electrode may be a cathode; which is an electron injecting electrode. A metal used to form the second electrode may be a metal, an alloy, an electrically conductive compound, which have a low work function, or any mixture thereof. For example, the second electrode may be a transmissive electrode formed of lithium (Li), magnesium (Mg), aluminum (Al), an Al—Li alloy, calcium (Ca), an Mg—In alloy, or an Mg—Ag alloy in a thin film. Meanwhile, in order to manufacture a top-emission type organic light-emitting device, a transmissive electrode formed of ITO or IZO may be used, and various modifications may be applied thereto.

The organic light-emitting device is described with reference to FIG. 1, but is not limited thereto.

In addition, when a phosphorescent dopant is used to form the EML, an HBL may be formed between the HTL and the EML or between the H-functional layer and the EML by using vacuum deposition, spin coating, casting, LB deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole blocking material that is commonly used in the art may be used. Examples of the known hole blocking materials include an oxadiazole derivative, a triazole derivative, and a phenanthroline derivative. For example, BCP may be used as the hole blocking material.

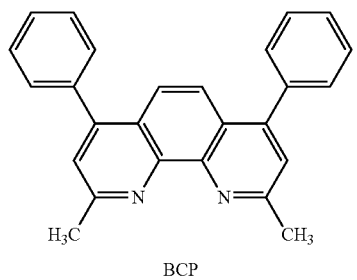 [SMILES: Cc1cc(-c2ccccc2)c2ccc3c(-c4ccccc4)cc(C)nc3c2n1 ; "BCP"]

BCP

The thickness of the HBL may be about 20 to about 1,000 Å, and for example, about 30 to about 300 Å. When the thickness of the HBL is within the range described above, the HBL may have excellent hole blocking ability without a substantial increase in driving voltage.

The organic light-emitting device according to an embodiment may be mounted in various types of flat panel display devices, such as a passive matrix organic light-emitting display device or an active matrix organic light-emitting display device. In particular, when the organic light-emitting device is applied to an active matrix organic light-emitting display device, the first electrode formed on the substrate may function as a pixel electrode and may be electrically connected to a source electrode or a drain electrode of the thin-film transistor. Moreover, the organic light-emitting device may also be applied to a flat panel display device having a double-sided screen.

The organic layer of the organic light-emitting device according to an embodiment described above may be formed of the heterocyclic compound of Formula 1 by using a deposition method or a wet method of coating a solution of the heterocyclic compound of Formula 1.

Hereinafter, one or more embodiments will be described in detail with reference to the following examples. These examples are not intended to limit the purpose and scope of the one or more embodiments.

Synthesis routes of the compounds represented by Formulae 2 and 3 are illustrated below.

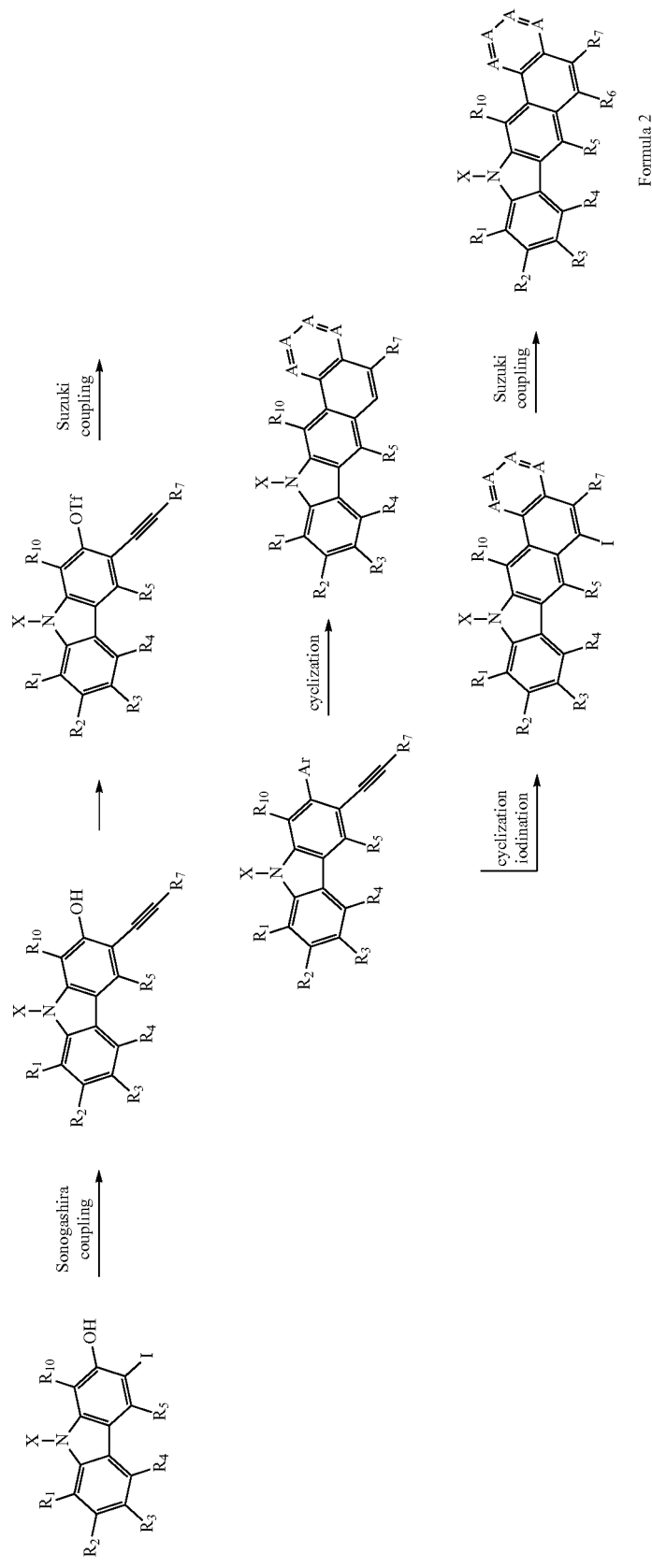

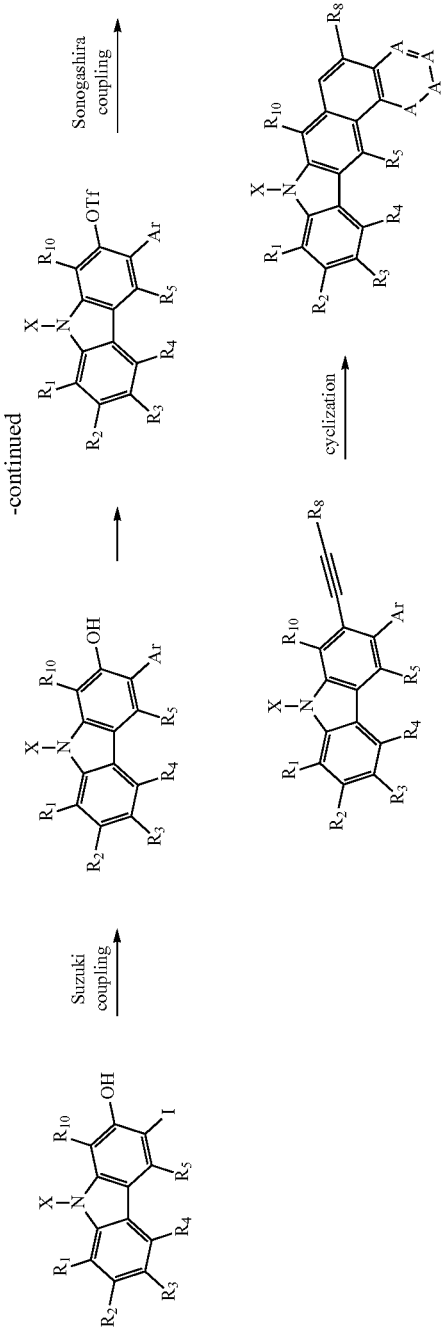
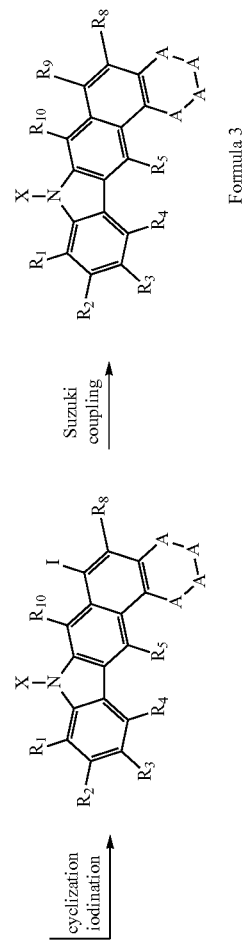

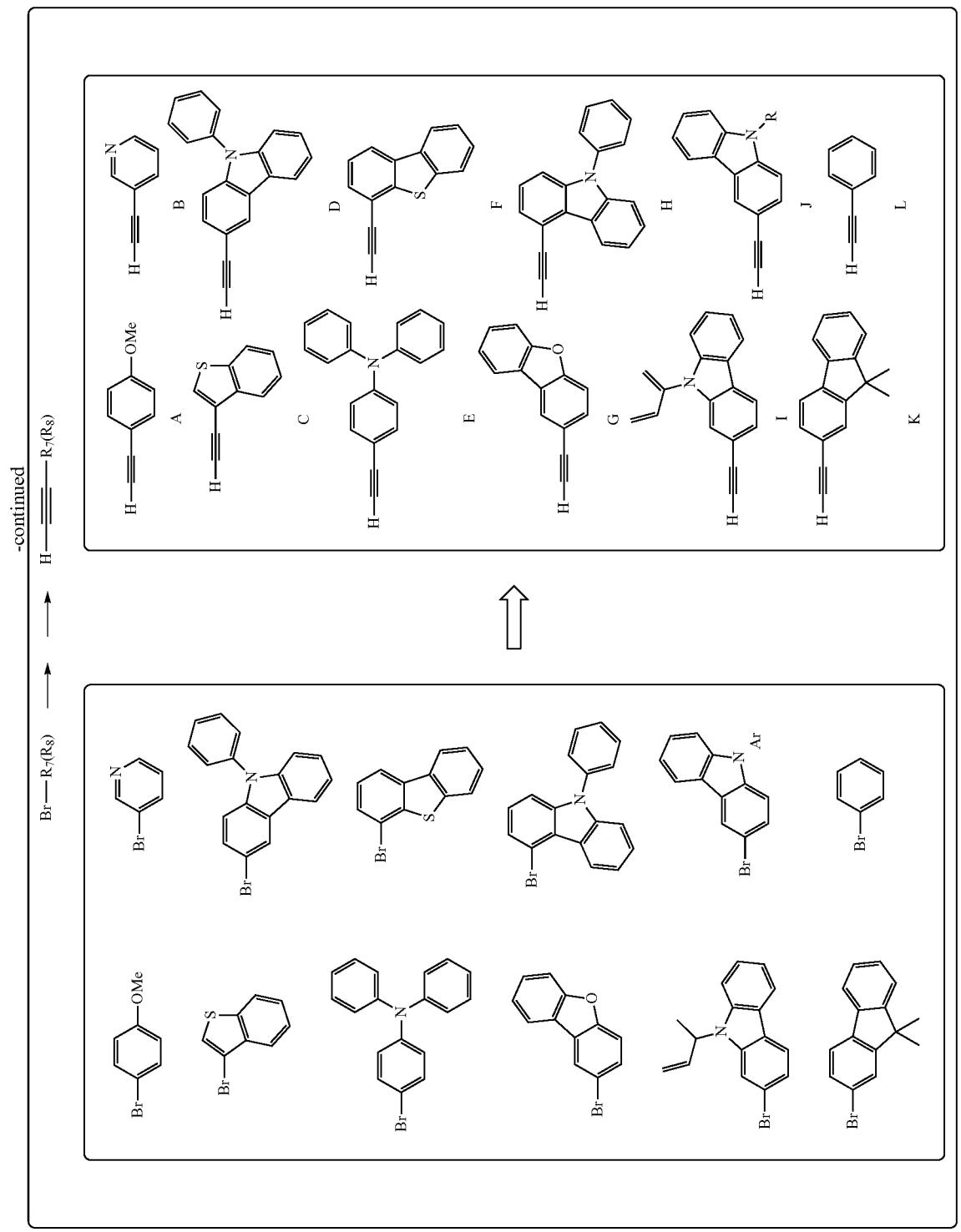

-continued
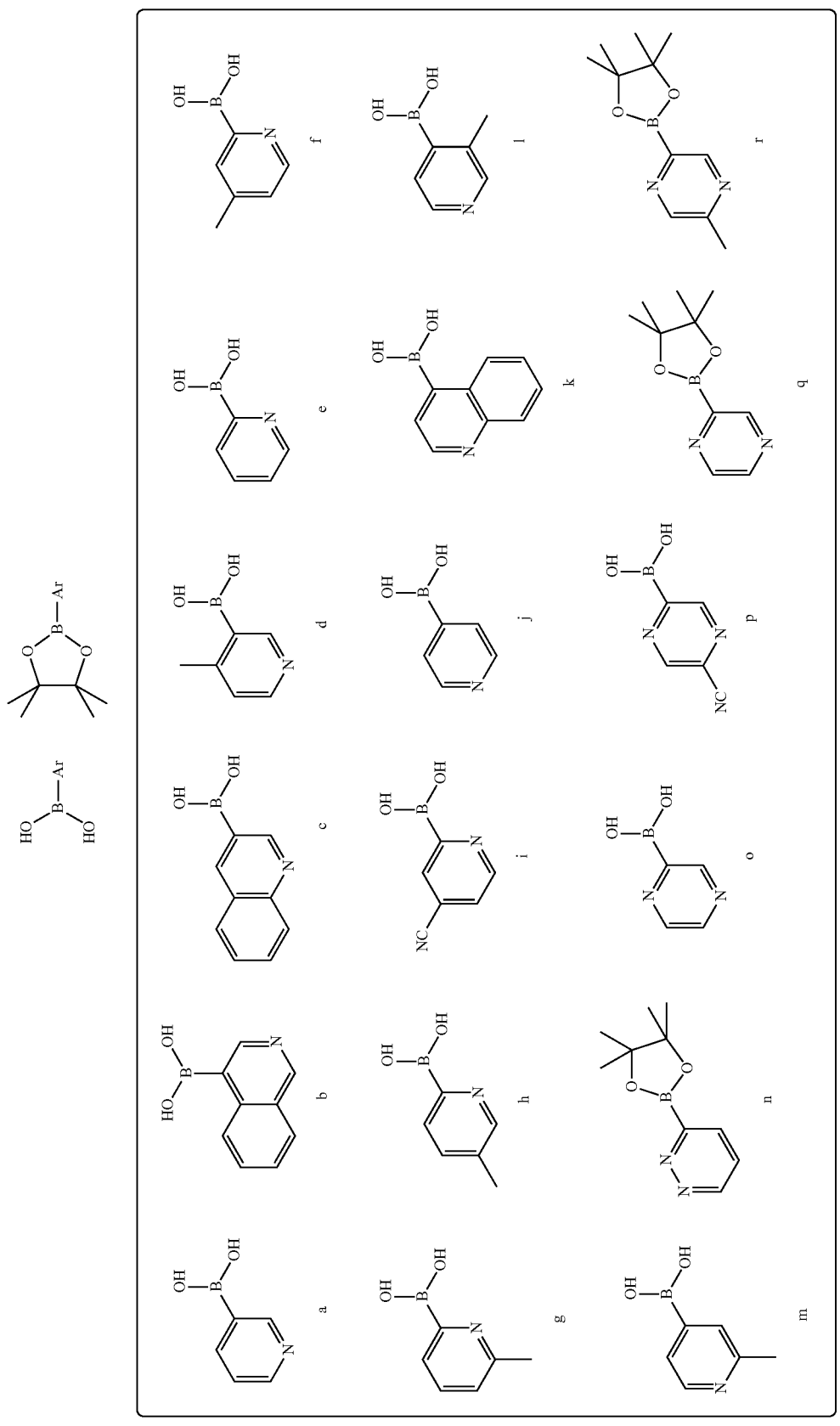

EXAMPLES

Synthesis Example 1: Synthesis of Intermediate D-a

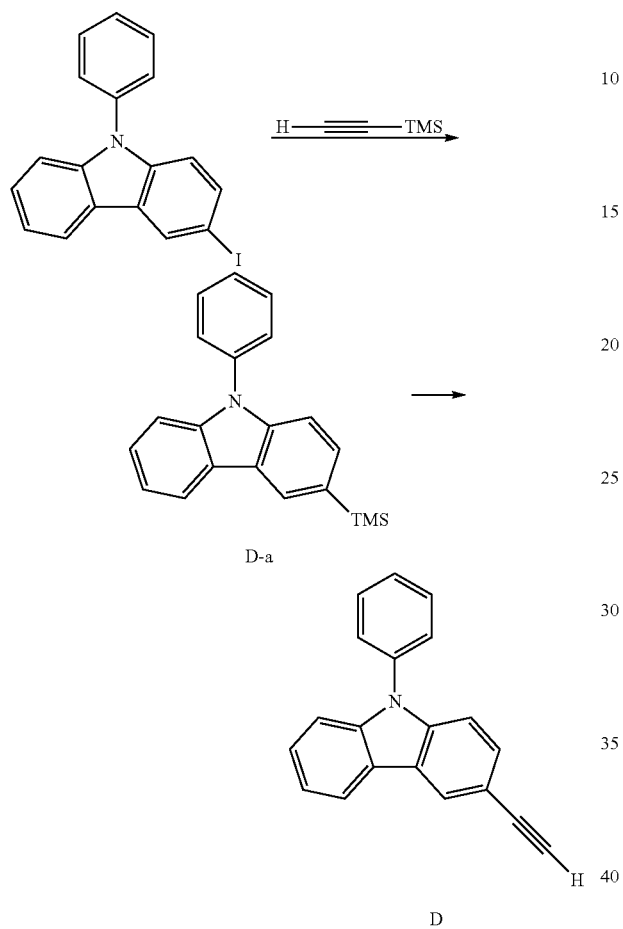

22 g of 3-Iodo-9-phenyl-9H-carbazole, 2.8 g (0.04 eq) of Pd(PPh$_3$)$_4$, 914 mg (0.08 eq) of CuI were added to a flask, the flask was vaccumized, and N$_2$ gas was added to the flask. 200 mL of THF was added thereto, and the flask was stirred. Then, 10 mL (1.2 eq) of triethylamine and 10.0 g (1.2 eq) of TMS-acetylene were slowly added thereto, and the flask was stirred in a N$_2$ atmosphere at room temperature for 2 hours. The solvent was removed using a rotary evaporator, and the resultant was subjected to extraction twice using 200 mL of Et$_2$O and 150 mL of water. An organic layer was collected and dried using magnesium sulfate to evaporate the solvent. The residue was separately purified using silica gel column chromatography to obtain 20 g of Intermediate D-a (Yield: 99%). The produced compound was identified using LC-MS. C$_{23}$H$_{21}$N$_1$Si$_1$: M+ 339.14

Synthesis Example 2: Synthesis of Intermediate D 4.2 g of Intermediate D-a was dissolved in 50 mL of THF, 30 mL (3 eq) of tetrabutylammonium fluoride in THF (1.0 M) was added thereto in drops, and the reaction solution was stirred for 30 minutes. The reaction solution was subjected to extraction three times using 50 mL of water and 50 mL of ethylether. An organic layer was collected and dried using magnesium sulfate to evaporate the solvent. The residue was separately purified using silica gel column chromatography to obtain 3.5 g of Intermediate D (Yield: 95%). The produced compound was identified using LC-MS. C$_{20}$H$_{13}$N$_1$: M+ 267.10

Synthesis of Intermediates A to L

Intermediates A to L as illustrated above immediately following the illustrated synthesis routes of the compounds represented by Formulae 2 and 3 were synthesized in the same manner and same equivalent as Synthesis Examples 1 and 2. Yields and other properties are shown in Table 1 below.

TABLE 1

| Intermediate | Yield Synthesis Example 1 | Yield Synthesis Example 2 | LC-MS |
|---|---|---|---|
| A | 98 | 95 | 132.06 |
| B | 97 | 94 | 132.04 |
| C | 98 | 96 | 158.02 |
| D | 99 | 95 | 267.10 |
| E | 98 | 97 | 269.12 |
| F | 99 | 96 | 208.03 |
| G | 97 | 97 | 192.06 |
| H | 95 | 93 | 267.10 |
| I | 96 | 96 | 267.10 |
| J(R = J1) | 94 | 97 | 421.16 |
| J(R = J2) | 95 | 95 | 422.15 |
| J(R = J3) | 93 | 93 | 395.14 |
| J(R = J4) | 95 | 93 | 419.17 |
| J(R = J5) | 96 | 96 | 498.18 |
| K | 94 | 94 | 218.11 |
| L | 92 | 93 | 102.05 |

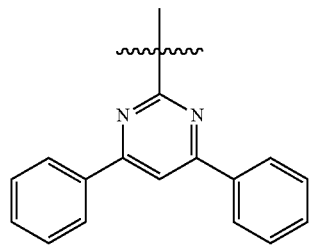

J1

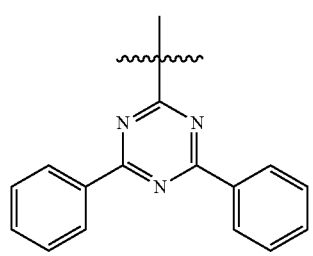

J2

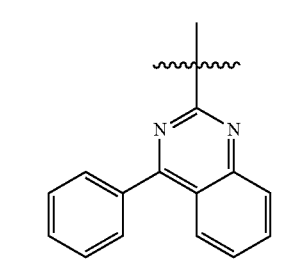

J3

-continued

J4

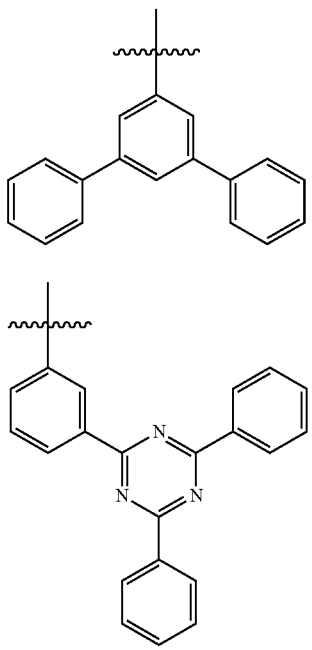

J5

Representative Synthesis Examples

Synthesis of Compound 7

Compound 7 was synthesized through Reaction Scheme 1 below:

Reaction Scheme 1

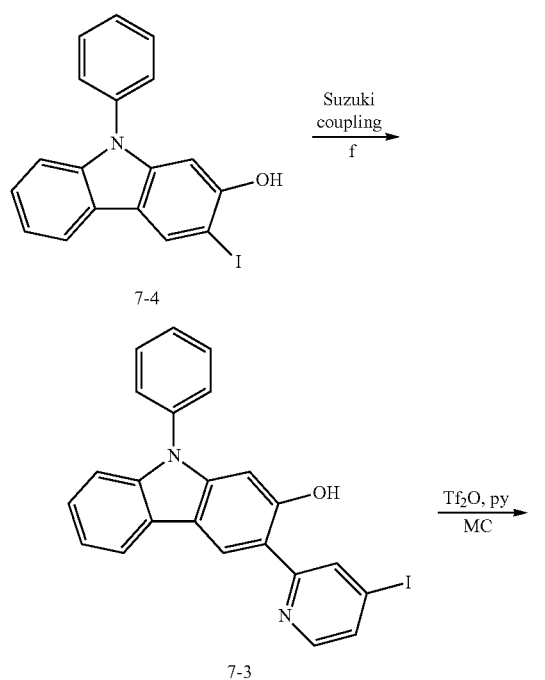

-continued

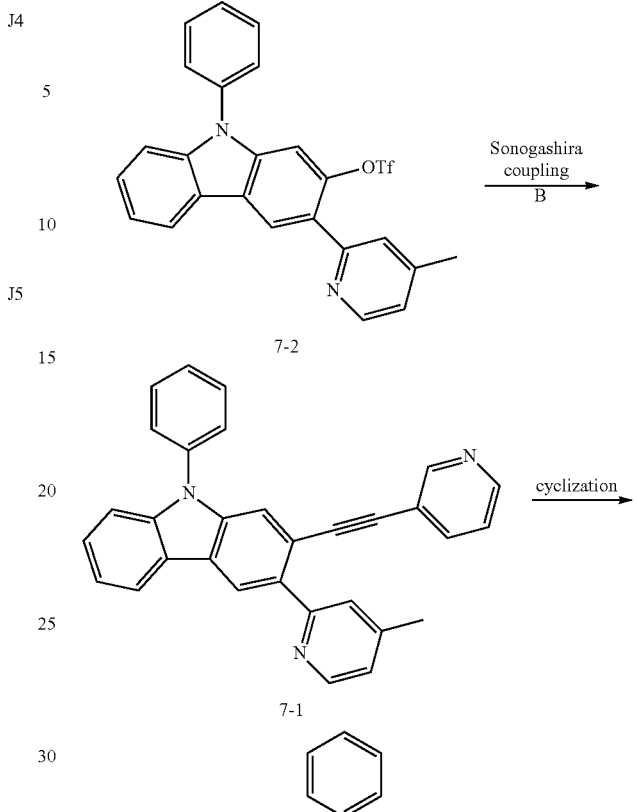

Synthesis Example 3: Synthesis of Compound 7-3

5 g of Intermediate 7-4, 2.67 g (1.2 eq) of Intermediate f, 750 mg (0.05 eq) of Pd(PPh$_3$), and 9 g (5 eq) of K$_2$CO$_3$ were dissolved in 100 mL of THF and 30 mL of distilled water. The reaction solution was stirred at 120° C. while refluxing for 24 hours. The reaction solution was cooled to room temperature and subjected to extraction three times using 200 mL of water and 200 mL of diethylether. An organic layer was collected and dried using magnesium sulfate to evaporate the solvent. The residue was separately purified using silica gel column chromatography to obtain 3.61 g of Intermediate 7-3 (Yield: 82%). The produced compound was identified using LC-MS. C$_{18}$H$_{12}$INO: M+ 385.14

Synthesis Example 4: Synthesis of Compound 7-2

3 g of Intermediate 7-3 was dissolved in 50 mL of dichloromethane, and 13.1 mL (20 eq) of trifuloroacetic acid was slowly added thereto, and the reaction solution was stirred at room temperature for 1 hour. When the reaction was terminated, the reaction solution was subjected to extraction three times using 100 mL of water and 100 mL of diethylether. An organic layer was collected and dried using magnesium sulfate to evaporate the solvent. The residue was separately purified using silica gel column chromatography to obtain 3.84 g of Compound 7-2 (Yield: 93%). The produced compound was identified using LC-MS. $C_{25}H_{17}F_3N_2O_3S$:M+ 482.09

Synthesis Example 5: Synthesis of Compound 7-1

3 g (1.2 eq) of Compound 7-2, 240 mg (0.04 eq) of Pd(PPh$_3$)$_4$, 89 mg (0.08 eq) of CuI were added to a flask, the flask was vaccumized, and N$_2$ gas was added to the flask. 100 mL of THF was added thereto, and the flask was stirred. 0.46 mL (1.2 eq) of triethylamine and 534 mg (1 eq) of Intermediate L were slowly added thereto, and the reaction mixture was stirred at room temperature and N$_2$ atmosphere for 2 hours. The solvent was removed using a rotary evaporator, and the reaction solution was subjected to extraction three times using 100 mL of water and 100 mL of ethylether. An organic layer was collected and dried using magnesium sulfate to evaporate the solvent. The residue was separately purified using silica gel column chromatography to obtain 1.29 g of Intermediate 7-1 (Yield: 57%). The produced compound was identified using LC-MS. $C_{31}H_{21}N_3$: M+ 435.17

Synthesis Example 6: Synthesis of Compound 7

1.2 g of Intermediate 7-1 was dissolved in 50 mL of MC, and 4.2 mL (20 eq) of trifuloroacetic acid was slowly added thereto, and the reaction solution was stirred at room temperature for 1 hour. When the reaction was terminated, the reaction solution was subjected to extraction three times using 100 mL of water and 100 mL of diethylether. An organic layer was collected and dried using magnesium sulfate to evaporate the solvent. The residue was separately purified using silica gel column chromatography to obtain 1.09 g of Compound 7 (Yield: 91%). The produced compound was identified using LC-MS. $C_{31}H_{21}N_3$: M+ 435.17

Synthesis of Compound 43

Compound 43 was synthesized through Reaction Scheme 2 below:

Reaction Scheme 2

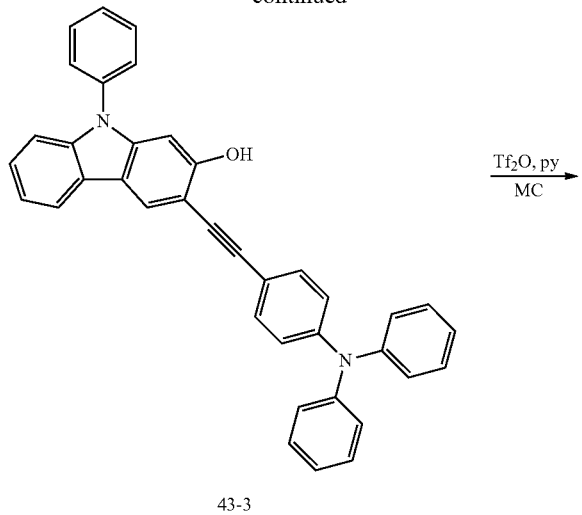

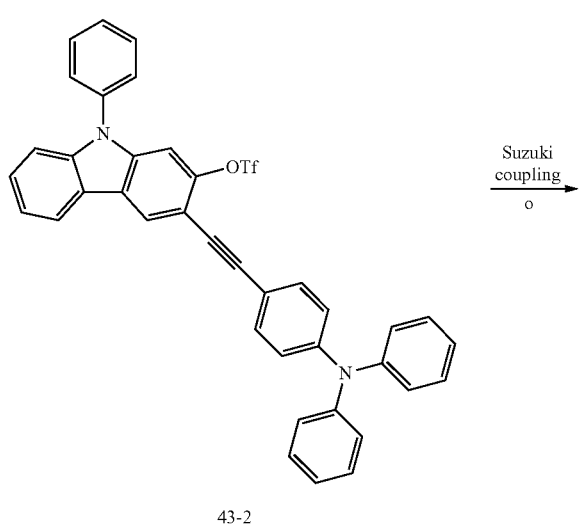

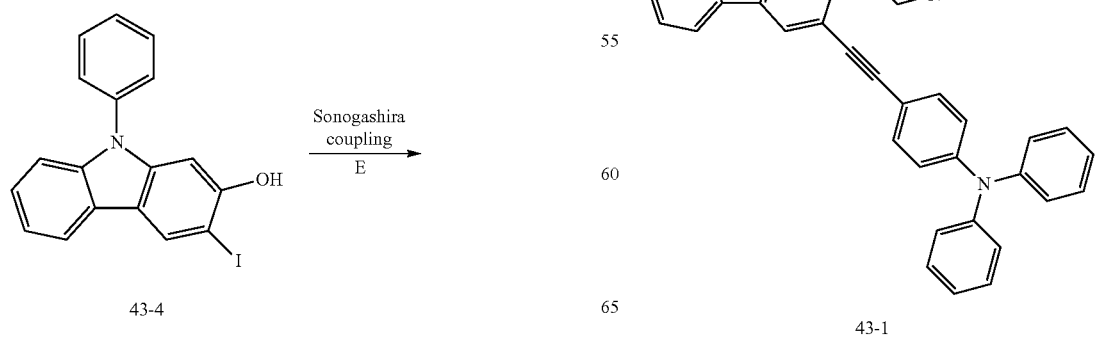

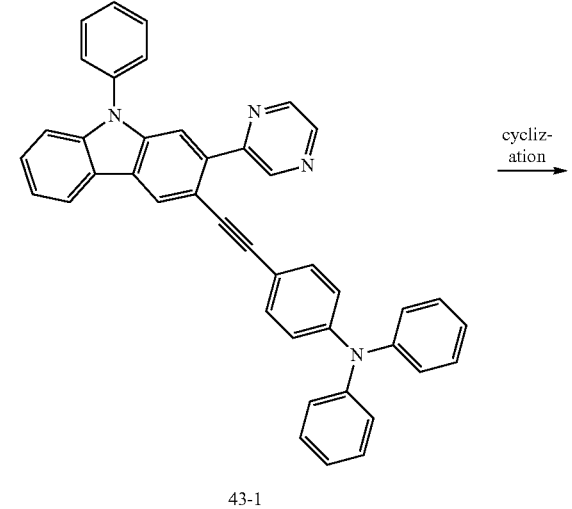

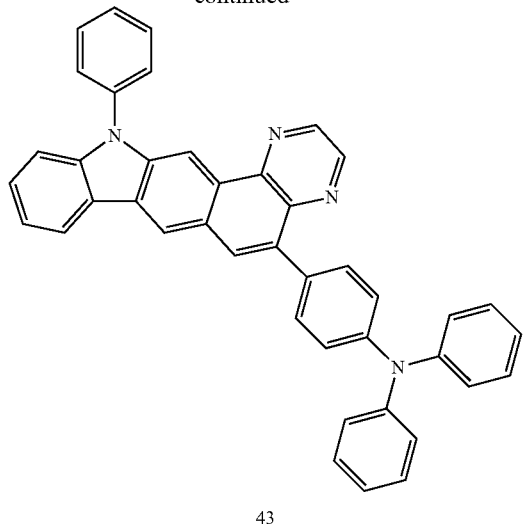

43

Synthesis Example 7: Synthesis of Compound 43-3

Compound 43-3 was synthesized in the same manner as in Synthesis Example 5. The produced compound was identified using LC-MS. $C_{38}H_{26}N_2O$: M+ 527.21

Synthesis Example 8: Synthesis of Compound 43-2

Compound 43-2 was synthesized in the same manner as in Synthesis Example 4. The produced compound was identified using LC-MS. $C_{39}H_{25}F_3N_2O_3S$: M+ 658.15

Synthesis Example 9: Synthesis of Compound 43-1

Compound 43-1 was synthesized in the same manner as in Synthesis Example 3. The produced compound was identified using LC-MS. $C_{42}H_{28}N_4$: M+ 588.23

Synthesis Example 10: Synthesis of Compound 43

Compound 43 was synthesized in the same manner as in Synthesis Example 6. The produced compound was identified using LC-MS. $C_{42}H_{28}N_4$: M+ 588.23

Synthesis of Compounds 1 to 6 and 8 to 27

Compounds 1 to 6 and 8 to 27 (as set forth above as examples of the heterocyclic compound of Formula 1) were synthesized in the same manner as in the method of synthesizing Compound 7. The produced compound was identified using LC-MS and NMR.

Synthesis of Compounds 28 to 42 and 44 to 53

Compounds 28 to 42 and 44 to 53 (as set forth above as examples of the heterocyclic compound of Formula 1) were synthesized in the same manner as in the method of synthesizing Compound 43. The produced compound was identified using LC-MS and NMR.

The results are shown in Table 2 below.

TABLE 2

| Compound | LC-MS | 1H NMR |
|---|---|---|
| 1 | 420.16 | 9.37(s, 1H) 8.55(d, 1H), 8.45(d, 1H), 7.94(d, 1H), 7.79(d, 2H), 7.62-7.35(m, 13H), 7.16(m, 1H) |
| 2 | 585.22 | 8.87(d, 1H), 8.55-8.51(m, 2H), 8.30(d, 1H), 8.19-8.17(m, 2H), 7.94-7.89(m, 2H), 7.62-7.35(m, 17H), 7.20-7.16(m, 2H) |
| 3 | 635.24 | 8.62-8.55(m, 2H), 8.26-8.14(m, 4H), 7.96-7.94(m, 2H), 7.83-7.35(m, 19H), 8.20-7.16(m, 2H) |
| 4 | 635.24 | 8.55(d, 2H), 8.11-7.83(m, 7H), 7.68-7.50(m, 15H), 7.40-7.35(m, 3H), 7.16(m, 2H) |
| 5 | 754.28 | 8.64(d, 1H), 8.55(d, 1H), 8.36-8.30(m, 5H), 8.19-8.13(m, 2H), 7.97-7.89(t, 2H), 7.62-7.35(m, 18H), 7.20-7.16(m, 2H), 2.66(s, 3H) |
| 6 | 450.17 | 8.81(d, 1H), 8.55(d, 1H), 8.44(d, 1H), 7.94(d, 1H), 7.71-7.35(12H), 7.16(t, 1H), 7.02(d, 2H), 3.81(s, 3H) |
| 7 | 435.17 | 9.24(s, 1H), 8.71-8.70(m, 2H), 8.55(d, 1H), 8.42(d, 1H), 7.94(d, 1H), 7.77(s, 1H), 7.62-7.50(m, 8H), 7.40-7.35(m, 2H), 7.16(t, 1H), 2.68(s, 3H) |
| 8 | 490.15 | 8.55(d, 1H), 8.45(d, 1H), 8.29(t, 2H), 8.03(d, 1H), 7.94(d, 1H), 7.71(s, 1H), 7.62-7.55(m, 8H), 7.40-7.30(m, 3H), 7.16(t, 1H), 2.76(s, 3H) |
| 9 | 601.25 | 8.63(s, 1H), 8.55(d, 1H), 8.15(s, 1H), 7.94(d, 1H), 7.62-7.55(m, 8H), 7.40-7.37(m, 4H), 7.24-7.00(m, 12H), 2.48(s, 3H) |
| 10 | 551.15 | 8.82(d, 1H), 8.55(m, 2H), 8.45(d, 1H), 8.82(d, 1H), 7.94-7.93 (m, 2H), 7.70-7.35(m, 13H), 7.16(t, 1H) |
| 11 | 510.17 | 9.30(s, 1H), 8.55(d, 1H), 8.39(d, 1H), 7.98-7.79(m, 5H), 7.62-7.31(m, 13H), 7.16(t, 1H) |
| 12 | 470.18 | 8.55(d, 1H), 8.26(s, 1H), 8.14(d, 1H), 7.96-7.94(m, 2H), 7.62-7.39(m, 16H), 7.16(t, 1H) |
| 13 | 599.24 | 9.13(s, 1H), 8.62(d, 1H), 8.55(d, 1H), 8.22-8.19(m, 2H), 8.12(s, 1H), 7.94(d, 1H), 7.74(s, 1H), 7.62-7.50(m, 13H), 7.40-7.35(m, 3H), 7.20-7.16(m, 2H), 2.36(s, 3H) |
| 14 | 599.24 | 9.12(s, 1H), 8.55(d, 1H), 8.30(d, 1H), 8.19-8.17(m, 2H), 7.94-7.89(t, 2H), 7.62-7.33(m, 17H), 7.20-7.16(m, 2H), 2.69(s, 3H) |
| 15 | 599.24 | 8.55(d, 1H), 8.30-8.17(m, 4H), 7.94-7.89(m, 2H), 7.62-7.50(m, 17H), 7.40-7.35(m, 3H), 7.20-7.16(m, 2H), 3.03(s, 3H) |
| 16 | 586.22 | 9.03(d, 1H), 8.55(m, 2H), 7.94-7.91(m, 3H), 7.62-7.35(m, 18H), 7.16(m, 2H) |
| 17 | 741.26 | 8.74(d, 2H), 8.55(m, 2H), 8.36(d, 4H), 7.99-7.94(m, 5H), 7.77(d, 1H), 7.62-7.35(m, 15H), 7.16(m, 2H) |

TABLE 2-continued

| Compound | LC-MS | 1H NMR |
|---|---|---|
| 18 | 447.15 | 9.24(s, 1H), 8.70(d, 2H), 8.55(d, 1H), 8.42(d, 1H), 7.94-7.89(t, 2H), 7.62-7.50(m, 7H), 7.40-7.35(m, 2H), 7.16(t, 1H) |
| 19 | 465.18 | 8.68(s, 1H), 8.55(d, 1H), 7.94-7.88(t, 2H), 7.71-7.50(m, 8H), 7.40-7.35(t, 2H), 7.16(t, 1H), 7.02(d, 2H), 3.81(s, 3H), 2.42(s, 3H) |
| 20 | 438.15 | 9.37(s, 1H), 8.55(d, 1H), 8.45(d, 1H), 7.94(d, 1H), 7.79-7.40(m, 14H), 7.16(t, 1H) |
| 21 | 552.17 | 8.94(d, 1H), 8.55(d, 1H), 8.46-8.45(m, 2H), 8.29(s, 1H), 8.03(d, 1H), 7.95-7.91(m, 6H), 7.75(d, 2H), 7.63-7.41(m, 9H), 7.16(t, 1H) |
| 22 | 792.3 | 8.55(d, 1H), 8.36(d, 4H), 8.26(s, 1H), 8.14(d, 1H), 7.96-7.94(m, 2H), 7.83(t, 1H), 7.69(t, 1H), 7.55-7.00(m, 25H) |
| 23 | 807.25 | 8.55(d, 2H), 8.45(d, 1H), 8.36-8.32(m, 5H), 8.11-8.05(t, 2H), 7.96-7.83(m, 8H), 7.70-7.69(m, 2H), 7.56-7.49(m, 10H), 7.40-7.35(m, 2H), 7.16(t, 1H) |
| 24 | 678.24 | 8.64-8.55(m, 3H), 7.98-7.88(m, 9H), 7.55-7.31(m, 14H), 7.16(t, 1H), 2.68(s, 3H) |
| 25 | 610.22 | 8.81(d, 1H), 8.62-8.55(m, 2H), 8.44(d, 1H), 8.22-8.19(m, 2H), 7.94-7.91(m, 3H), 7.74(t, 3H), 7.62-7.50(m, 9H), 7.40-7.32(m, 3H), 7.20-7.16(m, 2H) |
| 26 | 667.22 | 8.58-8.55(m, 3H), 7.08(s, 1H), 7.94-7.91(m, 3H), 7.62-7.32(m, 16H), 7.16(m, 2H), 2.68(s, 3H) |
| 27 | 675.27 | 8.55(d, 1H), 8.30-8.17(m, 5H), 7.94-7.89(t, 2H), 7.75-7.35(m, 18H), 7.26-7.16(m, 4H), 2.76(s, 3H) |
| 28 | 740.27 | 9.37(s, 1H), 8.55(m, 2H), 8.45(d, 1H), 8.36(d, 4H), 7.99-7.89(m, 4H), 7.77(d, 1H), 7.62-7.35(m, 17H), 7.16(m, 2H) |
| 29 | 450.17 | 8.87(d, 1H), 8.55-8.51(m, 2H), 7.94(d, 1H), 7.71-7.50(m, 10H), 7.40-7.35(m, 2H), 7.16(t, 1H), 7.02(d, 2H), 3.81(s, 3H) |
| 30 | 471.17 | 9.24(s, 1H), 8.70(d, 1H), 8.55(d, 1H), 8.42(d, 1H), 8.26(s, 1H), 8.14(d, 1H), 7.96-7.83(m, 4H), 8.69-7.50(m, 8H), 7.40-7.35(m, 2H), 7.16(t, 1H) |
| 31 | 526.15 | 8.55(d, 1H), 8.45(d, 1H), 8.29(s, 1H), 8.26(s, 1H), 8.11-8.03(m, 2H), 7.95-7.94(t, 2H), 7.83(d, 1H), 7.62-7.35(m, 12H), 7.16(t, 1H) |
| 32 | 601.25 | 8.64(d, 1H), 8.55(d, 1H), 7.94(d, 1H), 7.62-7.00(m, 25H), 2.68(s, 3H) |
| 33 | 526.15 | 8.81(d, 1H), 8.55(d, 1H), 8.45-8.44(m, 2H), 8.03-7.93(m, 4H), 7.62-7.32(m, 13 H), 7.16(t, 1H) |
| 34 | 524.19 | 8.58-8.55(m, 2H), 7.98-7.83(m, 5H), 7.62-7.31(131-1), 7.16(t, 1H), 2.68(s, 3H) |
| 35 | 434.18 | 8.55(d, 1H), 8.26(d, 1H), 7.94(d, 1H), 7.79(d, 2H), 7.62-7.35(11H), 7.26-7.16(m, 3H), 2.76(s, 3H) |
| 36 | 599.24 | 8.63(s, 1H), 7.55(d, 2H), 8.31(d, 1H), 8.15(s, 1H), 7.94-7.91(m, 3H), 7.74(s, 1H), 7.62-7.50(m, 11H), 7.40-7.35(m, 3H), 7.23-7.16(m, 3H), 2.48(s, 3H) |
| 37 | 610.22 | 8.82(d, 1H), 8.55(m, 2H), 7.94-7.89(m, 4H), 7.77(d, 1H), 7.62-7.50(m, 13H), 7.40-7.36(m, 2H), 7.16(m, 3H) |
| 38 | 585.22 | 9.30(s, 1H), 8.55(d, 1H), 8.39(d, 1H), 8.22-8.19(m, 2H), 8.04-7.94(m, 2H), 7.62-7.35(m, 18H), 7.20-7.16(m, 2H) |
| 39 | 790.28 | 8.55(m, 2H), 8.36(d, 4H), 8.26(s, 1H), 8.14(d, 1H), 7.96-7.50(m, 20H), 7.40-7.35(m, 4H), 7.16(m, 2H) |
| 40 | 464.19 | 9.12(s, 1H), 6.55(d, 1H), 7.94(d, 1H), 7.71-7.35(12H), 7.16(t, 1H), 7.02(d, 2H), 3.81(s, 3H), 2.69(s, 3H) |
| 41 | 435.17 | 9.24(s, 1H), 8.70(d, 1H), 8.55(d, 1H), 8.42-8.37(m, 2H), 7.94(d, 1H), 7.84(5, 1H), 7.62-7.35(m, 10H), 7.16(t, 1H), 3.03(s, 3H) |
| 42 | 477.13 | 9.10(d, 1H), 8.55(d, 1H), 8.45(d, 1H), 8.29(s, 1H), 8.03-7.91(m, 3H), 7.73(d, 1H), 7.62-7.49(m, 8H), 7.40-7.35(m, 2H), 7.16(t, 1H) |
| 43 | 588.23 | 8.74(d, 2H), 8.55(d, 1H), 7.94-7.88(t, 2H), 7.62-7.08(m, 23H) |
| 44 | 552.14 | 8.70(s, 1H), 8.55(m, 2H), 8.45(d, 1H), 8.32(d, 1H), 7.94-7.93(m, 2H), 7.62-7.35(m, 12H), 7.16(t, 1H) |
| 45 | 525.18 | 8.68(s, 1H), 8.55(d, 1H), 7.98-7.79(m, 6H), 7.62-7.50(m, 7H), 7.40-7.31(m, 4H), 7.16(t, 1H), 2.42(s, 3H) |
| 46 | 496.19 | 9.37(s, 1H), 8.55(d, 1H), 8.45(d, 1H), 7.94-7.91(m, 5H), 7.79-7.75(m, 4H), 7.61-7.35(11H), 7.16(t, 1H) |
| 47 | 653.21 | 8.87(d, 1H), 8.55-8.51(m, 3H), 7.99-7.89(m, 4H), 7.77(d, 1H), 7.62-7.35(m, 13H), 7.22-7.16(m, 4H) |
| 48 | 790.28 | 8.55(m, 2H), 8.36-8.31(m, 6H), 8.14(d, 1H), 7.96-7.91(m, 5H), 7.74-7.50(m, 15H), 7.40-7.35(m, 3H), 7.16(m, 2H) |
| 49 | 660.23 | 8.55((d, 1H), 8.22-7.35(m, 25H), 7.20-7.16(m, 2H) |
| 50 | 755.28 | 8.71(5, 1H), 8.64(d, 1H), 8.55(m, 2H), 8.46(d, 1H), 8.36(d, 4H), 7.99-7.94(m, 5H), 7.77(d, 1H), 7.50-7.35(m, 13H), 7.16(m, 2H), 2.68(s, 3H) |
| 51 | 526.2 | 8.81(d, 1H), 8.55(d, 1H), 8.44(d, 1H), 8.21(s, 1H), 7.94(d, 1H), 7.75-7.32(m, 15H), 7.16(t, 1H), 7.02(d, 2H), 3.81(s, 3H) |
| 52 | 753.29 | 8.59-8.55(m, 3H), 8.22-8.19(m, 2H), 8.04(d, 1H), 7.94(m, 5H), 7.58-7.32(m, 19H), 7.20-7.16(m, 2H), 2.68(s, 3H) |
| 53 | 439.15 | 9.32(s, 1H), 9.24(s, 1H), 8.70(d, 1H), 8.55-8.52(t, 2H), 8.42(d, 1H), 7.94(d, 1H), 7.84(s, 1H), 7.71-7.55(m, 5H), 7.40-7.34(m, 4H), 7.16(t, 1H) |

Example 1

A green phosphorescent top-emission light-emitting device is fabricated as follows.

As an anode, an ITO/Ag/ITO (70/1000/70 Å) substrate was cut to a size of 50 mm×50 mm×0.5 mm, sonicated using isopropyl alcohol and pure water for 5 minutes each, and then cleaned by irradiation of UV light for 30 minutes and exposure to ozone. Then, the resultant glass substrate was disposed in a vacuum deposition apparatus.

Then, 2-TNATA, which is a known hole injecting material, was vacuum deposited on the glass substrate to form an HIL having a thickness of 600 Å, and then Compound 43 according to an embodiment, instead of 4,4'-bis[N-(1-naphthyl)-N-phenylamino]biphenyl (NPB) that is a known hole transporting material, was vacuum deposited on the HIL to form an HTL having a thickness of 1,000 Å.

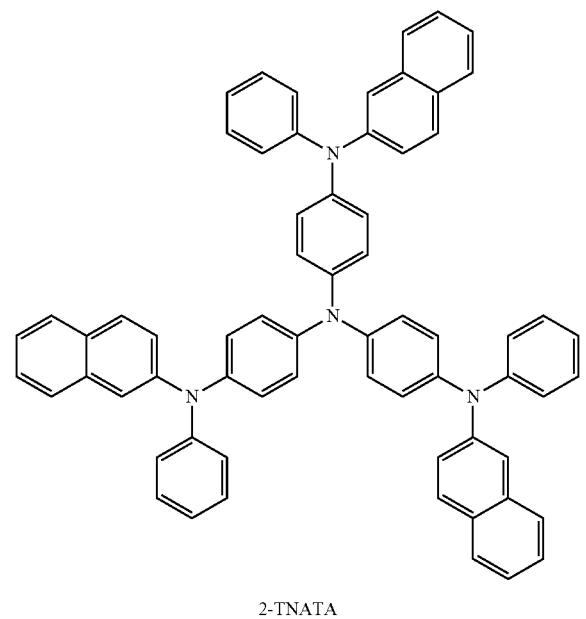

2-TNATA

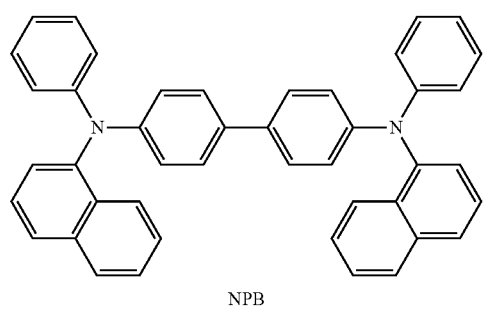

NPB

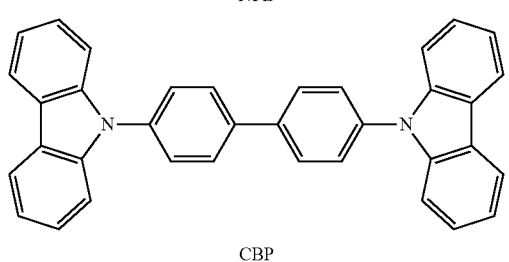

CBP

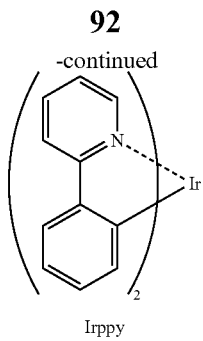

Irppy

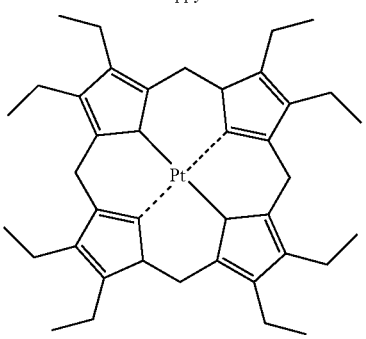

PtOEP

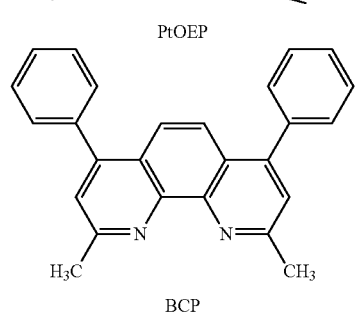

BCP

CBP, as a known green phosphorescent host, and Irppy, as a known green phosphorescent dopant, were co-deposited on the HTL at a weight ratio of 91:9 to form an EML having a thickness of 250 Å.

Then, BCP, as a hole blocking compound, was vacuum deposited on the EML to a thickness of 50 Å to form an HBL. Then, Alq3 was deposited on the HBL to form an ETL having a thickness of 350 Å, and then LiF, which is a halogenated alkali metal, was deposited on the ETL to form an EIL having a thickness of 10 Å. Then, Mg and Ag were vacuum deposited on the EIL at a weight ratio of 90:10 to form an electrode having a thickness of 120 Å. As a result, an organic light-emitting device was fabricated.

The organic light-emitting device had a driving voltage of 5.6 V at a current density of 50 mA/cm$^2$, a brightness of 6,609 cm/m$^2$, a luminous efficiency of 66.1 cd/A, and a half lifespan of 75 hr@100 mA/cm$^2$.

Example 2

An organic light-emitting device was fabricated in the same manner as in Example 1 except that Compound 52 according to an embodiment was used as the hole transporting material instead of Compound 43.

The organic light-emitting device had a driving voltage of 5.3 V at a current density of 50 mA/cm$^2$, a brightness of 6,721 cm/m$^2$, a luminous efficiency of 67.2 cd/A, and a half lifespan of 77 hr@100 mA/cm$^2$.

Example 3

An organic light-emitting device was fabricated in the same manner as in Example 1, except that NPB that is a known hole transporting material is used to form the HTL and Compound 16 according to an embodiment was used as the green phosphorescent host instead of using CBP.

The organic light-emitting device had a driving voltage of 5.5 V at a current density of 50 mA/cm$^2$, a brightness of 6,577 cm/m$^2$, a luminous efficiency of 65.7 cd/A, and a half lifespan of 74 hr@100 mA/cm$^2$.

Example 4

An organic light-emitting device was fabricated in the same manner as in Example 3, except that Compound 47 was used as the green phosphorescent host instead of using Compound 16.

The organic light-emitting device had a driving voltage of 5.4 V at a current density of 50 mA/cm$^2$, a brightness of 6,643 cm/m$^2$, a luminous efficiency of 66.4 cd/A, and a half lifespan of 75 hr@100 mA/cm$^2$.

Example 5

A red phosphorescent top-emission light-emitting device is fabricated as follows.

As an anode, an ITO/Ag/ITO (70/1000/70 Å) substrate was cut to a size of 50 mm×50 mm×0.5 mm, sonicated using isopropyl alcohol and pure water for 5 minutes each, and then cleaned by irradiation of UV light for 30 minutes and exposure to ozone. Then, the resultant glass substrate was disposed in a vacuum deposition apparatus.

2-TNATA, as a known hole injecting material, was vacuum deposited on the substrate to a thickness of 600 Å, and then NPB, as a hole transporting material, was vacuum deposited to a thickness of 1000 Å to form an HTL.

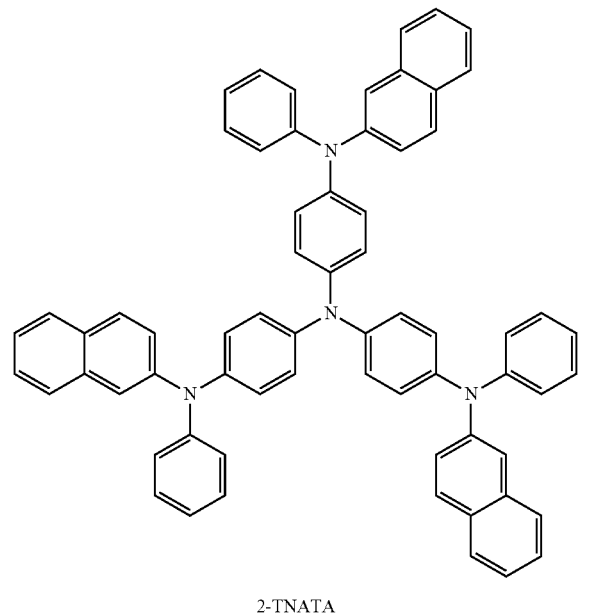

2-TNATA

NPB

CBP

Irppy

PtOEP

BCP

Compound 7 according to an embodiment, as a red phosphorescent host instead of known CBP, and PtOEP, as a known red phosphorescent dopant, were co-deposited on the HTL at a weight ratio of 91:9 to form an EML having a thickness of 250 Å.

Then, BCP, as a hole blocking compound, was vacuum deposited on the EML to a thickness of 50 Å to form an HBL. Then, Alq3 was deposited on the HBL to form an ETL having a thickness of 350 Å, and then LiF, which is a halogenated alkali metal, was deposited on the ETL to form an EIL having a thickness of 10 Å. Then, Mg and Ag were vacuum deposited on the EIL at a weight ratio of 90:10 to form an electrode having a thickness of 120 Å. As a result, an organic light-emitting device was fabricated.

The organic light-emitting device had a driving voltage of 6.0 V at a current density of 50 mA/cm$^2$, a brightness of 3,102 cm/m$^2$, a luminous efficiency of 30.1 cd/A, and a half lifespan of 108 hr@100 mA/cm$^2$.

Example 6

An organic light-emitting device was fabricated in the same manner as in Example 5, except that Compound 23 was used as the green phosphorescent host during formation of the EML instead of using Compound 7.

The organic light-emitting device had a driving voltage of 5.9 V at a current density of 50 mA/cm$^2$, a brightness of 3,168 cm/m$^2$, a luminous efficiency of 31.7 cd/A, and a half lifespan of 111 hr@100 mA/cm$^2$.

Example 7

An organic light-emitting device was fabricated in the same manner as in Example 1, except that Compound 47 according to an embodiment was used as the green phosphorescent host during formation of the EML instead of using known CBP.

The organic light-emitting device had a driving voltage of 5.5 V at a current density of 50 mA/cm$^2$, a brightness of 6,870 cm/m$^2$, a luminous efficiency of 68.7 cd/A, and a half lifespan of 76 hr@100 mA/cm$^2$.

Example 8

An organic light-emitting device was fabricated in the same manner as in Example 5, except that Compound 52 according to an embodiment was used during formation of the HTL instead of using known NPB.

The organic light-emitting device had a driving voltage of 6.1 V at a current density of 50 mA/cm$^2$, a brightness of 2,984 cm/m$^2$, a luminous efficiency of 29.8 cd/A, and a half lifespan of 123 hr@100 mA/cm$^2$.

Comparative Example 1

Figure 2:
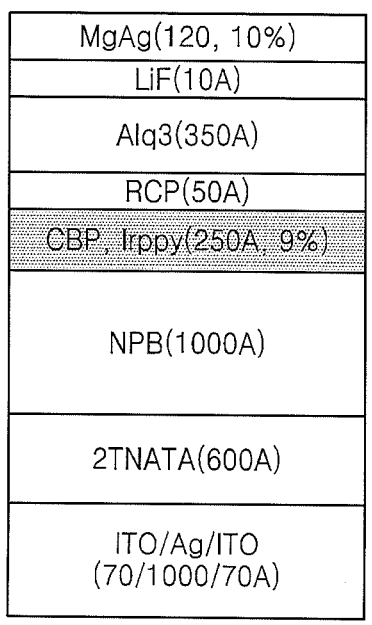
FIG. 2 is a schematic cross-sectional view of an organic light-emitting device according to Comparative Example 1.

A green phosphorescent top-emission light-emitting device having a structure as illustrated in FIG. 2 was fabricated.

The organic light-emitting device had a driving voltage of 6.8 V at a current density of 50 mA/cm$^2$, a brightness of 4,766 cm/m$^2$, a luminous efficiency of 47.7 cd/A, and a half lifespan of 61 hr@100 mA/cm$^2$.

Comparative Example 2

Figure 3:
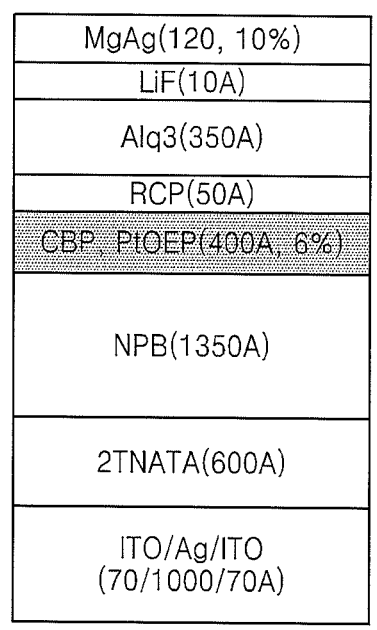
FIG. 3 is a schematic cross-sectional view of an organic light-emitting device according to Comparative Example 2.

A red phosphorescent top-emission light-emitting device having a structure as illustrated in FIG. 3 was fabricated.

The organic light-emitting device had a driving voltage of 7.3 V at a current density of 50 mA/cm$^2$, a brightness of 2,212 cm/m$^2$, a luminous efficiency of 22.1 cd/A, and a half lifespan of 89 hr@100 mA/cm$^2$.

Characteristics and lifespans of the organic light-emitting devices are shown in Table 3 below.

TABLE 3

| | Host or electron transporting material | Driving voltage (V) | Current density (mA/cm$^2$) | Brightness (cd/m$^2$) | Luminous efficiency (cd/A) | Color | LT$_{97}$ (hr) |
|---|---|---|---|---|---|---|---|
| Example 1 | HTL 43 | 5.6 | 10 | 6,609 | 66.1 | green | 75 |
| Example 2 | HTL 52 | 5.3 | 10 | 6,721 | 67.2 | green | 77 |
| Example 3 | Green phosphorescent host 16 | 5.5 | 10 | 6,577 | 65.7 | green | 74 |
| Example 4 | Green phosphorescent host 47 | 5.4 | 10 | 6,643 | 66.4 | green | 75 |
| Example 5 | Red phosphorescent host 7 | 6.0 | 10 | 3,012 | 30.1 | red | 108 |
| Example 6 | Red phosphorescent host 23 | 5.9 | 10 | 3,168 | 31.7 | red | 111 |
| Example 7 | HTL 43 Green phosphorescent host 47 | 5.5 | 10 | 6,870 | 68.7 | green | 76 |
| Example 8 | HTL 52 Green phosphorescent host 7 | 6.1 | 10 | 2,984 | 29.8 | red | 123 |
| Comparative Example 1 | CBP/Irppy | 6.8 | 10 | 4,766 | 47.7 | green | 61 |
| Comparative Example 2 | CBP/porphyrin | 7.3 | 10 | 2,212 | 22.1 | red | 89 |

When the heterocyclic compound represented by Formula 1, particularly, Formulae 2 and 3, is used in an organic light-emitting device as a hole transporting material or a light emitting material, driving voltage and lifespan characteristics, particularly, luminous efficiency, may be more improved than Comparative Examples 1 and 2.

The heterocyclic compound represented by Formula 1 has excellent light emitting characteristics and high charge transporting capabilities. Particularly, the heterocyclic compound may be efficiently used as green and red phosphorescent materials. Accordingly, an organic light-emitting device having high luminous efficiency, low driving voltage, high brightness, and long lifespan may be fabricated using the heterocyclic compound.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept.

What is claimed is:

1. A heterocyclic compound represented by one selected from Formulae 2 and 3 below:

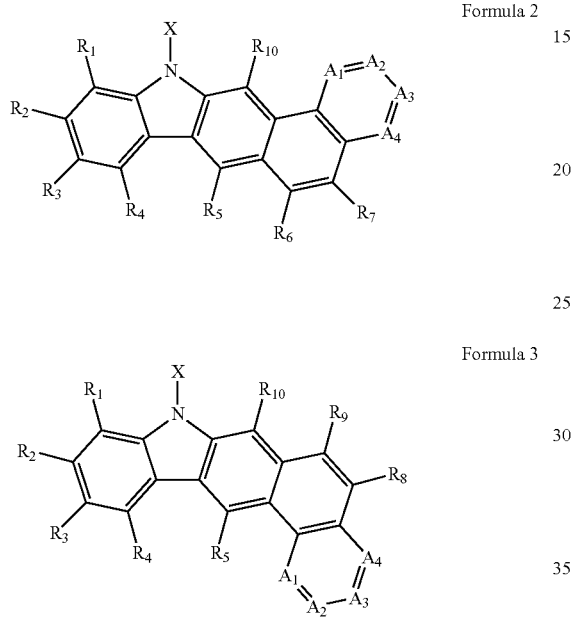

Formula 2

Formula 3 where $R_1$ to $R_{10}$ are each independently a hydrogen atom, a deuterium atom, a halogen atom, a cyano group, a substituted or unsubstituted $C_1$-$C_{60}$ alkyl group, a substituted or unsubstituted $C_1$-$C_{60}$ alkenyl group, a substituted or unsubstituted $C_1$-$C_{60}$ alkynyl group, a substituted or unsubstituted $C_6$-$C_{60}$ aryl group, a substituted or unsubstituted $C_1$-$C_{60}$ heteroaryl group, an amino group substituted with a $C_6$-$C_{60}$ aryl group, a $C_1$-$C_{60}$ alkyl group, a $C_1$-$C_{60}$ alkenyl group, or a $C_1$-$C_{60}$ alkynyl group, or a substituted or unsubstituted $C_6$-$C_{60}$ condensed polycyclic group, X is a substituted or unsubstituted $C_1$-$C_{50}$ alkyl group, a substituted or unsubstituted $C_6$-$C_{60}$ aryl group, a substituted or unsubstituted heteroaryl group, or a substituted or unsubstituted $C_6$-$C_{60}$ condensed polycyclic group; and wherein $A_1$ to $A_4$ are each independently =$CR_{21}$— or =$NR_{22}$—, and at least one selected from $A_1$ to $A_4$ is =$NR_{22}$— in Formula 2, and $R_{21}$ is: a non-bonding pair of electrons; a hydrogen atom; a deuterium atom; a halogen atom; a cyano group; a substituted or unsubstituted $C_1$-$C_{60}$ alkyl group; a substituted or unsubstituted alkenyl group; a substituted or unsubstituted $C_1$-$C_{60}$ alkynyl group; a substituted or unsubstituted $C_6$-$C_{60}$ aryl group; a substituted or unsubstituted heteroaryl group; an amino group substituted with a $C_6$-$C_{60}$ aryl group, a $C_1$-$C_{60}$ alkyl group, a $C_1$-$C_{60}$ alkenyl group, or a $C_1$-$C_{60}$ alkynyl group; or a substituted or unsubstituted $C_6$-$C_{60}$ condensed polycyclic group, $R_{22}$ is a non-bonding pair of electrons, and $R_{21}$ and $R_{22}$ of $A_1$ to $A_4$ are same or different, and adjacent $R_{21}$ and $R_{22}$ are selectively fused to each other, thereby forming a ring; and wherein $R_7$ of Formula 2 and $R_8$ of Formula 3 are each independently one of Formulae 2a to 2c below:

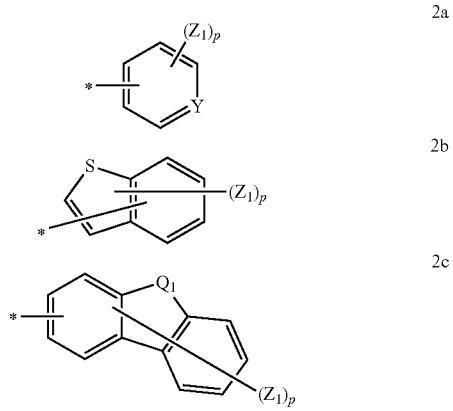

2a

2b

2c where $Q_1$ is a linking group represented by —N($R_{31}$)—, —S—, or —O; Y is —N= or —CH=; $Z_1$ and $R_{31}$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted heteroaryl group, a substituted or unsubstituted $C_6$-$C_{20}$ condensed polycyclic group, an amino group substituted with a $C_6$-$C_{20}$ aryl group or a $C_1$-$C_{20}$ heteroaryl group, a halogen group, a cyano group, a nitro group, a hydroxyl group, or a carboxyl group;

p is an integer from 1 to 4 in Formula 2a;
p is an integer from 1 to 5 in Formula 2b;
p is an integer from 1 to 7 in Formula 2c; and
* is a binding site.

2. The heterocyclic compound of claim 1, wherein X of Formula 2 or 3 is a compound represented by Formula 3a or 3b below:

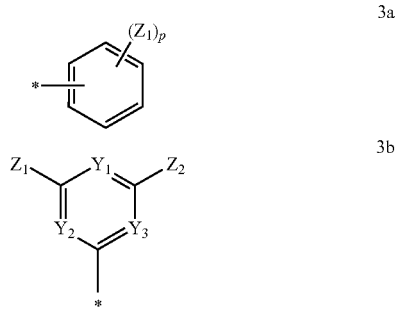

3a

3b where $Y_1$ to $Y_3$ are each independently —N= or —CH=;

$Z_1$ and $Z_2$ are each independently a hydrogen atom, a deuterium atom, a substituted or unsubstituted $C_1$-$C_{20}$ alkyl group, a substituted or unsubstituted $C_6$-$C_{20}$ aryl group, a substituted or unsubstituted $C_1$-$C_{20}$ heteroaryl group, a substituted or unsubstituted $C_6$-$C_{20}$ condensed polycyclic group, an amino group substituted with a $C_6$-$C_{20}$ aryl group or a $C_1$-$C_{20}$ heteroaryl group, a halogen group, a cyano group, a nitro group, a hydroxyl group, or a carboxyl group;

p is an integer from 1 to 5; and

* is a binding site.

3. The heterocyclic compound of claim 1, wherein $R_1$ to $R_5$ and $R_{10}$ of Formula 2 or 3 are each independently a hydrogen atom or a deuterium atom.

4. The heterocyclic compound of claim 1, wherein the heterocyclic compound represented by Formula 2 or 3 comprises one of the of the compounds below:

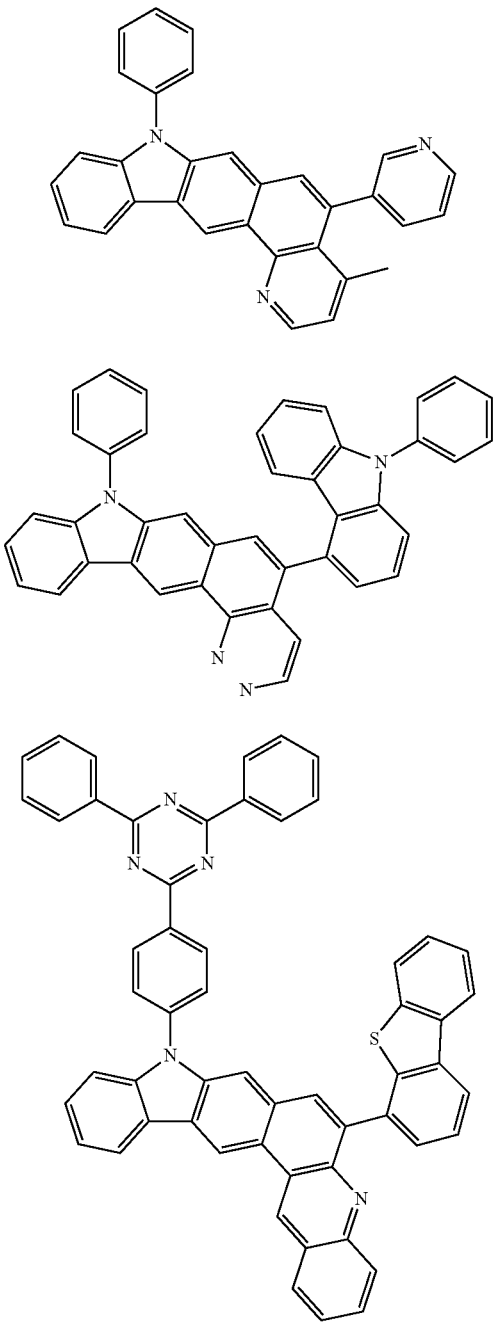

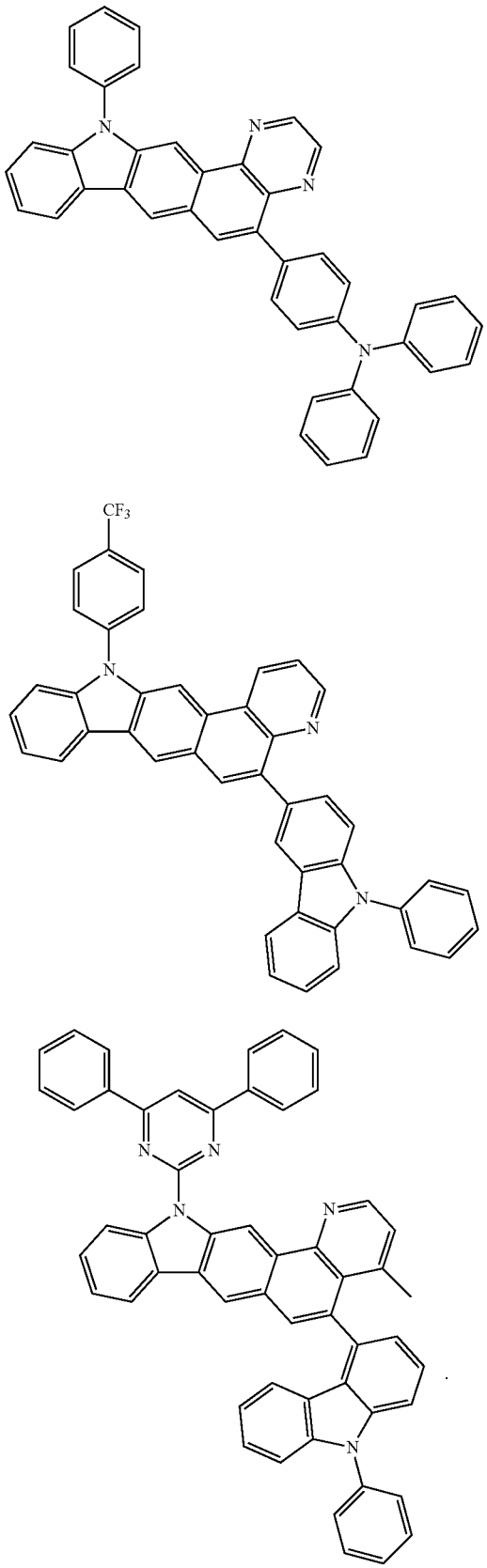

5. An organic light-emitting device comprising:
a first electrode;
a second electrode; and
an organic layer interposed between the first electrode and the second electrode,
wherein the organic layer comprises a heterocyclic compound of claim 1.

6. The organic light-emitting device of claim 5, wherein the organic layer is an emission layer, and the heterocyclic compound is used as a phosphorescent host.

7. The organic light-emitting device of claim 5, wherein the organic layer is an electron transport layer, and the heterocyclic compound is used as an electron transporting material.

8. The organic light-emitting device of claim 5, wherein the organic layer is a hole transport layer, and the heterocyclic compound is used as a hole transporting material.

9. The organic light-emitting device of claim 5, wherein the organic layer is a green emission layer or a red emission layer.

10. The organic light-emitting device of claim 5, wherein the organic light-emitting device comprises an emission layer, a hole injection layer, a hole transport layer, or a functional layer having both hole injecting and hole transporting capabilities,
the emission layer, the hole injection layer, the hole transport layer, or the functional layer having both hole injecting and hole transporting capabilities comprises the heterocyclic compound, and
the emission layer comprises an anthracene-based compound, an arylamine-based compound, or a styryl-based compound.

11. The organic light-emitting device of claim 5, wherein the organic light-emitting device comprises an emission layer, a hole injection layer, a hole transport layer, or a functional layer having both hole injecting and hole transporting capabilities,
the emission layer, the hole injection layer, the hole transport layer, or the functional layer having both hole injecting and hole transporting capabilities comprises the heterocyclic compound, and
wherein a red layer, a green layer, a blue layer, or a white layer of the emission layer further comprises a phosphorescent compound.

12. The organic light-emitting device of claim 11, wherein the hole injection layer, the hole transport layer, and the functional layer having both hole injecting and hole transporting capabilities comprises a charge-generating material.

13. The organic light-emitting device of claim 12, wherein the charge-generating material is a p-dopant comprising a quinone derivative, a metal oxide, or a cyano group-containing compound.

14. The organic light-emitting device of claim 5, wherein the organic layer comprises an electron transport layer, and the electron transport layer comprises an electron transporting organic compound and a metal complex.

15. The organic light-emitting device of claim 14, wherein the metal complex comprises a lithium quinolate (LiQ) or Compound 203 below:

Compound 203

16. The organic light-emitting device of claim 5, wherein the organic layer is formed of the heterocyclic compound by using a wet process.

17. A flat panel display apparatus comprising
an organic light-emitting device comprising:
a first electrode;
a second electrode; and
an organic layer interposed between the first electrode and the second electrode,
wherein the organic layer comprises a heterocyclic compound of claim 1.

* * * * *